United States Patent
Hummersone et al.

(10) Patent No.: US 11,097,252 B2
(45) Date of Patent: Aug. 24, 2021

(54) FUNCTIONALISED CHROMATOGRAPHY MEDIUM COMPRISING POLYMER NANOFIBRES AND PROCESS OF PREPARATION THEREOF

(71) Applicant: Puridify Ltd., Hertfordshire (GB)

(72) Inventors: Marc Hummersone, Hertfordshire (GB); Benjamin Wallis, Hertfordshire (GB); Frederic Leroux, Greater London (GB); William Law, Cambridgeshire (GB)

(73) Assignee: Puridify Ltd., Hertfordshire (GB)

( * ) Notice: Subject to any disclaimer, the term of this patent is extended or adjusted under 35 U.S.C. 154(b) by 188 days.

(21) Appl. No.: 16/315,088

(22) PCT Filed: Jul. 14, 2017

(86) PCT No.: PCT/GB2017/052085
§ 371 (c)(1),
(2) Date: Jan. 3, 2019

(87) PCT Pub. No.: WO2018/011600
PCT Pub. Date: Jan. 18, 2018

(65) Prior Publication Data
US 2019/0308169 A1    Oct. 10, 2019

(30) Foreign Application Priority Data

Jul. 14, 2016 (GB) ..................... 1612249
Jul. 14, 2016 (GB) ..................... 1612252
Jun. 22, 2017 (GB) ..................... 1709996

(51) Int. Cl.
*B01D 15/20* (2006.01)
*B01D 15/38* (2006.01)
(Continued)

(52) U.S. Cl.
CPC ........... *B01J 20/265* (2013.01); *B01D 15/20* (2013.01); *B01D 15/3809* (2013.01);
(Continued)

(58) Field of Classification Search
CPC .. B01D 15/20; B01D 15/3809; B01D 20/265; B01D 20/28023; B01D 20/28038;
(Continued)

(56) References Cited

U.S. PATENT DOCUMENTS

2006/0040280 A1   2/2006   Lee et al.
2012/0029176 A1   2/2012   Yavorsky et al.
(Continued)

FOREIGN PATENT DOCUMENTS

WO   2004/003542 A1   1/2004
WO   2014/120387 A1   8/2014
(Continued)

OTHER PUBLICATIONS

Rhodes, S., etal, "Hyperbranched polyol/carbon nanofiber composites", Polymer 48, 1500-1509. (Year: 2007).*
(Continued)

*Primary Examiner* — Benjamin L Lebron
(74) *Attorney, Agent, or Firm* — Eversheds Sutherland (US) LLP

(57) ABSTRACT

The present invention provides a functionalised polymeric chromatography medium, prepared by a process which comprises (i) providing a substrate formed of one or more polymer nanofibres, (ii) grafting one or more neutral polymer chains from the substrate, and (iii) contacting the grafted product with a reagent which functionalises the product of step (ii) as a chromatography medium, wherein step (ii) comprises reacting a plurality of compounds of formula and/or its enantiomers, and/or its derivatives of
(Continued)

formula (I) and/or enantiomers and/or diastereomers thereof: with one or more functional groups present on the nanofibre substrate, wherein $R_1$, $R_2$, $R_3$, $R_4$ and $R_5$ may be the same or different, and are chosen from H, halogen, $C_1$-$C_4$ alkyl, or $C_1$-$C_4$ alkoxy provided that at least one of $R_1$, $R_2$, $R_3$, $R_4$ or $R_5$ is not hydrogen.

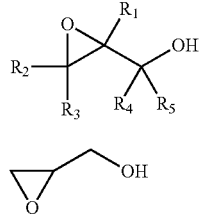

32 Claims, 13 Drawing Sheets

(51) Int. Cl.
```
B01J 20/26      (2006.01)
B01J 20/28      (2006.01)
B01J 20/286     (2006.01)
B01J 20/289     (2006.01)
B01J 20/30      (2006.01)
B01J 20/32      (2006.01)
C07K 1/16       (2006.01)
```
(52) U.S. Cl.
CPC .......... *B01J 20/286* (2013.01); *B01J 20/289* (2013.01); *B01J 20/28023* (2013.01); *B01J 20/28038* (2013.01); *B01J 20/28052* (2013.01); *B01J 20/3085* (2013.01); *B01J 20/3092* (2013.01); *B01J 20/321* (2013.01); *B01J 20/328* (2013.01); *B01J 20/3212* (2013.01); *B01J 20/3217* (2013.01); *B01J 20/3219* (2013.01); *B01J 20/3227* (2013.01); *B01J 20/3248* (2013.01); *B01J 20/3272* (2013.01); *B01J 20/3293* (2013.01); *C07K 1/16* (2013.01); *B01J 2220/62* (2013.01)

(58) Field of Classification Search
CPC .......... B01D 20/28052; B01D 20/286; B01D 20/289; B01D 20/3085; B01D 20/3092; B01D 20/321; B01D 20/3212; B01D 20/3217; B01D 20/3219; B01D 20/3227; B01D 20/3248; B01D 20/3272; B01D 20/328; B01D 20/3293; B01J 2220/62; C07K 1/16

See application file for complete search history.

(56) References Cited

U.S. PATENT DOCUMENTS

2014/0069870 A1    3/2014   Pohl
2015/0258540 A1    9/2015   Yavorsky et al.

FOREIGN PATENT DOCUMENTS

WO    WO-2015052465 A1 *  4/2015   ......... B01D 15/3809
WO       2018/011600 A1    1/2018
WO       2019/137869 A1    7/2019

OTHER PUBLICATIONS

PCT International Search Report and Written Opinion for PCT Application No. PCT/GB2017/052085 dated Oct. 20, 2017 (10 pages).
PCT International Search Report and Written Opinion for PCT Application No. PCT/EP2019/050227 dated Apr. 4, 2019 (13 pages).
GB Search Report for GB Application No. 1800448.1 dated Jul. 2, 2018 (9 pages).
PCT International Search Report and Written Opinion for PCT Application No. PCT/EP2019/050227 dated Apr. 4, 2019 (17 pages).
Feng et al., "Electrospun Regenerated Cellulose Nanofibrous Membranes Surface-Grafted with Polymer Chains/Brushes via the Atom Transfer Radical Polymerization Method for Catalase Immobilization," ACS Appl. Mater. Interfaces, 2014, 6:20958-20967.
Gottschalk, "Bioseparation in Antibody Manufacturing: The Good, The Bad and The Ugly," Biotechnol. Prog., 2008, 24:496-503.
Hardick et al., "Nanofibre Fabrication in a Temperature and Humidity Controlled Environment for Improved Fibre Consistency," J Mater Sci, 2011, 46:3890-3898.
Ma et al., "Electrospun Polyethersulfone Affinity Membrane: Membrane Preparation and Perfomance Evaluation," Journal of Chromatography B, 2009, 877:3686-3694.
Ma et al., "Surface Modified Nonwoven Polysulphone (PSU) Fiber Mesh by Electrospinning: A Novel Affinity Membrane," Journal of Membrance Science, 2006, 272:179-187.
Menkhaus et al., "Electrospun Nanofiber Membranes Surface Functionalized with 3-Dimensional Nanolayers as an Innovative Adsorption Medium with Ultra-High Capacity and Throughput," The Royal Society of Chemistry, 2010, 46:3720-3722.
Moffat, "Structure and Composition Factors in the Acidity and Basicity of Inorganic Molecular Metal-Oxygen Cluster Catalysts and Their Influence on the Surface and Catalytic Properties," J. Frassard and L Petrakis (eds.), Acidity and Basicity of Solids, 1994, 217-335.
Rajesh et al., "Synthesis of Cellulose-Graft-Polypropionic Acid Nanofiber Cation-Exchange Membrane Adsorbers for High-Efficiency Separations," ACS Appl. Mater. Interfaces, 2017, 9:41055-41065.
Rathore et al., Re-Use of Protein A Resin: Fouling and Economics, BioPharm International, 2015, vol. 3, Issue 28, 7 pages.
European Search Report for EP Application No. 21155004 dated May 18, 2021 (11 pages).

* cited by examiner

FUNCTIONALISED CHROMATOGRAPHY MEDIUM COMPRISING POLYMER NANOFIBRES AND PROCESS OF PREPARATION THEREOF

CROSS REFERENCE TO RELATED APPLICATIONS

This application claims the priority benefit of PCT/GB2017/052085 filed on Jul. 14, 2017 which claims priority benefit of Great Britain Application Nos. 1612249.1, 1612252.5, and 1709996.1, filed Jul. 14, 2016, Jul. 14, 2016, and Jun. 22, 2017, respectively. The entire contents of which are hereby incorporated by reference herein.

FIELD OF THE INVENTION

The invention relates to functionalised chromatography media which are suitable for isolating biological molecules from mobile phases.

BACKGROUND TO THE INVENTION

The biotechnology market is the fastest growing sector within the world pharmaceutical market, accounting for 20% ($153bn) of all market sales in 2012. This growth from 10% of the market share in 2002 is set to grow by 41% between 2012 and 2018 from $153bn to $215bn. There are currently around 200 monoclonal antibody (MAb) products on the market, and with over 1000 in clinical trials, the need for technological advancement in this area is clear. Over the last few decades typical fermentation titres of biomolecules in industrial settings have grown from 0.5 g/L-~3 g/L, with levels of up to 10 g/L believed to be achievable in the near future based on activated advancements in molecular biology. Yet, while the downstream purification processes have also received some research and development, improvements in this area have not matched those in the upstream.

The manufacture of therapeutic proteins requires that a high degree of purity be achieved during processing so that the protein to be administered is substantially devoid of harmful contaminants. Currently, on industrial scale, chromatography is the dominant methodology used to achieve high purity proteins. The heavily relied on chromatography unit operations are, in economic terms, the key to advancements in the downstream processing of biomolecules, such as MAbs. Chromatography accounts for up to 60% of biotherapeutic processing (Re-use of Protein A Resin: Fouling and Economics, Mar. 1, 2015 BioPharm International, Volume 28, Issue 3, Anurag S. Rathore, Mili Pathak, Guijun Ma, Daniel G. Bracewell).

Such chromatographic separations involve binding of i) the target molecule and/or, ii) one or more impurities, to a solid phase when a liquid phase containing the target molecule and impurities is contacted with the solid phase. The interaction between target molecule/impurities and the solid phase can be based on charge, hydrophobicity, affinity or a combination thereof.

Historically, conventional packed bed chromatography using porous beads has been an extremely powerful separation tool. The porous nature of these beads yields a high surface area for binding either target or impurity. This results in a high capacity material, meaning a smaller amount of adsorbent material can be used. High capacities also increase the concentration effect achieved during the separation as more target can be bound per unit volume of adsorbent compared to the relative concentration of the load suspension. These aspects are critical for industrial scale processing where several kilograms of material might need to be purified per batch from liquid volumes that can reach up to 20,000 L. Typical binding capacities for porous beads are in the region of 35-120 mg/mL dependant on the functionality of the solid phase and species bound.

In a porous bead-based system, the binding event between target molecule/impurity and the solid phase is dependent on diffusion into the porous bead. There is therefore a strong correlation between the residence time in a porous bead-based system and flowrate. Thus, binding capacity drops off with decreasing residence times. This in turn is accompanied by rapid reduction of capacity where times of less than 2 minutes are used in a porous bead-based system. The high flowrates required for short residence times can also be incompatible with porous beads, particularly at manufacturing scale where many litres of bead suspension are packed into a column. Here the mechanical instability of the porous beads can lead to compression or collapse events, which in turn results in a non-homogeneous column bed.

With flowrate impacting the residence time it is critical to maximise the amount of target that can be bound to the solid phase per unit time. This allows either smaller adsorbent volumes to be used and/or the separation to be performed in less time. This metric can be defined as grams bound, per unit volume, per unit time (mg/mL/min). The typical binding capacities and residence times for porous beads discussed above result in overall productivities for single column porous bead systems around 10-120 mg/mL/min.

As alternatives to porous bead-based systems, monoliths or membranes may be used. The flow through such materials is convective rather than diffusional, and their binding capacity is therefore far less sensitive to flow than porous bead-based systems. These materials can be run at far higher flowrates than porous bead-based materials, where typical residence times are in the order of 0.2-0.5 minutes.

However, typical binding capacities at 10% breakthrough of target for monoliths (10-20 mg/mL) and membranes (7.5-29 mg/mL) under dynamic flow are lower than porous beads (Gottschalk, U. (2008). Biotechnol Prog, 24(3), 496-503. doi: 10.1021/bp070452 g). The inferior binding capacity of monolith and membrane materials (compared to porous bead-based materials) can be offset to some extent by utilising higher flowrates.

The typical binding capacities and residence times for monoliths and membranes discussed above result in overall productivities of the binding event for monolith and membrane systems around 10-145 mg/mL/min.

There exists a need for chromatography materials which share high binding capacity associated with porous bead-based materials and higher flowrates that are achievable with monolith/membrane materials. Such a material would offer high capacity at high flowrates to achieve maximum productivity (mg/mL/min).

The inventors have surprisingly found that a nanofibre material produced by a 2-step process, in which a functionalisation step is performed independently of a grafting step, exhibits such advantageous properties. The material produced by this method has a significantly increased binding capacity compared to a non-grafted material. The capacities displayed by the products of the invention are comparable or exceed those normally only achievable using porous beads, and are several fold higher than those achievable with currently commercialised membrane and monolith technologies. Furthermore, these capacities can be achieved at sub-second residence times resulting in productivity values which are 10-100 or even several 1000 times greater than conventional commercially available materials.

The materials produced in accordance with the present invention rely on a number of surprising innovations. Firstly, it has been found by the present inventors that for a set density of ligand groups, i.e. groups bonded to the chromatography medium that selectively bind to the target biomolecule, increasing the amount of grafting may increase the binding capacity of a chromatography material. It had previously been understood in the context of chromatography media functionalised with charged groups that increasing the amount of those charged groups increases the charge density of the material, and the binding capacity of the material. Previous approaches to maximising binding capacities of materials had therefore focussed on maximising charge density. However, for the first time the present inventors have shown that by increasing grafting, binding capacity may be increased independently of the charge density of the material.

In other cases, it has been found that altering the functionalization step can have little impact on charge density, but when combined with a grafting step a significant increase in binding capacity can be achieved for the same degree of functionalization.

It has thus been found that the charge density and binding capacity of chromatographic materials can be controlled by changing both the degree of functionalization and degree of grafting to give a highly optimised material. This relationship between the grafting step and the subsequent functionalization step has been researched and exploited by the present inventors to produce materials with very high binding capacities at high flowrates. The relationship between charge density and dynamic binding capacity was found to be much more subtle than had previously been appreciated. Thus, for materials with the same charge density it has been found that the dynamic binding capacity could be varied by controlling the degree of grafting. This was an unexpected and highly advantageous result.

This is highly significant, since previous attempts to increase capacity of chromatographic materials have focussed solely on increasing the density of ligand groups on the materials. Therefore, they fail to address how the capacity of the material can be controlled and increased by independently varying the conditions of the grafting and functionalization as isolated steps. In many of the known modification processes, this degree of control was simply not possible since chromatographic materials were modified with charged polymers, i.e. the grafting and functionalisation steps were carried out simultaneously.

Importantly, as well as increasing the binding capacity of the material, grafting and functionalization also has the effect of modulating the resistance to flow of the material, which has a detrimental impact upon the productivity of the chromatography material. This is discussed in Menkhaus el al. (Menkhaus, T. J., Varadaraju, H., Zhang, L., Schneiderman, S., Bjustrom, S., Liu, L., & Fong, H. (2010). Chemical Communications, 46(21), 3720-3722. doi: 10.1039/C001802C), which reports that increasing grafting may be associated with increased resistance to flow and increased diffusional aspects of mass transfer in convective media. This may be because known methods of modifying chromatography materials typically graft a charged polymer chain from the surface of the material. Thus, increasing the degree of grafting also increases the charge density of the material with no way to independently control these to optimise binding capacity and flow characteristics of the material.

These drawbacks have been overcome in the present invention by separating the grafting step from the step of functionalising the material. It has also been found that increasing the degree of grafting does not, in itself, increase the resistance to flow through the material. It is only when the grafted material is functionalised that resistance to flow starts to be affected.

Further, the present inventors have discovered that glycidol and its derivatives are particularly preferred monomer units to use in the grafting step. Surprisingly, when the grafting step employs glycidol polymerisation, the resultant chromatography media display improved properties (e.g., they benefit from a higher capacity and a higher productivity) than the chromatography media produced from other grafting methods, such as atom transfer radical polymerisation (ATRP).

SUMMARY OF THE INVENTION

Accordingly, the present invention provides a process for preparing a functionalised polymeric chromatography medium. The described process comprises:
(i) providing a substrate formed of one or more polymer nanofibres,
(ii) grafting one or more neutral polymer chains from the substrate, and
(iii) contacting the grafted product with a reagent which functionalises the product of step (ii) as a chromatography medium,
wherein step (ii) comprises reacting a plurality of compounds of formula

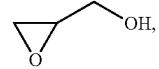

and/or its enantiomers, and/or its derivatives of formula (I) and/or enantiomers and/or diastereomers thereof:

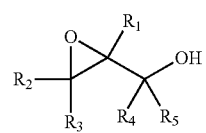

(I)

with one or more functional groups present on the nanofibre substrate,
wherein $R_1$, $R_2$, $R_3$, $R_4$ and $R_5$ may be the same or different, and are chosen from H, halo, $C_1$-$C_4$ alkyl, or $C_1$-$C_4$ alkoxy provided that at least one of $R_1$, $R_2$, $R_3$, $R_4$ or $R_5$ is not hydrogen.

The present invention also provides:
A functionalised chromatography medium obtainable by the process of the present invention.
A process for preparing a chromatography cartridge, which process comprises carrying out the process of the present invention and incorporating the thus-obtained product into a cartridge.
A chromatography cartridge which (a) is obtainable by said process, or (b) which comprises one or more functionalised chromatography media of the invention.
Use of a functionalised chromatography medium of the invention or a chromatography cartridge of the invention in chromatography.

A process for isolating one or more biological molecules from a mobile phase, which process comprises contacting one or more biological molecules in a mobile phase with a functionalised chromatography medium of the invention or a chromatography cartridge of the invention.

DETAILED DESCRIPTION OF THE INVENTION

Figure 1:
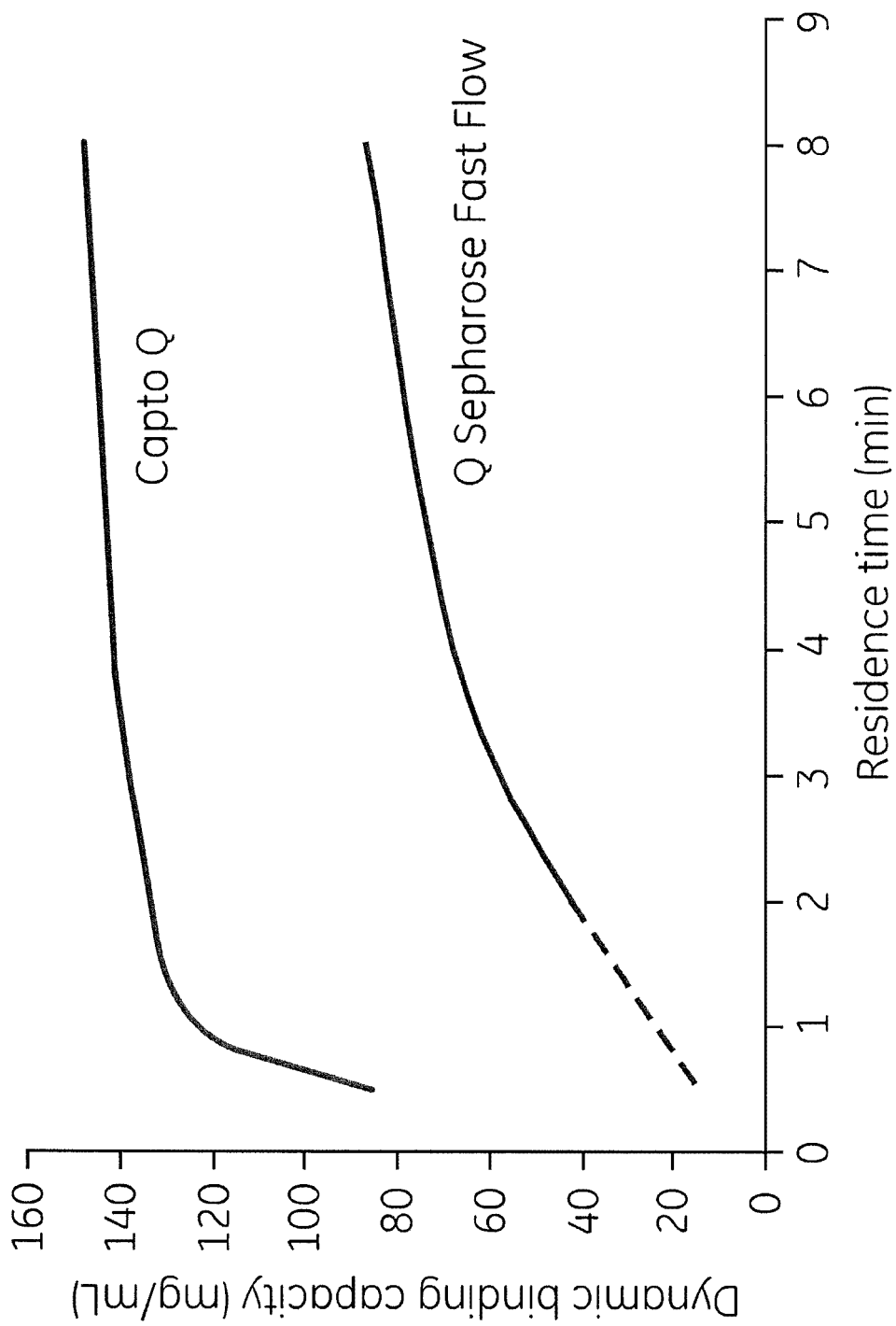
FIG. 1 shows dynamic binding capacity (DBC) as a function of residence time for a number of commercially available porous bead-based systems.

The present invention involves a two-step process for preparing a functionalised polymeric chromatography medium from a polymer nanofibre substrate. The two steps are a polymer grafting step, and a functionalisation step.

Polymer Nanofibres

The functionalised polymeric chromatography media of the present invention are formed from polymeric nanofibre substrates. Each substrate is formed of one or more polymer nanofibres.

The polymer nanofibres are typically electrospun polymer nanofibres. Such electrospun polymer nanofibres are well known to the person skilled in the art and optimised conditions for their production can be found in, for example, O. Hardick, et al., J. Mater. Sci. 46 (2011) 3890, the entirety of which is incorporated herein by reference. The processes of the present invention typically comprise an initial step of electrospinning a polymer to produce one or more polymer nanofibres. This may involve electrospinning a polymer to produce one or more non-woven sheets, each comprising one or more polymer nanofibres.

Polymer nanofibres for use in the present invention typically have mean diameters from 10 nm to 1000 nm. For some applications, polymer nanofibres having mean diameters from 200 nm to 800 nm are appropriate. Polymer nanofibres having mean diameters from 200 nm to 400 nm may be appropriate for certain applications.

The length of polymer nanofibres for use in the present invention is not particularly limited. Thus, conventional electrospinning processes can produce polymer nanofibres many hundreds of metres or even kilometres in length. Typically, though, the one or more polymer nanofibres have a length up to 10 km, preferably from 10 m to 10 km.

Typically, the one or more polymer nanofibres are provided in the form of one or more non-woven sheets, each comprising one or more polymer nanofibres. Thus, the substrate is typically formed of one or more non-woven sheets, each comprising one or more polymer nanofibres. A non-woven sheet comprising one or more polymer nanofibres is a mat of said one or more polymer nanofibres with each nanofibre oriented essentially randomly, i.e. it has not been fabricated so that the nanofibre or nanofibres adopts a particular pattern. Non-woven sheets comprising polymer nanofibres are typically provided by known methods, such as that disclosed in O. Hardick, et al., J. Mater. Sci. 46 (2011) 3890. Non-woven sheets may, in certain circumstances, consist of a single polymer nanofibre. Alternatively, non-woven sheets may comprise two or more polymer nanofibres, for example 2, 3, 4, 5, 6, 7, 8, 9 or 10 polymer nanofibres.

Non-woven sheets typically have area densities from 1 to 40 g/m², preferably from 5 to 25 g/m², in some circumstances from 1 to 20 or 5 to 15 g/m².

Non-woven sheets typically have a thickness from 5 to 120 μm, preferably from 10 to 100 μm, in some circumstances from 50 to 90 μm, in other circumstances from 5 to 40, 10 to 30 or 15 to 25 μm.

The polymer used to produce the nanofibres used in the processes of the present invention is not particularly limited, provided the polymer is suitable for use in chromatography applications. Thus, typically, the polymer is a polymer suitable for use as a chromatography medium, i.e. an adsorbent, in a chromatography method. Suitable polymers include polyamides such as nylon, polyacrylic acid, polymethacrylic acid, polyacrylonitrile, polystyrene, polysulfones e.g. polyethersulfone (PES), polycaprolactone, collagen, chitosan, polyethylene oxide, agarose, agarose acetate, cellulose, cellulose acetate, and combinations thereof. Polyethersulfone (PES), cellulose, cellulose acetate, and combinations thereof are preferred. In some cases, cellulose, cellulose acetate, and combinations thereof are preferred.

In some embodiments, the substrate comprises one or more nanofibres formed from one or more polymer nanofibres formed from different polymers. Thus, in this embodiment, the substrate comprises one or more different polymers. Typical polymers are as defined above.

Typically, the process of the present invention is for preparing a functionalised cellulose chromatography medium, and the process comprises providing a substrate formed of one or more cellulose acetate nanofibres. Preferably, the process comprises providing a substrate formed of one or more non-woven sheets, each comprising one or more cellulose acetate nanofibres. Cellulose acetate is readily electrospun and can readily be transformed into cellulose after electrospinning. Thus, preferably the process comprises providing a substrate formed of one or more non-woven sheets, each comprising one or more electrospun cellulose acetate nanofibres.

The substrate formed of one or more polymer nanofibres comprises the one or more polymer nanofibres, typically in the form of one or more non-woven sheets as discussed above. In certain embodiments, the one or more polymer nanofibres or one or more non-woven sheets are not subjected to any physical processing steps before the grafting step.

Physical Modification of Nanofibres

However, in certain preferred embodiments of the invention, provision of a substrate involves physical modification of the polymer nanofibres optionally in the non-woven sheets, prior to the grafting step. Specifically, physical modification may involve heating and/or pressing the polymer nanofibres/non-woven sheets, preferably heating and pressing the polymer nanofibres/non-woven sheets. These steps improve the structural stability of the material. The pressing and heating conditions may also be varied to alter the thickness and/or porosity of the resultant material.

Use of multiple non-woven sheets of polymer nanofibres enables a thicker material to be prepared which has a greater capacity for adsorbence (once grafted and functionalised). The provision of a substrate typically therefore comprises providing two or more non-woven sheets stacked one on top of the other, each said sheet comprising one or more polymer nanofibres, and simultaneously heating and pressing the stack of sheets to fuse points of contact between the nanofibres of adjacent sheets.

In the case of a cellulose chromatography medium, provision of a substrate typically comprises providing two or more non-woven sheets stacked one on top of the other, each said sheet comprising one or more cellulose acetate nanofibres, and simultaneously heating and pressing the stack of sheets to fuse points of contact between the nanofibres of adjacent sheets.

Preferred processing conditions for pressing and heating of polymer nanofibres/non-woven sheets can be found in WO-A-2015/052460 and WO-A-2015/052465, the entirety of which are incorporated herein by reference.

Grafting Nanofibre Substrate

The processes of the present invention involve a grafting step (step (ii)) which involves grafting one or more neutral polymer chains from the substrate provided in step (i).

Grafting one or more neutral polymer chains from a substrate typically comprises growing one or more polymer chains from one or more functional groups present on the substrate, optionally in the presence of one or more catalysts. Thus, typically, the substrate comprises one or more functional groups, preferably one or more functional groups from which a polymer chain may be grown. Growing a polymer chain from the one or more functional groups means building up a polymer at the one or more functional groups from individual monomer building blocks.

The grafting step typically therefore involves growing polymer chains directly from the substrate, rather than bonding preformed polymer chains to the substrate. Thus, as the polymerisation progresses, individual monomers are added to the ends of growing polymer chains that are anchored distally to the substrate.

Growth of the polymer chains directly from the substrate enables control over the structure of the polymer coating, particularly using a polymerisation strategy whereby the polymers all grow simultaneously at a uniform rate. This enables formation of a dense and well-defined polymer coating layer.

In the present invention, the grafting step comprises reacting a plurality of compounds of formula

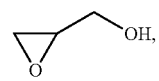

and/or its enantiomers, and/or its derivatives of formula (I) and/or enantiomers and/or diastereomers thereof:

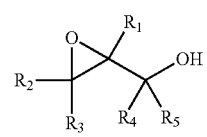

(I)

with one or more functional groups present on the nanofibre substrate, wherein $R_1$, $R_2$, $R_3$, $R_4$ and $R_5$ may be the same or different, and are chosen from H, halo, $C_1$-$C_4$ alkyl, or $C_1$-$C_4$ alkoxy provided that at least one of $R_1$, $R_2$, $R_3$, $R_4$ or $R_5$ is not hydrogen. Typically, therefore, only one type of polymer is grafted to the substrate. However, in other embodiments, more than one type of polymer may be grafted to the substrate.

Typically, $R_1$, $R_2$, $R_3$, $R_4$ and $R_5$ may be the same or different, and are chosen from fluoro, chloro, bromo, methyl or ethyl.

Thus, in compounds of formula (I):

$R_1$ is H, halo, $C_1$-$C_4$ alkyl, or $C_1$-$C_4$ alkoxy, preferably H, fluoro, chloro, bromo, methyl or ethyl;

$R_2$ is H, halo, $C_1$-$C_4$ alkyl, or $C_1$-$C_4$ alkoxy, preferably H, fluoro, chloro, bromo, methyl or ethyl;

$R_3$ is H, halo, $C_1$-$C_4$ alkyl, or $C_1$-$C_4$ alkoxy, preferably H, fluoro, chloro, bromo, methyl or ethyl;

$R_4$ is H, halo, $C_1$-$C_4$ alkyl, or $C_1$-$C_4$ alkoxy, preferably H, fluoro, chloro, bromo, methyl or ethyl; and $R_5$ is H, halo, $C_1$-$C_4$ alkyl, or $C_1$-$C_4$ alkoxy, preferably H, fluoro, chloro, bromo, methyl or ethyl.

Typically, when the grafting step (ii) involves reacting the substrate having or more functional groups from which polymers may be grown with a plurality of compounds of formula (I) and/or enantiomers thereof, at least one of $R_1$, $R_2$, $R_3$, $R_4$ and $R_5$ is hydrogen. In this case, preferably at least two of $R_1$, $R_2$, $R_3$, $R_4$ and $R_5$ are hydrogen. More preferably, at least three of $R_1$, $R_2$, $R_3$, $R_4$ and $R_5$ are hydrogen. Even more preferably, four of $R_1$, $R_2$, $R_3$, $R_4$ and $R_5$ are hydrogen. Preferably, $R_1$ is hydrogen, and at least one of $R_2$ and $R_3$ is hydrogen. Alternatively $R_2$ and $R_3$ are hydrogen. Yet more preferably, $R_1$, $R_2$, and $R_3$ are hydrogen.

Most preferably, the grafting step (ii) involves reacting the substrate having one or more functional groups from which polymers may be grown with a plurality of compounds of formula

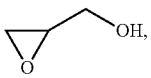

and/or its enantiomers.

In embodiments where the substrate is formed from nanofibres formed from different polymers, each different kind of polymer nanofibre may be grafted with a different polymer in the grafting step. That could, for instance, result from different functional groups being present on the different polymer nanofibres. Alternatively, the same polymer may be grafted to each of the different kinds of polymer nanofibre in the substrate.

Typical functional groups include hydroxyl, amino and carboxyl groups. In the case where the substrate is formed of one or more cellulose or cellulose acetate nanofibres, the functional groups are typically hydroxyl groups.

Typically, the substrate is treated between steps (i) and (ii) to introduce the one or more functional groups, or the substrate is treated between steps (i) and (ii) to deprotect or activate any functional groups on the substrate, or the substrate is treated between steps (i) and (ii) to increase the number/density of functional groups on the substrate. Preferably, the substrate is treated between steps (i) and (ii) to introduce the one or more functional groups, or to deprotect or activate any functional groups on the substrate. More preferably, the substrate is treated between steps (i) and (ii) to deprotect or activate any functional groups on the substrate. Even more preferably, the substrate is treated between steps (i) and (ii) to deprotect any functional groups on the substrate.

However, in alternative embodiments, there is no additional treating step between steps (i) and (ii). In these embodiments, typically, the grafting step (ii) is carried out under conditions which additionally, in the same step, introduce the one or more functional groups, or deprotect or activate any functional groups on the substrate, or increase the number/density of functional groups on the substrate. Preferably, the grafting step (ii) is carried out under conditions which additionally, in the same step, introduce the one or more functional groups, or deprotect or activate any functional groups on the substrate. More preferably, the grafting step (ii) is carried out under conditions which additionally, in the same step, deprotect or activate any functional groups on the substrate. Even more preferably, the grafting step (ii) is carried out under conditions which additionally, in the same step, deprotect any functional groups on the substrate.

In a particularly preferred embodiment, the functional groups are hydroxyl groups. In this particularly preferred embodiment, the grafting step (ii) is typically carried out under conditions which additionally, in the same step, deprotect the hydroxyl groups on the substrate.

Deprotection of the functional groups is typically effected so that the functional groups can have one or more polymer chains grown from them.

For instance, when the chromatography medium is a cellulose chromatography medium, typically a cellulose acetate substrate is provided and, prior to the grafting step, the cellulose acetate is treated to convert it to cellulose. This involves the deprotection of acetylated hydroxyl groups to give hydroxyl groups. Conversion of cellulose acetate to cellulose is typically effected using aqueous alkali, preferably NaOH in water:ethanol, more preferably water:ethanol 2:1, for a period of greater than 12 hrs, for example from 12 to 36 hours.

Alternatively, when the chromatography medium is a cellulose chromatography medium, a cellulose acetate substrate is provided and treated in the grafting step (ii) under conditions in which both the cellulose acetate is converted to cellulose, and the cellulose subsequently reacts with a plurality of compounds of formula

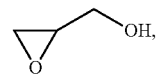

and/or its enantiomers, and/or its derivatives of formula (I) and/or enantiomers and/or diastereomers thereof to generate the grafted polymer chains. In such embodiments, the grafting step (ii) is typically effected in the presence of aqueous alkali, preferably NaOH or KOH, more preferably KOH, in water or water:ethanol, preferably in water, for a period of 4-6 hours.

When the chromatography medium is a cellulose chromatography medium, the present invention typically provides a process for preparing a functionalised cellulose chromatography medium, which process comprises (i) providing a substrate formed of one or more cellulose acetate nanofibres, treating the cellulose acetate to convert it to cellulose, (ii) grafting one or more neutral polymer chains from the resultant cellulose substrate, and (iii) contacting the grafted product with a reagent which functionalises the product of step (ii) as a chromatography medium.

When the chromatography medium is a cellulose chromatography medium, the present invention alternatively provides a process for preparing a functionalised cellulose chromatography medium, which process comprises (i) providing a substrate formed of one or more cellulose acetate nanofibres, (ii) subjecting the substrate to conditions under which both the cellulose acetate is converted to cellulose and, subsequently, one or more neutral polymer chains are grafted onto the resultant cellulose substrate, and (iii) contacting the grafted product with a reagent which functionalises the product of step (ii) as a chromatography medium.

Activation of functional groups is discussed below in the context of step (iii) of the claimed process. That discussion applies equally to activation of functional groups for step (ii) of the claimed process.

Methods for increasing the number and/or density of functional groups on the substrate will be known to the skilled person.

When the one or more functional groups are introduced to the substrate, the substrate is treated between steps (i) and (ii) in a further step (i-a) of modifying a functional group present on the substrate to introduce a functional group from which one or more polymer chains may be grown followed by the step (ii) of growing polymer chains from the thus-modified substrate. Step (i-a) may involve a single step or multiple steps that together modify the functional group present on the substrate to a functional group from which one or more polymer chains may be grown.

In embodiments involving glycidol polymerisation, the substrate is typically treated between steps (i) and (ii) to deprotect any functional groups on the substrate.

Also described herein are comparative processes involving ATRP and RAFT polymerisation in the grafting step. In these processes, the substrate is typically treated between steps (i) and (ii) to modify functional groups present on the substrate to functional groups from which one or more polymer chains may be grown. Prior to this step, the substrate may also be treated to deprotect any functional groups on the substrate.

In processes involving ATRP polymerisation, typically hydroxyl groups on the substrate are modified to introduce alkyl halide or aryl halide groups. Typically an alkyl halide is an alkyl fluoride, alkyl chloride, alkyl bromide or an alkyl iodide. Alkyl bromides are preferred. Tertiary alkyl halides are more preferred. Tertiary alkyl bromides are even more preferred.

The one or more polymer chains grafted to the substrate are neutral. The polymer chains do not contain any groups that would be considered charged groups by a person skilled in the art, e.g. the sort of charged groups discussed below. Typically, the polymer chains grafted to the substrate in step (ii) do not contain any charged groups as defined herein.

Neutrality of a polymer can be assessed by whether the polymer contains any groups which would be ionisable, i.e. protonated or deprotonated, at essentially neutral pH, e.g. pH 6-8, typically pH 6.5-7.5, usually pH 6.75-7.25, or about pH 7. Typically, a neutral polymer contains substantially no acidic or basic centres, i.e. substantially no functional groups that are protonated or deprotonated at pH 6-8, typically pH 6.5-7.5, usually pH 6.75-7.25, or about pH 7. This can be determined by a skilled person by assays typical in the art. Typical procedures for the assessment of acidity and basicity, along with the theoretical aspects thereof are discussed in "Acidity and basicity of solids: Theory, assessment and utility" Editors J. Fraisard and L. Petrakis, NATO ASI Series C, volume 444, Kluwer Academic Publishers, Dordrecht, Boston and London, 1994, especially pp. 513, the entirety of which is incorporated herein by reference. As used here, substantially means fewer than 1 mol %, preferably fewer than 0.1 mol %, even more preferably fewer than 0.01 mol %, or even fewer than 0.001 mol %.

As mentioned above, the grafting step (ii) involves reacting the substrate having one or more functional groups from which polymers may be grown with a plurality of compounds of formula

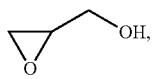

and/or its enantiomers, and/or its derivatives of formula (I) and/or enantiomers and/or diastereomers thereof:

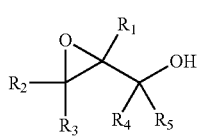

(I)

wherein $R_1$, $R_2$, $R_3$, $R_4$ and $R_5$ may be the same or different, and are chosen from H, halo, $C_1$-$C_4$ alkyl, or $C_1$-$C_4$ alkoxy provided that at least one of $R_1$, $R_2$, $R_3$, $R_4$ or $R_5$ is not hydrogen;
using a method of polymerisation known as glycidol polymerisation. Thus, the growth of polymer chains is carried out using glycidol polymerisation.

Typically, $R_1$, $R_2$, $R_3$, $R_4$ and $R_5$ may be the same or different, and are chosen from fluoro, chloro, bromo, methyl or ethyl.

Thus, in compounds of formula (I):
$R_1$ is H, halo, $C_1$-$C_4$ alkyl, or $C_1$-$C_4$ alkoxy, preferably H, fluoro, chloro, bromo, methyl or ethyl;
$R_2$ is H, halo, $C_1$-$C_4$ alkyl, or $C_1$-$C_4$ alkoxy, preferably H, fluoro, chloro, bromo, methyl or ethyl;
$R_3$ is H, halo, $C_1$-$C_4$ alkyl, or $C_1$-$C_4$ alkoxy, preferably H, fluoro, chloro, bromo, methyl or ethyl;
$R_4$ is H, halo, $C_1$-$C_4$ alkyl, or $C_1$-$C_4$ alkoxy, preferably H, fluoro, chloro, bromo, methyl or ethyl; and
$R_5$ is H, halo, $C_1$-$C_4$ alkyl, or $C_1$-$C_4$ alkoxy, preferably H, fluoro, chloro, bromo, methyl or ethyl.

Typically, when the grafting step (ii) involves reacting the substrate having or more functional groups from which polymers may be grown with a plurality of compounds of formula (I) and/or enantiomers thereof, at least one of $R_1$, $R_2$, $R_3$, $R_4$ and $R_5$ is hydrogen. In this case, preferably at least two of $R_1$, $R_2$, $R_3$, $R_4$ and $R_5$ are hydrogen. More preferably, at least three of $R_1$, $R_2$, $R_3$, $R_4$ and $R_5$ are hydrogen. Even more preferably, four of $R_1$, $R_2$, $R_3$, $R_4$ and $R_5$ are hydrogen. Preferably, $R_1$ is hydrogen, and at least one of $R_2$ and $R_3$ is hydrogen. Alternatively $R_2$ and $R_3$ are hydrogen. Yet more preferably, $R_1$, $R_2$, and $R_3$ are hydrogen.

Most preferably, the grafting step (ii) involves reacting the substrate having one or more functional groups from which polymers may be grown with a plurality of compounds of formula

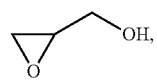

and/or its enantiomers.

Glycidol polymerisation is a technique known to the person skilled in the art. Glycidol polymerisation does not typically require the presence of a catalyst. However, the polymerisation may optionally be carried out in the presence of one or more appropriate catalysts. In such embodiments, typically a chemical or biological catalyst is used. Glycidol polymerisation is typically carried out in an aqueous environment. Typically, glycidol polymerisation is carried out at room temperature. Typically, glycidol polymerisation is carried out under mildly alkaline conditions. Typically, glycidol polymerisation is carried out for greater than around 5 hrs, preferably greater than around 10 hrs, more preferably greater than around 15 hrs, for instance around 16 hrs. Following glycidol polymerisation, typically the grafted product is washed in water followed by mild acid.

Glycidol polymerisation involves polymerising glycidol and/or a glycidol derivative of formula (I) from one or more functional groups as defined herein present on the substrate. Typically, those functional groups are hydroxyl groups. Thus, typically, step (ii) of the claimed process comprises reacting a plurality of compounds of formula

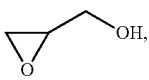

and its enantiomers, and/or its derivatives of formula (I) and/or enantiomers and/or diastereomers thereof, with one or more hydroxyl groups present on the nanofibre substrate. Preferably, step (ii) of the claimed process comprises reacting a plurality of compounds of formula

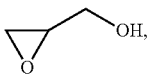

and its enantiomers with one or more hydroxyl groups present on the nanofibre substrate.

Glycidol polymerisation typically results in one or more poly-glycerol chains.

In an embodiment, the present invention therefore provides a process for preparing a functionalised polymeric chromatography medium, which process comprises
(i) providing a substrate formed of one or more polymer nanofibres,
(ii) grafting one or more neutral polymer chains from the substrate, and
(iii) contacting the grafted product with a reagent which functionalises the product of step (ii) as a chromatography medium,
wherein growing polymer chains comprises polymerising glycidol and/or a glycidol derivative of formula (I), preferably glycidol, from one or more functional groups present on the substrate.

In an embodiment, the present invention therefore also provides a process for preparing a functionalised polymeric chromatography medium, which process comprises
(i) providing a substrate formed of one or more polymer nanofibres,
(ii) grafting one or more neutral polymer chains from the substrate, and
(iii) contacting the grafted product with a reagent which functionalises the product of step (ii) as a chromatography medium,
wherein the one or more polymer chains are one or more poly-glycerol chains.

Glycidol polymerisation inevitably results in branching of the polymer chain, yielding a "bush" structure. Thus, typically, one or more of the polymer chains is branched.

Another polymerisation method well known to the person skilled in the art is controlled radical polymerisation (CRP). Controlled radical polymerisation is a term well known to the person skilled in the art and typically refers to free radical addition polymerization of monomers wherein there is a degree of control of molecular weight of the growing polymer with respect to time. Examples of CRPs include atom transfer radical polymerisation (ATRP), atom generated by electron transfer (AGET) ATRP, and reversible addition-fragmentation chain transfer (RAFT). Polymerisation methodologies are not exclusively defined as CRPs but may include free radical polymerisation (FRP) and ring opening metathesis polymerisation (ROMP).

ATRP may be carried out in an aqueous environment or optionally in a mixture of water and another solvent, which may be, for example, methanol, DMSO, THF, DMF or NMP. ATRP polymerisation is preferably carried out under substantially oxygen free conditions. Typically, ATRP is carried out at room temperature. Typically, after ATRP is carried out, the resultant material is washed with water.

Catalysts for use in ATRP polymerisation are typically transition metals or transition metal salts complexed with one or more ligands. As used herein, a ligand is a compound that co-ordinates to a metal ion (usually a transition metal ion). Suitable transition metals include copper, cobalt, molybdenum, rhodium, osmium, ruthenium, palladium, nickel and rhenium. Copper is preferred. Examples of suitable ligands for copper coordinating catalysts include 2,2'-bipyridine (bpy), 4,4'-di(5-nonyl)-2,2-bipyridine (dNbpy), N,N,N',N'-tetramethylethylenediamine (TMEDA), N-propyl(2-pyridyl)methanimine (NPrPMI), 2,2':6',2''-terpyridine (tpy), 4,4',4''-tris(5-nonyl)-2,2':6',2''-terpyridine (tNtpy), N,N,N',N'',N''-pentamethyldiethylenetriamine (PMDETA), N,N-bis(2-pyridylmethyl)octylamine (BPMOA), 1,1,4,7,10,10-hexamethyltriethylenetetramine (HMTETA), tris[2-(dimethylamino)ethyl]amine (Me6TREN), tris[(2-pyridyl)methyl]amine (TPMA) and 1,4,8,11-tetraaza-1,4,8,11-tetramethylcyclotetradecane (Me4CYCLAM).

Use of appropriate monomers and, where applicable, chain transfer agents, may enable branching of the polymers to be induced in CRP methods at the growing ends of the polymer chains, affording the possibility of bush type structures. In other cases, branching is less preferred and an essentially unbranched "brush" polymer structure may be formed.

ATRP polymerisation may be controlled so as to give essentially linear polymeric chains or to give a degree of branching. Substantially unbranched polymers yield a polymer "brush" structure.

ATRP polymerisation may employ one or more different types of monomer, wherein a monomer is any individual unit used to form the polymer. The monomers each include one or more polymerisable groups and are typically selected from monofunctional monomers and difunctional monomers. The polymerisable group typically comprises a C=C double bond.

Examples of suitable monofunctional monomers are methacrylatesandmethacrylamides, for instance N-[3-(dimethylamino)propyl]methacrylamide. Other typical methacrylates and methacrylamides include 2-hydroxypropyl methacrylamide (HPMA) and hydroxyethylmethacrylate (HEMA).

Difunctional monomers, for example dimethacrylates or divinylsulfone, can be used to introduce branching and/or cross-linking in the ATRP polymerisation.

Functionalisation of Grafted Products

The processes of the present invention involve a functionalisation step (step (iii)) of the grafted product which functionalises that product as a chromatography medium, for instance by introducing one or more ligand groups onto the grafted product. This step involves contacting the grafted product with a reagent which functionalises the grafted product as a chromatography medium by introducing one or more ligand groups onto the grafted product.

For the avoidance of doubt, step (iii) may involve a single step or multiple steps that together functionalise the product of step (ii) as a chromatography medium.

The reagent typically functionalises the chromatography medium by introducing one or more ligand groups which render the functionalised product comprising the one or more ligand groups suitable for use as a chromatography medium. The one or more ligand groups introduced will depend on the particular chromatography technique for which the medium is to be used. The ligand groups are the groups introduced onto the grafted product that make it suitable for use as a chromatography medium. Suitable ligand groups and reagents are discussed further below.

In some embodiments, the grafted product is functionalised with only one type of ligand group. In other embodiments, the grafted product is functionalised with two or more types of ligand group. Thus, step (iii) of the claimed process involves contacting the grafted product with a reagent which functionalises the product of step (ii) as a chromatography medium by introducing one or more ligand groups, which may be the same or different, onto the grafted product.

In embodiments where the substrate comprises one or more polymer nanofibres formed from different polymers, each different kind of polymer nanofibre may be functionalised (after grafting) with one or more ligand groups, which may be the same or different.

In embodiments where more than one type of polymer may be grafted to the substrate, each polymer graft may be functionalised with one or more ligand groups, which may be the same or different.

Although the present invention envisages processes involving only a single treatment with a reagent, processes involving multiple functionalising steps may also be used. Such embodiments involve functionalisation by contacting the grafted product in a batchwise fashion two or more times with a reagent. Batchwise functionalisation means that the grafted product is reacted with a reagent to functionalise it, that reaction is then stopped and the resultant (partially) functionalised material reacted with a separate batch of reagent. Reacting in a batchwise fashion does not simply refer to adding more portions of reagent to a reaction vessel, for instance.

Batchwise functionalisation is typically carried out from two to ten times, i.e. 2, 3, 4, 5, 6, 7, 8, 9 or 10 times.

Preferred processing conditions for batchwise functionalisation can be found in WO-A-2015/052460 and WO-A-2015/052465, the entirety of which are incorporated herein by reference.

In certain circumstances, contacting with a reagent may comprise placing the grafted product in a holder, and causing a reagent to flow through the holder so that the reagent flows in contact with the grafted product which functionalises the grafted product as a chromatography medium. Functionalising material in this manner may in certain circumstances be more efficient than simply contacting the grafted product with the reagent, in a flask or beaker for example.

Preferred processing conditions for flow functionalisation can be found in WO-A-2015/052460 and WO-A-2015/052465, the entirety of which are incorporated herein by reference.

The reagent functionalises the grafted product to yield a chromatography medium, specifically a functionalised chromatography medium. Typically, the reagent functionalises the grafted product so that it is suitable for use in an ion exchange, affinity capture or hydrophobic chromatography method. Thus, contacting with the reagent yields a chromatography medium which is functionalised with one or more ligand groups, i.e one or more moieties which are negatively charged, one or more moieties which are positively charged, one or more proteins, mimetic or synthetic ligands that mimic the action of protein ligands, peptides, antibodies or fragments thereof, dyes, histidine, groups containing a metal cation, or hydrophobic groups. 2-chloro-N,N-diethylamine hydrochloride (DEACH) and glycidyltrimethylammonium are preferred as the reagent, particularly when the functionalised chromatography medium is for use in an anion exchange chromatography method. Other preferred reagents are 1,4-butanesulfone, sodium chloroacetate, TEMPO followed by sodium perchlorate, or allyl gycidyl ether followed by sodium disulphite, particularly when the funtionalised chromatography medium is for use in a cation exchange chromatography method. Another preferred reagent is $NaIO_4$, divinylsulfone followed by Protein A, allyl glycidyl ether followed firstly by a halohydrin-forming reagent (e.g. N-bromosuccinamide) and subsequently by Protein A, or allyl glycidyl ether followed firstly by an epoxide-forming reagent and subsequently by Protein A, particularly when the functionalised chromatography medium is for use in an affinity chromatography method. Another preferred reagent is styrene oxide, particularly when the functionalised chromatography medium is for use in a hydrophobic chromatography method.

Typically, the reagent is gycidyltrimethylammonium, 1,4-butanesulfone, sodium chloroacetate, $NaIO_4$ followed by Protein A, divinylsulfone followed by Protein A, allyl glycidyl ether followed firstly by a halohydrin-forming reagent (e.g. N-bromosuccinamide) and subsequently by Protein A, or allyl glycidyl ether followed firstly by an epoxide-forming reagent and subsequently by Protein A. Preferably, the reagent is divinylsulfone followed by Protein A, or allyl glycidyl ether followed firstly by a halohydrin-forming reagent (e.g. N-bromosuccinamide) and subsequently by Protein A.

Thus, in preferred embodiments, the present invention provides a process for preparing a functionalised polymeric chromatography medium, wherein the functionalisation step (iii) involves multiple steps that together functionalise the product of step (ii) as a chromatography medium.

In a particularly preferred embodiment, the present invention provides a process for preparing a functionalised polymeric chromatography medium, wherein in the functionalisation step (iii):

(a) the grafted product is first contacted with a reagent selected from the group selected from divinyl sulfone, allyl glycidyl ether, and combinations thereof;

(b) the product of step (a) is optionally treated with a halohydrin-forming reagent or an epoxide-forming reagent, preferably a halohydrin-forming reagent; and (c) the product of step (b) is contacted with Protein A.

In this particularly preferred embodiment, if the grafted product is first contacted in step (a) with divinyl sulfone, the product of step (a) is typically not treated with a halohydrin-forming reagent or an epoxide-forming reagent. Thus, in some embodiments, in the functionalisation step (iii), the grafted product is first contacted with divinyl sulfone, and the product of this step is subsequently contacted with Protein A. In this particularly preferred embodiment, if the grafted product is first contacted in step (a) with allyl glycidyl ether, the product of step (a) is subsequently treated with a halohydrin-forming reagent or an epoxide-forming reagent, preferably a halohydrin-forming reagent, in step (b). Thus, in some embodiments, in the functionalisation step (iii), the grafted product is first contacted with allyl glycidyl ether, and the product of this step is treated with a halohydrin-forming reagent, and then the product of this step is subsequently contacted with Protein A.

In another particularly preferred embodiment, the present invention provides a process for preparing a functionalised polymeric chromatography medium, wherein in the functionalisation step (iii):

(a) the grafted product is contacted with a reagent selected from the group selected from divinyl sulfone, allyl glycidyl ether, and combinations thereof;

(b) the product of step (a) is optionally treated with a halohydrin-forming reagent or an epoxide-forming reagent, preferably a halohydrin-forming reagent; and (c) the product of step (b) is contacted with Protein A.

In this particularly preferred embodiment, if the grafted product is first contacted in step (a) with divinyl sulfone, the product of step (a) is typically not treated with a halohydrin-forming reagent or an epoxide-forming reagent. Thus, in some embodiments, in the functionalisation step (iii), the grafted product is first contacted with divinyl sulfone, and the product of this step is subsequently contacted with Protein A. In this particularly preferred embodiment, if the grafted product is first contacted in step (a) with allyl glycidyl ether, the product of step (a) is subsequently treated with a halohydrin-forming reagent or an epoxide-forming reagent, preferably a halohydrin-forming reagent, in step (b). Thus, in some embodiments, in the functionalisation step (iii), the grafted product is contacted with allyl glycidyl ether, and the product of this step is treated with a halohydrin-forming reagent, and then the product of this step is subsequently contacted with Protein A.

Chromatography Media and Methods

The products of the process of the present invention are functionalised chromatography media, i.e. chromatography media that have had polymer grafted from them and which have then been functionalised to render them suitable for use in one or more chromatography methods by introducing one or more ligand groups onto the grafted products.

Specific chemical functionalisations are discussed in more detail below. In general terms, such chemical functionalisation changes the chemical and/or physical properties of the functionalised chromatography medium by introducing one or more charged groups. This in turn affects how the functionalised chromatography medium behaves when used in a chromatography method. The modifications may, for example, change the polarity, hydrophobicity or biological binding properties of the functionalised chromatography medium compared to its unfunctionalised form. The modifications may, in certain circumstances, change more than one of the polarity, hydrophobicity or biological binding properties of the functionalised chromatography medium compared to its unfunctionalised form. In one embodiment, the modification changes the polarity and hydrophobicity of the functionalised chromatography medium compared to its unfunctionalised form.

The functionalised chromatography media are typically in the form of membranes. Such membranes are suitable for use in membrane chromatography methods. Membrane chromatography methods are well known to the person skilled in the art and are discussed in "Membrane Processes in Biotechnologies and Pharmaceutics" ed. Catherine Charcosset, Elsevier, 2012, the entirety of which is incorporated herein by reference.

Typically, the functionalised polymer chromatography media are suitable for use in chromatography methods chosen from ion exchange chromatography, affinity capture chromatography, hydrophobic chromatography and mixed mode chromatography. In certain circumstances, the chromatography method operates in "mixed mode", i.e. utilising more than one form of interaction, i.e. ion exchange, affinity capture and hydrophobic interaction. Typically, such "mixed mode" chromatography involves ion exchange (ionic) and hydrophobic interactions. Preferably, the functionalised polymer chromatography media are suitable for use in chromatography methods chosen from ion exchange chromatography, affinity capture chromatography, and hydrophobic chromatography, preferably ion exchange chromatography and affinity capture chromatography. In operation, such chromatography methods involve passing a mobile phase containing a desired molecule over an adsorbent phase, here the functionalised chromatography medium. The adsorbent phase is typically chosen such that the desired molecule is retained on it in preference to other components also present in the mobile phase.

Typically, the polymer chromatography medium is functionalised with DEAE, Q, SP, CM, Protein A, phenyl, or MEP groups, for instance DEAE, Q, SP, CM or Protein A groups. Generally, the polymer is cellulose and the chromatography medium is functionalised with DEAE, Q, SP, CM, Protein A, phenyl, or MEP groups, for instance DEAE, Q, SP, CM or Protein A groups. Thus, the functionalised chromatography medium may be cellulose derivatised with DEAE, Q, SP, CM, Protein A, phenyl, or MEP groups, for instance DEAE, Q, SP, CM or Protein A groups.

In a preferred embodiment, the polymer chromatography medium is functionalised with Protein A.

Ion exchange chromatography is a technique for separating molecules, typically ions or polar molecules, based on their ionic charge. Functionalised chromatography media for use in such methods therefore contain one or more moieties which are positively or negatively charged. Positive and/or negative charges in functionalised chromatography media are usually balanced with one or more counter ions. Ion exchange chromatography involves one or more of cation exchange chromatography and anion exchange chromatography.

Functionalised chromatography media for use in cation exchange chromatography contain one or more moieties which are negatively charged. Typical negatively charged moieties include one or more carboxylate, sulphonate or phosphonate groups, or mixtures thereof, i.e. the moieties typically contain one or more $-COO^-$, $-SO_3^-$, or $-P(OH)_2O^-$ groups, or mixtures thereof. Typical functionalised chromatography media for use in cation exchange chromatography contain one or more $-O-CH_2COO^-$, $-CH_2COO^-$, $-SO_3^-$, $-CH_2CH_2CH_2SO_3^-$, $-CH_2CH_2SO_3^-$, or $-P(OH)_2O^-$ moieties.

Functionalised chromatography media for use in anion exchange chromatography contain one or more moieties which are positively charged. Typical positively charged moieties include one or more quaternary amine groups. Typical functionalised chromatography media for use in anion exchange chromatography contain one or more $-N^+(CH_3)_3$, $-N^+(C_2H_5)H$, $-CH_2CH_2N^+(C_2H_5)H$, $-CH_2CH_2N^+(C_2H_5)_2(CH_2CH(OH)CH_3)$, $-O-CH_2CH_2-N^+(CH_3)_3$, $-CH_2CH_2N^+(CH_3)_3$, or $-CH_2CH_2N^+(CH_3)_2H$ moieties.

For the avoidance of doubt, by "charged group" is meant a group that comprises a moiety that is ionised so that it bears a positive or negative charge, i.e. a "charged group" comprises an anionic or cationic moiety. A charged group is a particular example of a ligand group.

Typically, the one or more charged groups comprise one or more carboxylate ($-COO^-$), sulphonate ($-SO_3^-$), or phosphonate groups ($-P(OH)_2O^-$) groups, or quaternary amine groups, or mixtures thereof. Typically, the one or more charged groups comprise all anionic groups or all cationic groups, however in certain circumstances mixtures of anionic and cationic groups are envisaged. Typically, only one type of anionic group is used, but mixtures may also be used. Typically, only one type of cationic group is used, but mixtures may also be used.

Representative charged groups include $-O-CH_2COO^-$, $-CH_2COO^-$, $-SO_3^-$, $-CH_2CH_2CH_2SO_3^-$, —CH$_2$CH$_2$SO$_3^-$, —P(OH)$_2$O$^-$, —N$^+$(CH$_3$)$_3$, —N$^+$(C$_2$H$_5$)H, —CH$_2$CH$_2$N$^+$(C$_2$H$_5$)H, —CH$_2$CH$_2$N$^+$(C$_2$H$_5$)$_2$(CH$_2$CH(OH)CH$_3$), —O—CH$_2$CH$_2$—N$^+$(CH$_3$)$_3$, —CH$_2$CH$_2$N$^+$(CH$_3$)$_3$, and —CH$_2$CH$_2$N$^+$(CH$_3$)$_2$H moieties.

Typical charged groups include DEAE, Q, SP, and CM groups. Typically, the functionalised polymer chromatography medium is functionalised with DEAE, Q, SP, or CM groups. Thus, the functionalised chromatography medium may be cellulose derivatised with DEAE, Q, SP, or CM groups.

Affinity capture chromatography is a technique for separating molecules based on their affinity to particular ligands, usually but not always biological ligands. This method may, for example, rely on the attractive forces between antibodies and antigens or enzymes and substrates. Functionalised chromatography media for use in affinity capture chromatography typically contain one or more moieties chosen from one or more proteins, peptides, antibodies or fragments thereof, dyes, histidine, or groups containing a metal cation. Thus, the one or more ligand group may comprise one or more such moieties. Alternatively, functionalised chromatography media for use in affinity capture chromatography may contain mimetic or synthetic ligands that mimic the action of protein ligands.

Typical proteins for use in affinity capture chromatography are well known to the person skilled in the art and include Protein A, Protein G and Protein L. Protein A is preferred.

Protein A is a protein well known to the skilled person. As used herein, references to "Protein A" embrace recombinant Protein A (which may have an altered sequence compared to Protein A found in *Staphylococcus aureus*) and tagged Protein A (as described in EP-B-0873353 and U.S. Pat. No. 6,399,750, the entirety of which are incorporated herein by reference). Protein A may be a modified variant of Protein A, for instance cysteine modified variants of Protein A.

Typical antibodies and fragments thereof for use in affinity capture chromatography are well known to the person skilled in the art and include IgG.

Typical dyes for use in affinity capture chromatography are well known to the person skilled in the art and include Yellow HE-4R, Red HE-3B and Cibacron Blue F3G.

Typical groups containing metal cations for use in affinity capture chromatography are well known to the person skilled in the art. Such groups typically contain a chelating agent to immobilize metal cations. The metal cation is typically chosen from copper, nickel, zinc and cobalt cations, preferably Cu$^{2+}$, Ni$^{2+}$, Zn$^{2+}$ and Co$^{2+}$.

Hydrophobic interaction chromatography is a technique for separating molecules based on their hydrophobicity. Functionalised chromatography media for use in such methods therefore contain one or more moieties which contain one or more hydrophobic groups. Typical hydrophobic groups include propyl, butyl, phenyl, and octyl groups.

Mixed mode (or multimodal) chromatography is a technique for separating molecules based on two or more characteristics, typically hydrophobicity and ionic charge. This may involve a combination of hydrophobicity and anionic properties, or a combination of hydrophobicity and cationic properties. Functionalised chromatography media for use in such methods therefore typically contain one or more moieties which are positively or negatively charged, typically as defined above, and which contain one or more hydrophobic groups, typically as defined above. Positive and/or negative charges in functionalised chromatography media are usually balanced with one or more counter ions. Functionalised chromatography media for use in such methods may also contain one or more hydrophobic groups which are ionisable, for use in so-called Hydrophobic Charge Induction Chromatography (HCIC). Thus, in one embodiment, mixed mode chromatography is Hydrophobic Charge Induction Chromatography. Suitable groups for use in such methods are 4-mercapto-ethyl-pyridine (MEP) groups and octylamine groups.

Functionalised chromatography media for use in mixed mode chromatography methods which involve a combination of hydrophobic and anionic interactions contain one or more moieties which are positively charged, typically as defined above, and one or more hydrophobic groups, typically as defined above. Suitable groups for use in such methods are N-benzyl methyl ethanolamine groups and N-benzoyl-homocysteine groups. Functionalised chromatography media for use in mixed mode chromatography methods which involve a combination of hydrophobic and cationic interactions contain one or more moieties which are negatively charged, typically as defined above, and one or more hydrophobic groups, typically as defined above. Suitable groups for use in such methods are N-benzoyl-homocysteine groups.

The processes claimed in the present invention for preparing functionalised chromatography media typically involve in step (iii) introducing one or more ligand groups into the grafted product such that the resultant functionalised product comprising the one or more ligand groups is suitable for use as a chromatography medium in a chromatography method. Typical moieties, media, reagents and methods are as defined above. The one or more ligand groups are introduced by reacting a suitable reagent with one or more functional groups contained on the grafted product. Typical functional groups include hydroxyl, amino, halogen and carboxyl groups. Since step (ii) of the method involves glycidol polymerisation, the functional groups are typically hydroxyl groups. Suitable reagents for introducing the one or more ligand groups are discussed elsewhere.

The one or more functional groups may be activated prior to reaction with a reagent. Conventional activation methods known in the art may be employed. Thus, in the case where the functional group is an hydroxyl group, such a group may be activated by treating with carbonyl diimidazole (CDI), bisoxiranes, cyanuric acid, N-hydroxysuccinimide esters (NHS), 2-fluoro-1-methyl pyridinium toluene-4 sulphonate (FMP), NaIO$_4$, divinylsulfone, or allyl glycidyl ether. In the case where the functional group is an amino group, such a group may be activated by treating with epichlorohydrine, glutaraldehyde or epoxide. In the case where the functional group is a carboxyl group, such a group may be activated by treating with CDI or 1-ethyl-3-(3-dimethylaminopropyl)carbodiimide (EDC). In the case where the functional group is a halogen atom, such a group may be activated by treating with divinylsulfone.

A skilled person can choose suitable reagents to introduce particular groups and moieties into particular polymers, for example on the basis of the desired ligand groups and moieties and the functional groups contained in those polymers. Typical reagents include 2-chloro-N,N-diethylamine hydrochloride (DEACH), glycidyltrimethylammonium chloride (GMAC), 1,4-butanesulfone, sodium chloroacetate, NaIO$_4$ followed by Protein A, divinylsulfone followed by Protein A, allyl glycidyl ether followed firstly by a halohydrin-forming reagent and subsequently by Protein A, or allyl glycidyl ether followed firstly by an epoxide-forming reagent and subsequently by Protein A.

Typical halohydrin-forming reagents include an electrophilic source of a halogen and a nucleophilic source of hydroxyl. Thus, typical halohydrin-forming reagents include a diatomic halogen (typically, $Cl_2$, $Br_2$ or $I_2$) in water, N-chlorosuccinamide, N-bromosuccinamide, or N-iodosuccinamide. Typically, a halohydrin-forming reagent generates a halohydrin species from an alkene. The halohydrin-forming reaction may be regioselective to yield predominantly the halohydrin product on which the halogen atom is bonded to the terminal carbon atom of the polymer chain, or it may be regioselective to yield predominantly the halohydrin product on which the hydroxyl group is bonded to the terminal carbon atom of the polymer chain, or it may have low regioselectivity. Preferably, the halohydrin-forming reaction may be regioselective to yield predominantly the halohydrin product on which the halogen atom is bonded to the terminal carbon atom of the polymer chain.

Typical epoxide-forming reagents include peroxyacids (such as meta-chloroperoxybenzoic acid (mcpba)), hydrogen peroxide in the presence of NaOH or $H_2O$, tert-butyl hydroperoxide in the presence of vanadyl acetylacetonate, tert-butyl hydroperoxide in the presence of $Ti(O^iPr)_4$ and diethyltartrate, tert-butyl hydroperoxide in the presence of $Ti(O^iPr)_4$ and diisopropyltartrate, or oxone in the presence of a fructose-derived catalyst and a base.

Typically,
the chromatography method is a cationic exchange method, and the reagent functionalises the chromatography medium with one or more charged groups comprising one or more carboxylate, sulphonate or phosphonate moieties; or the chromatography method is an anionic exchange method, and the reagent functionalises the chromatography medium with one or more charged groups comprising one or more quaternary amino or diethylaminemoieties;

the chromatography method is an affinity capture chromatography method, and the reagent functionalises the chromatography medium with one or more proteins, peptides, antibodies or fragments thereof, dyes, histidine groups, or groups containing a metal cation;

the chromatography method is a hydrophobic interaction chromatography method, and the reagent functionalises the chromatography medium with one or more propyl, butyl, phenyl, or octyl groups; or the chromatography method is a mixed mode chromatography method, and the reagent functionalises the chromatography medium with one or more MEP, octylamine, N-benzyl methyl ethanolamine or N-benzoyl-homocysteine groups.

Particular Embodiments of the Invention

As discussed above, the present invention provides a two-step process for preparing a functionalised polymeric chromatography medium from a polymer nanofibre substrate, the two steps being (i) a polymer grafting step, and (ii) a functionalisation step.

The polymer grafting step typically introduces 500-60,000 µmol/g of polymer to the substrate, preferably 1000-60,000 µmol/g. In some embodiments, the grafting step introduces 1000-2000 µmol/g. In other embodiments, the grafting step introduces 5000-10,000 µmol/g. In yet other embodiments, the grafting step introduces 30,000-60,000 µmol/g. This amount can typically be determined by an assay method measuring the amount of particular functional groups, e.g. hydroxyl groups, added to the substrate by the grafting method. A skilled person will be aware of suitable methods to use to determine the amount of particular functional groups present in a given sample of grafted material.

An increased polymer density can be obtained by using increased amounts or higher concentrations of polymerisation reagents, or by carrying out the reaction at higher temperatures or for longer periods of time.

In the context of glycidol polymerisation, the grafting step typically introduces 500-60,000 µmol/g of glycidol to the grafted product as determined by the —OH density of the grafted product. The —OH density of the grafted product may be determined by a titration method, typically a titration with tetrabutylammonium hydroxide.

An increased —OH density can be obtained by using an increased amount of glycidol or a glycidol derivative having formula (I).

Preferably, the —OH content of a sample of a particular polymer is determined by the following assay:

1) Placing a sample of grafted material on a wetted filter paper, located in Buchner filter funnel and washing with ultrapure water while applying a vacuum to ensure the water washes through the sample;

2) Drying the sample to constant mass in an oven at 60° C. and determining the mass of the sample.

3) Shredding the sample and suspending it in a 50 mL centrifuge tube containing 10 ml of p-toluenesulfonylisocyanate solution (20 mL p-toluenesulfonylisocyanate in 500 ml acetonitrile);

4) Sealing the tube and stirring the mixture with heating (60° C.), in a water bath, for 1 hour;

5) Allowing the tube and its contents to cool to room temperature, quenching carefully with 10 mL ultrapure $H_2O$ before being transferring the mixture to a titration cup and making up to 80 mL with iso-propyl alcohol;

6) Stirring the mixture was stirred for 30 mins at room temperature and then titrating with tetrabutylammonium hydroxide (0.481M solution in methanol) to determine the absolute concentration of hydroxyl groups present.

The —OH concentration (mol/g) of a sample of a particular polymer may be determined by determining the absolute concentration of hydroxyl groups in a sample by the above assay and dividing by the total mass of the dried sample obtained in step (2) of the assay.

Following steps (ii) and (iii), the density of ligand groups introduced in step (iii) of the process of the present invention is typically 100-2,000 µmol/g of functionalised chromatography medium. The density is preferably 300-1,500 µmol/g, more preferably 500-1200 µmol/g. In some embodiments, the density is 100-500 µmol/g. In other embodiments, the density is 1200-2000 µmol/g. Densities much greater than 2,000 µmol/g of functionalised chromatography medium may result in materials that are difficult to use as chromatography media.

The density is typically determined by a titration method to determine the number of moieties in the functionalised material. A skilled person will be aware of suitable methods to use to determine the amount of particular moieties present in a given sample of functionalised material.

In the context of functionalisation with trimethylammonium chloride, the density can be determined as the trimethylammonium chloride density which may be determined by the following assay:

1) Washing 50 mg of material with 100 mL 0.1M HCl solution on a Buchner filter funnel and then with a further 100 mL 0.01M HCl solution;

2) Drying the material in a drying oven at 75° C. to constant mass before tearing into small pieces and placing in a 50 mL centrifuge tube equipped with a small magnetic stir bar;

3) Adding 15 mL deionised water along with approximately 1 mL (added via a teat pipette) potassium chromate solution which causes the mixture to become yellow in colour;

4) Stirring the mixture was vigorously for 20 minutes before being titrating with 0.1M silver nitrate, the endpoint of the titration being identified by a change in colour from clear yellow to misty brown;

5) Calculating the trimethylammonium chloride content (µmol/g) as the number of micromoles of silver nitrate added to reach end point/number of grams of nanofibre material used in the titration.

In the context of functionalisation with sulfonic acid (S) groups, the density can be determined as the sulfonic acid density which may be determined by the following assay:

1) Washing a dried sample of functionalised material with 0.1M HCL and 0.01M HCl;

2) Drying the material in an oven and weighing;

3) Determining the molarity of the material by the amount of NaOH that must be added to reach pH7;

4) Calculating the sulfonic acid (S) content (µmol/g) as the number of micromoles of NaOH added to reach pH7/number of grams of nanofibre material used in the titration.

The two step method of the invention enables a high degree of control over the pressure drop over a sample of the material. This is advantageous, since absolute pressure drop over a chromatography material is a limiting factor at industrial scales. Specifically, the normal operating parameters of most commercial pumps are such that a pressure drop of 2 MPa is the maximum tolerable pressure drop. The present inventors have found that a surprisingly high flowrate of material is possible through materials produced in accordance with the present invention at a pressure drop of 2 MPa. Thus, typically the pressure drop over the functionalised polymeric chromatography medium is less than 2 MPa when a liquid phase is passed through a thickness of 0.05 to 10 mm of the medium at a flow rate of between 1 to 640 membrane volumes per minute. This can be determined using standard means, e.g. an AKTA protein purification system. This is a measure of the resistance to flow of the material.

Typically, the pressure drop is less than 1 MPa, preferably less than 0.5 MPa.

Typically, the flow rate through the medium is between 1 and 60 membrane volumes per minute, preferably between 5 and 40.

The liquid phase passed through the medium is not particularly significant. Typical liquid phases include standard buffers, for instance Tris buffer, preferably 10 mM Tris.

Typically, the liquid phase is passed through a thickness of 0.1 to 5 mm of material.

Preferably, the pressure drop over the functionalised polymeric chromatography medium is less than 1 MPa when Tris buffer is passed through a thickness of 0.1 to 5 mm of the medium at a flow rate of between 1 to 60 membrane volumes per minute.

More preferably, the pressure drop over the functionalised polymeric chromatography medium is less than 0.5 MPa when 10 mM Tris is passed through a thickness of 0.1 to 5 mm of the medium at a flow rate of between 5 to 40 membrane volumes per minute.

The combination of grafting and functionalisation steps allows a material with a high dynamic binding capacity (DBC) to be achieved. Thus, typically, the functionalised chromatography material has a DBC of 10 to 210 mg/mL (10% breakthrough), preferably 20 to 195 mg/mL (10% breakthrough), 30 to 180 mg/mL (10% breakthrough), 40 to 165 mg/mL (10% breakthrough), or 50 to 150 mg/mL (10% breakthrough). For materials where step (ii) has involved glycidol polymerisation, typically the functionalised chromatography material has a DBC of 50-150 mg/mL (10% breakthrough).

The DBC for 10% breakthrough can be determined in accordance with standard means, e.g. using an AKTA Pure system.

DBC for 10% breakthrough is typically determined according to the following assay method:

1) Loading material (For anion exchange material the loading material was 1 mg/mL BSA in 10 mM Tris to pH 8. For cation exchange material the loading material was 1 mg/mL lysozyme in sodium acetate pH 4.7 10 mM.) is passed through functionalised material contained within a holder on an AKTA Pure system (GE Healthcare);

2) material is loaded under a determined membrane volume per minute flowrate (mV/min) until the concentration after the holder outlet exceeded 10% of that loaded as determined by the UV flow cell;

3) Accounting for dead volumes in the system and the holder device the total amount of protein loaded onto the disc at the 10% breakthrough was determined through analysis of the chromatogram in the Unicorn software (GE Healthcare).

The high dynamic binding capacities of and high possible flowrates through the functionalised materials of the invention enable an advantageously high productivity to be achieved. Thus, typically, the productivity of the functionalised polymeric chromatography medium is 50 mg/mL/min to 75,000 mg/mL/min. Preferably, the productivity is 600 mg/ml/min or greater. More preferably, the productivity is 1200 mg/ml/min or greater. Even more preferably, the productivity is 2400 mg/ml/min or greater. The productivity may be 10,000 mg/ml/min or greater or even 15,000 mg/ml/min or greater, or 20,000 mg/ml/min or greater. Productivities of 10,000 mg/ml/min, 15,000 mg/ml/min or 20,000 mg/ml/min or greater are typically achievable using glycidol polymerisation.

As used herein, the productivity of a material is determined by how much material can be loaded onto the adsorbent material, per unit volume of material, per unit time. In practice this is determined as the DBC (10% breakthrough) divided by the residence time of the loading material in the holder. The residence time can, in turn, be determined from the flowrate of material passing through the holder.

As discussed above, the present inventors have investigated thoroughly the relationship between the grafting step (ii) and functionalisation step (iii) and have found that by decoupling these steps from one another highly optimised materials can be produced.

Thus, in certain embodiments, it has been found that the grafting step (ii) has the effect of increasing the dynamic binding capacity (DBC) of the functionalised polymeric chromatography medium. Thus, for two materials of a given density of ligand groups, a material with a higher degree of grafting has been found typically to have a higher DBC. This is particularly the case for materials functionalised with positively charged groups, i.e. where the functionalised chromatography materials are suitable for use in an anionic exchange chromatography method.

Thus, in one embodiment, the present invention provides a process for preparing a functionalised polymeric chromatography medium, which process comprises (i) providing a substrate formed of one or more polymer nanofibres, as defined herein, (ii) grafting one or more neutral polymer chains from the substrate, as defined herein, and (iii) contacting the grafted product with a reagent, as defined herein, which functionalises the product of step (ii) as a chromatography medium, as defined herein, wherein the grafting step (ii) comprises reacting a plurality of compounds of formula

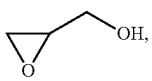

and/or its enantiomers, and/or its derivatives of formula (I) and/or enantiomers and/or diastereomers thereof:

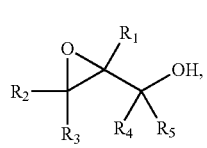

(I)

with one or more functional groups present on the nanofibre substrate, wherein $R_1$, $R_2$, $R_3$, $R_4$ and $R_5$ may be the same or different, and are chosen from H, halo, $C_1$-$C_4$ alkyl, or $C_1$-$C_4$ alkoxy provided that at least one of $R_1$, $R_2$, $R_3$, $R_4$ or $R_5$ is not hydrogen, and has the effect of increasing the DBC of the functionalised polymeric chromatography material.

In other embodiments, usually materials functionalised with negatively charged groups, i.e. where the functionalised chromatography materials are suitable for use in a cationic exchange chromatography method, it has been found that varying the amount of functionalisation reagent used in step (iii) of the claimed method has only a small impact on charge density, but when combined with a grafting step a significant increase in binding capacity can be achieved for the same degree of functionalization. Again, therefore it is clear that it is the combination of the grafting and functionalisation steps that positively impacts DBC.

Typically, the functionalised chromatography medium is a functionalised cellulose chromatography medium and the substrate is formed of one or more cellulose acetate nanofibres, between steps (i) and (ii) the cellulose acetate is treated to convert it to cellulose, the step of grafting one or more neutral polymer chains from the substrate involves glycidol polymerisation, and the grafted product is contacted with a reagent chosen from glycidyltrimethylammonium chloride (GMAC), 1,4-butanesulfone, sodium chloroacetate, $NaIO_4$ followed by Protein A, divinylsulfone followed by Protein A, allyl glycidyl ether followed firstly by a halohydrin-forming reagent (e.g. N-bromosuccinamide) and subsequently by Protein A, or allyl glycidyl ether followed firstly by an epoxide-forming reagent and subsequently by Protein A.

Alternatively, the functionalised chromatography medium is a functionalised cellulose chromatography medium and the substrate is formed of one or more cellulose acetate nanofibres, the step of grafting comprises both the conversion of cellulose acetate to cellulose and the grafting of one or more neutral polymer chains onto the resultant cellulose substrate via glycidol polymerisation, and the grafted product is contacted with a reagent chosen from glycidyltrimethylammonium chloride (GMAC), 1,4-butanesulfone, sodium chloroacetate, $NaIO_4$ followed by Protein A, divinylsulfone followed by Protein A, allyl glycidyl ether followed firstly by a halohydrin-forming reagent (e.g. N-bromosuccinamide) and subsequently by Protein A, or allyl glycidyl ether followed firstly by an epoxide-forming reagent and subsequently by Protein A.

In a preferred embodiment, the present invention provides a process for preparing a functionalised cellulose chromatography medium, which process comprises (i) providing a substrate formed of one or more cellulose acetate nanofibres, treating the cellulose acetate to convert it to cellulose, (ii) grafting one or more neutral polymer chains from the resultant cellulose substrate, as defined herein, and (iii) contacting the grafted product with a reagent, as defined herein, which functionalises the product of step (ii) as a chromatography medium, as defined herein, wherein the grafting step (ii) comprises reacting a plurality of compounds of formula

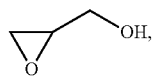

and/or its enantiomers, with one or more functional groups present on the nanofibre substrate.

Typically in this preferred embodiment step (i) comprises providing a substrate formed of one or more non-woven sheets, each comprising one or more cellulose acetate nanofibres.

Preferably in this preferred embodiment step (i) comprises providing two or more non-woven sheets stacked one on top of the other, each said sheet comprising one or more cellulose acetate nanofibres, and simultaneously heating and pressing the stack of sheets to fuse points of contact between the nanofibres of adjacent sheets.

In an alternative preferred embodiment, the present invention provides a process for preparing a functionalised cellulose chromatography medium, which process comprises (i) providing a substrate formed of one or more cellulose acetate nanofibres, (ii) subjecting the substrate to conditions under which both the cellulose acetate is converted to cellulose and, subsequently, one or more neutral polymer chains are grafted onto the resultant cellulose substrate, and (iii) contacting the grafted product with a reagent, as defined herein, which functionalises the product of step (ii) as a chromatography medium, as defined herein, wherein the grafting step (ii) comprises reacting a plurality of compounds of formula

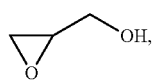

and/or its enantiomers, with one or more functional groups present on the nanofibre substrate.

Typically in this alternative preferred embodiment step (i) comprises providing a substrate formed of one or more non-woven sheets, each comprising one or more cellulose acetate nanofibres.

Preferably in this alternative preferred embodiment step (i) comprises providing two or more non-woven sheets stacked one on top of the other, each said sheet comprising one or more cellulose acetate nanofibres, and simultaneously heating and pressing the stack of sheets to fuse points of contact between the nanofibres of adjacent sheets.

In a more preferred embodiment, the present invention provides a process for preparing a functionalised cellulose chromatography medium, which process comprises (i) providing a substrate formed of one or more cellulose acetate nanofibres, treating the cellulose acetate to convert it to cellulose, (ii) grafting one or more polymer chains from the resultant cellulose substrate by reacting a plurality of compounds of formula

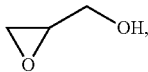

and/or its enantiomers, with one or more hydroxyl groups present on the substrate, and (iii) contacting the grafted product with a reagent, as defined herein, which functionalises the product of step (ii) as a chromatography medium.

Typically in this more preferred embodiment step (i) comprises providing a substrate formed of one or more non-woven sheets, each comprising one or more cellulose acetate nanofibres.

Preferably in this more preferred embodiment step (i) comprises providing two or more non-woven sheets stacked one on top of the other, each said sheet comprising one or more cellulose acetate nanofibres, and simultaneously heating and pressing the stack of sheets to fuse points of contact between the nanofibres of adjacent sheets.

In an alternative more preferred embodiment, the present invention provides a process for preparing a functionalised cellulose chromatography medium, which process comprises (i) providing a substrate formed of one or more cellulose acetate nanofibres, (ii) subjecting the substrate to aqueous alkaline conditions under which both the cellulose acetate is converted to cellulose and, subsequently, one or more neutral polymer chains are grafted onto the resultant cellulose substrate by reaction of a plurality of compounds of formula

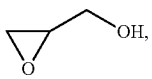

and/or its enantiomers, with one or more hydroxyl groups present on the substrate, and (iii) contacting the grafted product with a reagent, as defined herein, which functionalises the product of step (ii) as a chromatography medium.

Typically in this alternative more preferred embodiment step (i) comprises providing a substrate formed of one or more non-woven sheets, each comprising one or more cellulose acetate nanofibres.

Preferably in this alternative more preferred embodiment step (i) comprises providing two or more non-woven sheets stacked one on top of the other, each said sheet comprising one or more cellulose acetate nanofibres, and simultaneously heating and pressing the stack of sheets to fuse points of contact between the nanofibres of adjacent sheets.

In an even more preferable embodiment, the present invention provides a process for preparing a functionalised cellulose chromatography medium, which process comprises (i) providing a substrate formed of one or more cellulose acetate nanofibres, treating the cellulose acetate to convert it to cellulose, (ii) grafting one or more polymer chains from the resultant cellulose substrate by reacting a plurality of compounds of formula

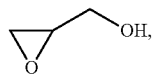

and/or its enantiomers, with one or more hydroxyl groups present on the substrate, and (iii) contacting the grafted product with a reagent which functionalises the product of step (ii) as a chromatography medium suitable for use in an ion exchange or affinity chromatography method.

Typically in this even more preferred embodiment step (i) comprises providing a substrate formed of one or more non-woven sheets, each comprising one or more cellulose acetate nanofibres.

Preferably in this even more preferred embodiment step (i) comprises providing two or more non-woven sheets stacked one on top of the other, each said sheet comprising one or more cellulose acetate nanofibres, and simultaneously heating and pressing the stack of sheets to fuse points of contact between the nanofibres of adjacent sheets.

In an alternative even more preferred embodiment, the present invention provides a process for preparing a functionalised cellulose chromatography medium, which process comprises (i) providing a substrate formed of one or more cellulose acetate nanofibres, (ii) subjecting the substrate to aqueous alkaline conditions under which both the cellulose acetate is converted to cellulose and, subsequently, one or more neutral polymer chains are grafted onto the resultant cellulose substrate by reaction of a plurality of compounds of formula

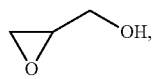

and/or its enantiomers, with one or more hydroxyl groups present on the substrate, and (iii) contacting the grafted product with a reagent which functionalises the product of step (ii) as a chromatography medium suitable for use in an ion exchange or affinity chromatography method.

Typically in this alternative even more preferred embodiment step (i) comprises providing a substrate formed of one or more non-woven sheets, each comprising one or more cellulose acetate nanofibres.

Preferably in this alternative even more preferred embodiment step (i) comprises providing two or more non-woven sheets stacked one on top of the other, each said sheet comprising one or more cellulose acetate nanofibres, and simultaneously heating and pressing the stack of sheets to fuse points of contact between the nanofibres of adjacent sheets.

In a yet more preferred embodiment, the present invention provides a process for preparing a functionalised cellulose chromatography medium, which process comprises (i) providing a substrate formed of one or more cellulose acetate nanofibres, treating the cellulose acetate to convert it to cellulose, (ii) grafting one or more polymer chains from the resultant cellulose substrate by reacting a plurality of compounds of formula

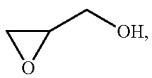

and its enantiomers, with one or more hydroxyl groups present on the substrate, and (iii) contacting the grafted product with a reagent which functionalises the product of step (ii) as a chromatography medium suitable for use in an ion exchange or affinity chromatography method, which reagent is glycidyltrimethylammonium chloride (GMAC), 1,4-butanesulfone, sodium chloroacetate, $NaIO_4$ followed by Protein A, divinylsulfone followed by Protein A, allyl glycidyl ether followed firstly by a halohydrin-forming reagent (e.g. N-bromosuccinamide) and subsequently by Protein A, or allyl glycidyl ether followed firstly by an epoxide-forming reagent and subsequently by Protein A.

Typically in this yet more preferred embodiment step (i) comprises providing a substrate formed of one or more non-woven sheets, each comprising one or more cellulose acetate nanofibres.

Preferably in this yet more preferred embodiment step (i) comprises providing two or more non-woven sheets stacked one on top of the other, each said sheet comprising one or more cellulose acetate nanofibres, and simultaneously heating and pressing the stack of sheets to fuse points of contact between the nanofibres of adjacent sheets.

In an alternative yet more preferred embodiment, the present invention provides a process for preparing a functionalised cellulose chromatography medium, which process comprises (i) providing a substrate formed of one or more cellulose acetate nanofibres, (ii) subjecting the substrate to aqueous alkaline conditions under which both the cellulose acetate is converted to cellulose and, subsequently, one or more neutral polymer chains are grafted onto the resultant cellulose substrate by reaction of a plurality of compounds of formula

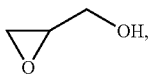

and/or its enantiomers, with one or more hydroxyl groups present on the substrate, and (iii) contacting the grafted product with a reagent which functionalises the product of step (ii) as a chromatography medium suitable for use in an ion exchange or affinity chromatography method, which reagent is glycidyltrimethylammonium chloride (GMAC), 1,4-butanesulfone, sodium chloroacetate, $NaIO_4$ followed by Protein A, divinylsulfone followed by Protein A, allyl glycidyl ether followed firstly by a halohydrin-forming reagent (e.g. N-bromosuccinamide) and subsequently by Protein A, or allyl glycidyl ether followed firstly by an epoxide-forming reagent and subsequently by Protein A.

Typically in this alternative yet more preferred embodiment step (i) comprises providing a substrate formed of one or more non-woven sheets, each comprising one or more cellulose acetate nanofibres.

Preferably in this alternative yet more preferred embodiment step (i) comprises providing two or more non-woven sheets stacked one on top of the other, each said sheet comprising one or more cellulose acetate nanofibres, and simultaneously heating and pressing the stack of sheets to fuse points of contact between the nanofibres of adjacent sheets.

In a further even more preferred embodiment, the present invention provides a process for preparing a functionalised cellulose chromatography medium, which process comprises (i) providing a substrate formed of one or more cellulose acetate nanofibres, treating the cellulose acetate to convert it to cellulose, (ii) grafting one or more polymer chains from the resultant cellulose substrate by reacting a plurality of compounds of formula

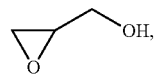

and its enantiomers, with one or more hydroxyl groups present on the substrate, and (iii) contacting the grafted product with a reagent which functionalises the product of step (ii) as a chromatography medium suitable for use in an ion exchange or affinity chromatography method, which reagent is divinylsulfone followed by Protein A, allyl glycidyl ether followed firstly by a halohydrin-forming reagent (e.g. N-bromosuccinamide) and subsequently by Protein A, or allyl glycidyl ether followed firstly by an epoxide-forming reagent and subsequently by Protein A.

Typically in this further even more preferred embodiment step (i) comprises providing a substrate formed of one or more non-woven sheets, each comprising one or more cellulose acetate nanofibres.

Preferably in this further even more preferred embodiment step (i) comprises providing two or more non-woven sheets stacked one on top of the other, each said sheet comprising one or more cellulose acetate nanofibres, and simultaneously heating and pressing the stack of sheets to fuse points of contact between the nanofibres of adjacent sheets.

In an alternative further even more preferred embodiment, the present invention provides a process for preparing a functionalised cellulose chromatography medium, which process comprises (i) providing a substrate formed of one or more cellulose acetate nanofibres, (ii) subjecting the substrate to aqueous alkaline conditions under which both the cellulose acetate is converted to cellulose and, subsequently, one or more neutral polymer chains are grafted onto the resultant cellulose substrate by reaction of a plurality of compounds of formula

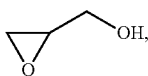

and/or its enantiomers, with one or more hydroxyl groups present on the substrate, and (iii) contacting the grafted product with a reagent which functionalises the product of step (ii) as a chromatography medium suitable for use in an ion exchange or affinity chromatography method, which reagent is divinylsulfone followed by Protein A, allyl glycidyl ether followed firstly by a halohydrin-forming reagent (e.g. N-bromosuccinamide) and subsequently by Protein A, or allyl glycidyl ether followed firstly by an epoxide-forming reagent and subsequently by Protein A.

Typically in this alternative further even more preferred embodiment step (i) comprises providing a substrate formed of one or more non-woven sheets, each comprising one or more cellulose acetate nanofibres.

Preferably in this alternative further even more preferred embodiment step (i) comprises providing two or more non-woven sheets stacked one on top of the other, each said sheet comprising one or more cellulose acetate nanofibres, and simultaneously heating and pressing the stack of sheets to fuse points of contact between the nanofibres of adjacent sheets.

Chromatography Cartridge of the Invention

The present invention also provides a chromatography cartridge. The chromatography cartridge of the present invention comprises one or more functionalised chromatography media of the present invention. Alternatively, the chromatography cartridge of the present invention is obtainable by carrying out the process of the present invention and incorporating the thus-obtained product into a cartridge.

Also provided is a process for preparing a chromatography cartridge which comprises carrying out the process of the present invention and incorporating the thus-obtained product into a cartridge.

The chromatography cartridge is typically suitable for use in chromatography, preferably a chromatography method as defined herein.

A chromatography cartridge of the present invention typically comprises one or more functionalised chromatography media of the present invention within a holder, for example a holder as defined above. The holder is typically cylindrical.

Typically, the chromatography cartridge comprises one or more functionalised chromatography media of the present invention stacked inside a cylindrical holder.

Typically, the chromatography cartridge comprises two or more functionalised chromatography media of the present invention. Typically, the chromatography cartridge comprises up to twenty functionalised chromatography media of the present invention.

Typically, the chromatography cartridge also comprises one or more frits within the typically cylindrical holder. Frits are well known to the person skilled in the art and refer to rigid porous structures, typically rigid metal, polymeric or ceramic, preferably rigid metal or ceramic, porous structures. Frits are typically included in a chromatography cartridge to improve flow distribution through the cartridge and/or to support the one or more functionalised chromatography media of the present invention. Pores in typical frits have diameters from 1 to 1000 µm, preferably from 5 to 500 µm, more preferably from 10 to 150 µm. Other suitable frit pore diameters include from 1 to 20 µm, preferably from 5 to 10 µm, more preferably from 3 to 7 µm.

Typically, the cartridge comprises two or more functionalised chromatography media of the present invention and one or more frits, the frits being located between functionalised chromatography media.

In some embodiments, the cartridge does not comprise frits.

The cartridge may comprise alternative spacer materials instead of or in addition to frits. Typical alternative spacer materials include non-woven and woven materials.

Non-woven polymer materials are known to the person of skill in the art. Such non-woven materials are porous, i.e. allow the passage of liquid, typically without significant pressure drop. Typically, the non-woven polymer material is polypropylene. Typically, the non-woven material has an area density of 45-150 gsm.

In some embodiments, the cartridge comprises two or more functionalised chromatography media of the present invention and one or more non-woven polymer material layers as defined above, the one or more non-woven polymer material layers being located between functionalised chromatography media.

Woven materials are known to the person of skill in the art. Such woven materials are porous, i.e. allow the passage of liquid, typically without significant pressure drop. Typically, the woven material is a woven polymer material, preferably woven polypropylene. Typically, the woven material has a thickness less than 1 mm.

Typically, the chromatography cartridge also comprises one or more inlet fluid distribution means and/or outlet fluid collection means. Such means are well known to the person skilled in the art.

Chromatography Method of the Invention

The present invention also provides use of a functionalised chromatography medium of the invention or a chromatography cartridge of the invention in chromatography, particularly in a chromatography method as defined herein.

The present invention also provides a process for isolating one or more biological molecules from a mobile phase, which process comprises contacting one or more biological molecules in a mobile phase with a functionalised chromatography medium of the invention or a chromatography cartridge of the invention. The chromatography medium or chromatography cartridge binds preferentially to the one or more biological molecules in the mobile phase, typically in preference to other components (for instance other biological molecules) also present in the mobile phase. This can be carried out in accordance with conventional methods known for the bind phase of such chromatographic methods.

Thus, typically, this chromatographic process is an ion (anion or cation) exchange, affinity capture, hydrophobic interaction or mixed mode chromatography process.

Preferably, the chromatographic process is an anion exchange chromatography process and the chromatography medium is functionalised with DEAE or Q; the chromatographic process is a cation exchange chromatography process and the chromatography medium is functionalised with SP or CM; the chromatographic process is an affinity capture chromatography process and the chromatography medium is functionalised with Protein A; or the chromatographic process is a hydrophobic interaction chromatography process and the chromatography medium is functionalised with phenyl groups.

Thus, the present invention provides a chromatography process which comprises the above step. Typically, the chromatography process is carried out in accordance with a chromatography method as defined above.

One of the advantageous findings of the present invention is that a functionalised chromatography material produced by the process of the invention has a high binding capacity and can be operated at high flowrates. Thus, typically in the chromatography process of the present invention, the one or more biological molecules in a mobile phase is contacted with the functionalised chromatography medium for a period of time of one minute or less, preferably 50 seconds or less, more preferably 40 seconds or less, yet more preferably 30 seconds or less, still more preferably 20 seconds or less, or even 15 seconds or less, 12 seconds or less, 10 seconds or less, 8 seconds or less, 6 seconds or less, 4 seconds or less, 2 seconds or less, 1.5 seconds or less, or even 1 second or less.

The chromatography process typically comprises a further step of recovering the one or more biological molecules from the functionalised chromatography medium or chromatography cartridge. This step can typically be effected by contacting the functionalised chromatography medium or chromatography cartridge to which is adsorbed the one or more biological molecules with an elution buffer. This can be carried out in accordance with conventional methods known for the elute phase of such chromatographic methods. Thus, the process is typically a bind-elute chromatographic method.

Between the bind and elute steps, the process may further comprise a step of washing the functionalised chromatography medium or chromatography cartridge of the invention to which is adsorbed the one or more biological molecules. This washing step is carried out to remove any components which are not bound to the functionalised chromatography medium or chromatography cartridge. This can be carried out in accordance with conventional methods known for the washing phase of such chromatographic methods.

After the elute step, the process may further comprise a step of regenerating the functionalised chromatography medium or chromatography cartridge of the invention. Typically this is effected by contacting the functionalised chromatography medium or chromatography cartridge from which the one or more biological molecules have been eluted with a buffer. This can be carried out in accordance with conventional methods known for the regeneration phase of such chromatographic methods.

Typically, the one or more biological molecules are chosen from cells, proteins, polypeptides, antibodies, amino acids, viruses and nucleic acids, including, for example, recombinant proteins, monoclonal antibodies, viral vaccines, viral vectors, RNA, exosomes, cells and plasmid DNA.

The monoclonal antibody may be a multispecific antibody (e.g. a bispecific antibody) or a domain-deleted antibody. Preferably the monoclonal antibody is a humanized antibody or a human antibody. Antigen-binding fragments of monoclonal antibodies may be used. Examples of antibody fragments include Fab, Fab', F(ab')$_2$ and Fv fragments, diabodies and single chain antibodies.

Typically, the one or more biological molecules are one or more monoclonal antibodies, or proteins engineered to exhibit a site with an affinity for Protein A binding, and the functionalised chromatography medium optionally contained in a cartridge carries at least one Protein A ligand group.

Typically, the chromatographic process employs a simulated or actual moving bed system. Thus typically, the process comprises introducing the one or more biological molecules in a mobile phase into one or more simulated or actual moving bed chromatography apparatuses having a plurality of linked chromatography columns, which chromatography columns contain as adsorbent the functionalised chromatography medium of the present invention.

Any known simulated or actual moving bed apparatus may be used to carry out the chromatographic process, provided that it comprises, as adsorbent, the functionalised chromatography medium of the present invention.

Simulated and actual moving bed chromatography are known techniques, familiar to those of skill in the art. The principle of operation involves countercurrent movement of a liquid eluent phase and a solid adsorbent phase. This operation allows minimal usage of solvent making the process economically viable. Such separation technology has found applications in diverse areas including purification of biological molecules using membrane adsorbents.

A simulated moving bed system consists of a number of individual columns containing adsorbent which are connected together in series. Eluent is passed through the columns in a first direction. The injection points of the feedstock and the eluent, and the separated component collection points in the system are periodically shifted by means of a series of valves. The overall effect is to simulate the operation of a single column containing a moving bed of the solid adsorbent. Thus, a simulated moving bed system consists of columns which, as in a conventional stationary bed system, contain stationary beds of solid adsorbent through which eluent is passed, but in a simulated moving bed system the operation is such as to simulate a continuous countercurrent moving bed.

An actual moving bed system is similar in operation to a simulated moving bed system. However, rather than shifting the injection points of the feed mixture and the eluent, and the separated component collection points by means of a system of valves, instead a series of adsorption units (i.e. columns) are physically moved relative to the feed and drawoff points. Again, operation is such as to simulate a continuous countercurrent moving bed.

The materials of the present invention are also suitable for use in methods of immobilised enzyme biocatalysis, metal scavenging, and water treatment. Thus, the present invention provides a method of enzyme biocatalysis, which involves a functionalised chromatographic material of the present invention. The present invention also provides a method of metal scavenging, which involves a functionalised chromatographic material of the present invention. The present invention also provides a method of water treatment, which involves a functionalised chromatographic material of the present invention. It will be appreciated that certain minor modifications may be required to the processes and products of the invention to render the products suitable for use in these methods.

EXAMPLES

The following Examples illustrate the invention.
Materials and Equipment
Unless otherwise noted all chemicals were obtained from, or are available from, companies such as Fisher Scientific, Sigma-Aldrich, FluoroChem, Repligen, and VWR.
Washing Protocols
Washing Protocol A
The reaction media was replaced with an equal volume de-ionised water and circulated for 1 hour. The rinsing procedure was repeated once more. Finally, the materials were treated with an equal volume of aqueous ethanol (2:1—H$_2$O:EtOH) before being removed from the reaction vessel.

Washing Protocol B

The reaction media was replaced with an equal volume of de-ionised water and circulated for 1 hour. After this time, the washing media was replaced with 0.01M HCl which was circulated for 1 hour whereupon it was replaced with 0.001M HCl and circulated for 1 hour. Finally, the media was replaced with 2:1 mixture of H$_2$O:EtOH which was circulated for 1 hour. The derivatised nanofibres were then removed from the reaction vessel.

Washing Protocol C

The reaction media was replaced with an equal volume of 1:1 mixture of warm (60° C.) de-ionised water:acetone which was circulated for 30 mins. The washing procedure was repeated twice more. Finally, the media was replaced with 2:1 mixture of H$_2$O:EtOH which was circulated for 1 hour. The derivatised nanofibres were then removed from the reaction vessel.

Washing Protocol D

2 Ltrs of ultrapure water was pumped through the nanofibre material.

Washing Protocol E

The reaction media was replaced with an equal volume of 1:1-de-ionised water:EtOH and circulated for 1 hour. The washing procedure was repeated twice more. Finally, the media was replaced with 2:1 mixture of H$_2$O:EtOH which was circulated for 1 hour. The derivatised nanofibres were then removed from the reaction vessel. Finally, the media was replaced with 2:1 mixture of H$_2$O:EtOH which was circulated for 1 hour. The derivatised nanofibres were then removed from the reaction vessel.

Washing Protocol F

The reaction media was replaced with ultapure de-ionised water. The nanofibre materials were gently stirred in the clean water for 30 mins. After this time, the washing media was replaced and the wash cycle repeated.

Washing Protocol G

The reaction media was poured out and the beaker was replenished with water until the pH of the effluent was neutral or slightly acidic.

Washing Protocol H (for Halohydrin Nanofibers)

The reaction media was replaced with an equal volume of 1:1 mixture of de-ionised water:acetone which was circulated for 1 hour. After this time the wash solution was refreshed and the fibres washed for a further 1 hour while stirring vigorously. This process was repeated a further 3 times before the final wash of de-ionised water for a further 1 hour. The derivatised halohydrin nanofibers were then removed from the reaction vessel and were ready for use in the next step.

I Preparation of Materials

Preparative Example 1

A solution of cellulose acetate, with a relative molecular mass of 29,000 g/mol, was dissolved in common solvents prior to electrospinning to produce fibres with diameters ranging between 300-600 nm. Optimised conditions for nanofibre production can be found in, for example, O. Hardick, et al, J. Mater. Sci. 46 (2011) 3890, the entirety of which is incorporated herein by reference. Sheets of approximately 20 g/m$^2$ material were layered and subjected to a combined heating and pressure treatment.

Example 1—Glycidol/Trimethylammonium Chloride Functionalization

Nanofibre materials were derivatised according the scheme outlined below:

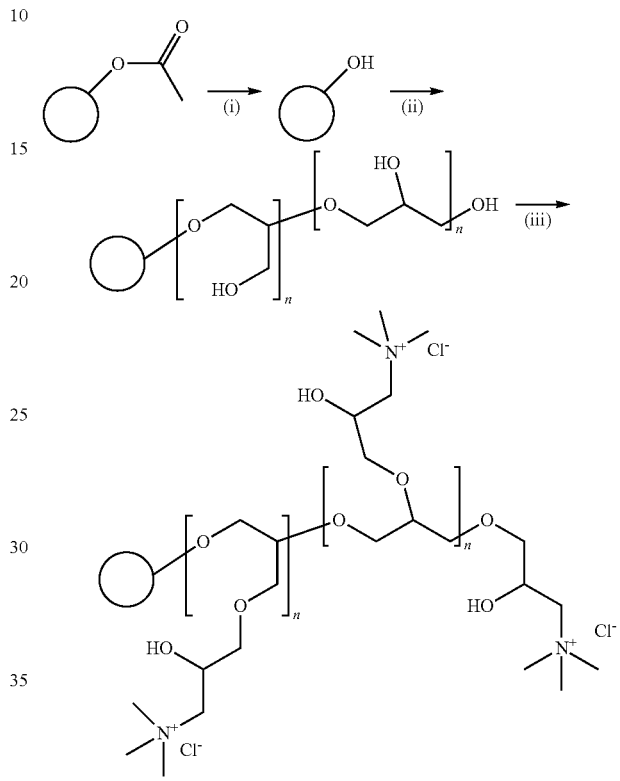

Step (i): Saponification of Cellulose Acetate (CA) to Regenerated Cellulose (RC)

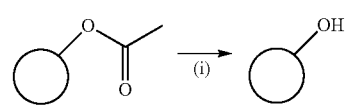

Cellulose acetate sheets (44*32 mm*150 mm) obtained in accordance with the method of Preparative Example 1 were placed into a large beaker containing 5 L of a 0.075M sodium hydroxide solution in 2:1-water:ethanol. The reaction mixture was stirred at room temperature for 48 hours. The materials were then washed according to washing protocol A.

Step (ii): Glycidol Polymerisation

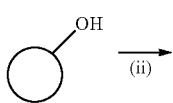

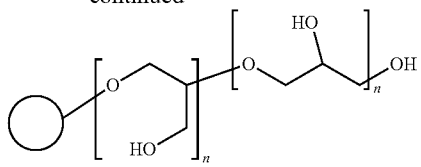

Materials from (i) were suspended in 1 L of 0.5M NaOH. The reaction media was circulated for 15 minutes prior to the careful addition of varying amounts of Glycidol (15 mL, 30 mL, 60 mL, 120 mL, 180 mL) in a single portion. The reaction media was circulated at room temperature for 16 hours and the material was subsequently washed according to washing protocol B.

Step (iii): Glycidyltrimethylammonium Chloride Derivatisation

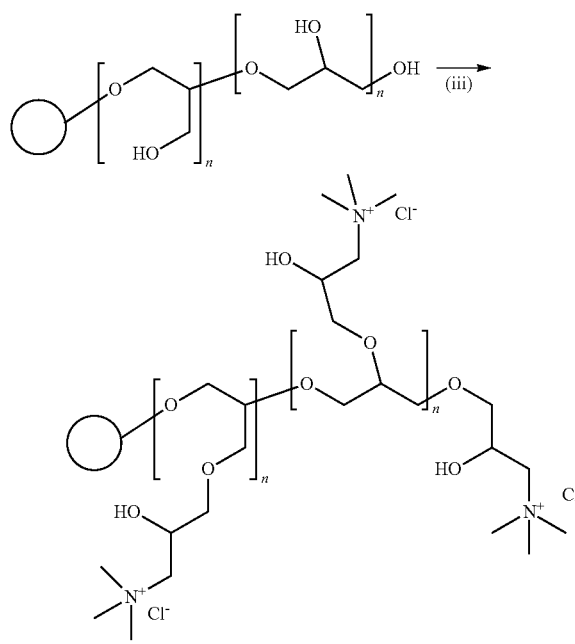

Materials obtained in step (ii) were typically suspended in 1 Ltr 0.5M NaOH. The reaction media was circulated for 15 minutes prior to the addition of glycidyltrimethylammonium chloride (25 mL, 50 mL, 100 mL and 200 mL) in a single portion. The reaction media was circulated for a further 16 hours at room temperature. The materials were then washed according to washing protocol C.

The trimethylammonium chloride content was determined by the following method. 50 mg of material was washed with 100 mL 0.1M HCl solution on a Buchner filter funnel and then with a further 100 mL 0.01M HCl solution. The material was then placed in a drying oven at 75° C. and dried to constant mass before being torn into small pieces and then placed in a 50 mL centrifuge tube. A small magnetic stir bar and 15 mL deionised water were then added along with approximately 1 mL (added via a teat pipette) potassium chromate solution which caused the mixture to become yellow in colour. The mixture was stirred vigorously for 20 minutes before being titrated with 0.1M silver nitrate. The endpoint of the titration is identified by a change in colour from clear yellow to misty brown.

The trimethylammonium chloride content (μmol/g) was calculated as the number of micromoles of silver nitrate added to reach end point/number of grams of nanofibre material used in the titration.

Example 2—Glycidol/S Functionalization

Nanofibre materials were derivatised according to the scheme outlined below:

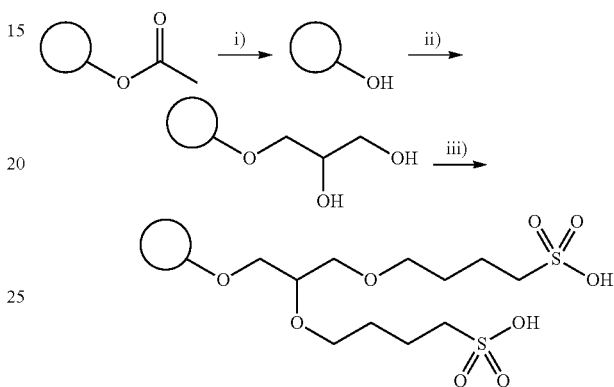

Step (i): Saponification of Cellulose Acetate (CA) to Regenerated Cellulose (RC)

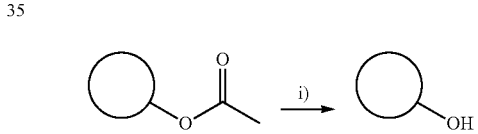

Cellulose acetate sheets (44*32 mm*150 mm) obtained in accordance with the method of Preparative Example 1 were suspended in 5 L of a 0.075M sodium hydroxide solution in 2:1-water:ethanol. The reaction mixture was circulated at room temperature for 48 hours. The materials were then washed according to washing protocol A.

Step (ii): Glycidol Derivatisation

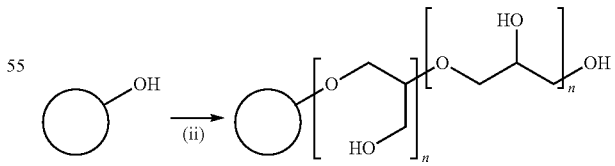

Materials from (i) were suspended in 1 L of 0.5M NaOH. The reaction media was circulated for 15 minutes prior to the careful addition of varying amounts of glycidol (15 mL, 30 mL, 120 mL, 180 mL) in a single portion. The reaction media was circulated at room temperature for 16 hours and the material was subsequently washed according to washing protocol B.

Step (iii): 1,4-Butanesulfone Derivatisation

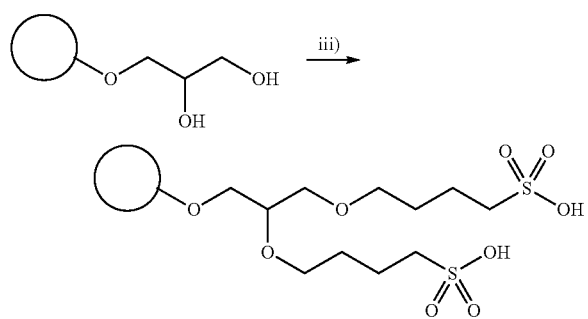

Reaction media consisting of 150 ml 1M NaOH (aq.) was heated up to 53° C. In this was suspended glycidol functionalised material obtained in step (ii), along with 1,4-butanesulfone (6 ml, 53° C., 58.6 mmol). The reaction media was stirred at 60° C. for 15 min, 30 min, and 60 min. The materials were then washed according to washing protocol B.

The sulfonic acid (S) content of the material (μmol/g) was calculated via titration. Dried material from (iii) was washed with 0.1M HCL and 0.01M HCl. The material is then oven dried and weighed. After washing the molarity of the material is determined from the amount of NaOH added to reach pH7.

Example 3—Glycidol/Carboxymethyl (CM) Functionalisation

Nanofibre materials were derivatised according the scheme outlined below:

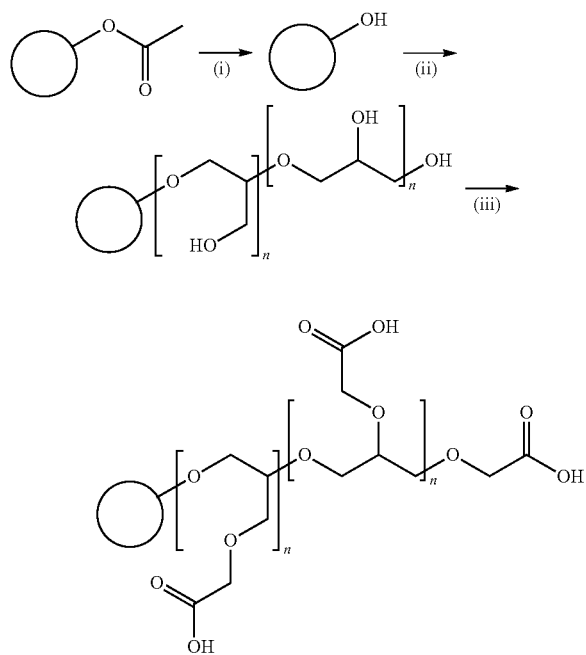

Step (i): Saponification of Cellulose Acetate (CA) to Regenerated Cellulose (RC)

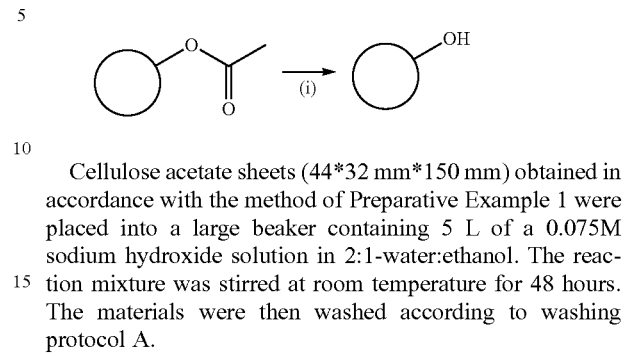

Cellulose acetate sheets (44*32 mm*150 mm) obtained in accordance with the method of Preparative Example 1 were placed into a large beaker containing 5 L of a 0.075M sodium hydroxide solution in 2:1-water:ethanol. The reaction mixture was stirred at room temperature for 48 hours. The materials were then washed according to washing protocol A.

Step (ii): Glycidol Polymerisation

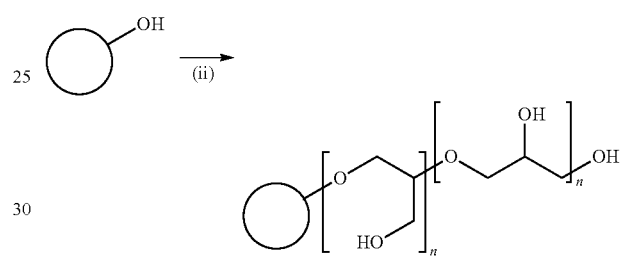

Materials from (i) were suspended in 1 L of 0.5M NaOH. The reaction media was circulated for 15 minutes prior to the careful addition of varying amounts of Glycidol (15 mL, 30 mL, 60 mL, 120 mL, 180 mL) in a single portion. The reaction media was circulated at room temperature for 16 hours and the material was subsequently washed according to washing protocol B.

Step (iii): Carboxymethyl (CM) Derivatisation

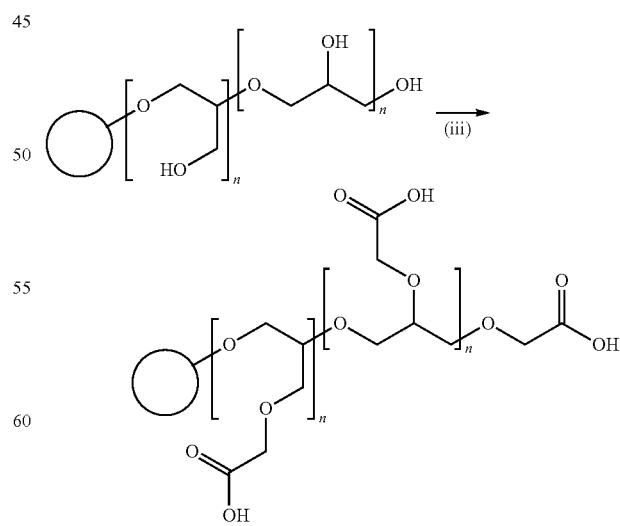

Materials from (ii) were suspended in water (66 mL) at 62° C. A solution of sodium chloroacetate (12.8 g) in water (27.5 mL) was freshly prepared. A solution of KOH (6.2 g) in water (27.5 mL) was also freshly prepared. Both solutions were added to the reaction at a rate of 13.75 mL/hour while keeping the temperature at 62° C. The reaction was stirred vigorously at 62° C. for 4 h in total. After 4 h at 62° C., the reaction media was removed and the nanofibre materials were washed under a continuous flow of water until the pH of the effluent was neutral. The beaker was then stirred in 0.01M hydrochloric acid aqueous solution until a steady pH of 2-3 was reached.

Reference Example 1—ATRP Functionalization to Provide Dimethylamino-Derivatised Nanofibre Materials Nanofibre materials were derivatised according the scheme outlined below:

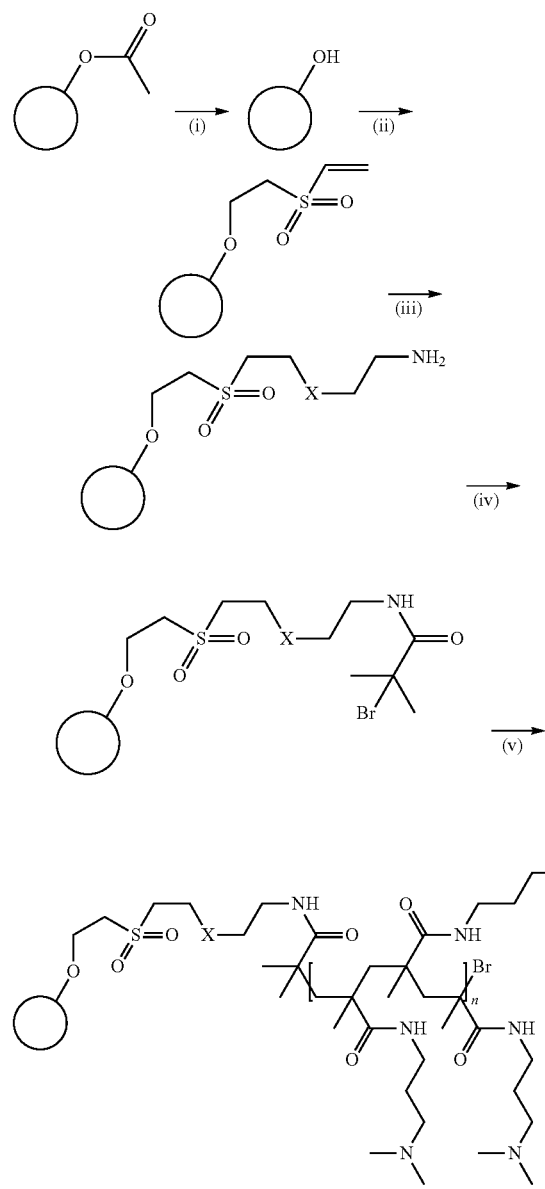

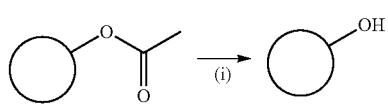

X = S or N

Step (i): Saponification of Cellulose Acetate (CA) to Regenerated Cellulose (RC)

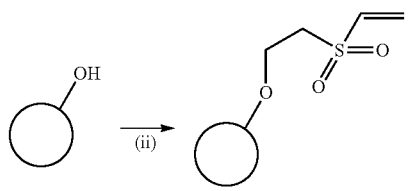

Cellulose acetate sheets (44*32 mm*150 mm) obtained in accordance with the method of Preparative Example 1 were placed into a large beaker containing 5 L of a 0.075M sodium hydroxide solution in 2:1-water:ethanol. The reaction mixture was stirred at room temperature for 48 hours. The materials were then washed according to washing protocol A.

Step (ii): Divinylsulfone Derivatisation

Material obtained in step (i) was suspended in a solution of $K_2CO_3$ (24.4 g, 176.54 mmol $K_2CO_3$ in 275 mL $H_2O$) and acetonitrile (75 mL). The mixture was stirred for 15 minutes prior to the dropwise addition of divinylsulfone (50 mL, 498.1 mmol) over 2.5 hours. Upon complete addition of the divinylsulfone, the reaction was stirred for a further 1.5 hours. After this time, the nanofibre material was washed according to washing protocol C.

Step (iii)

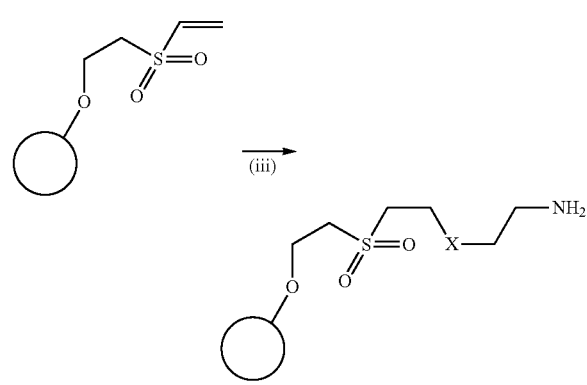

Material obtained in step (ii) was suspended in 375 mL $H_2O$ that contained either ethylenediamine (125 mL, 1870 mmol) or 2-mercaptoethylamine hydrochloride (37.5 g, 167 mmol). The mixture was stirred overnight at room temperature. After this time, the derivatised nanofibre material was washed according to washing protocol A.

Step (iv): α-Bromoisobutyryl Bromide Derivatisation

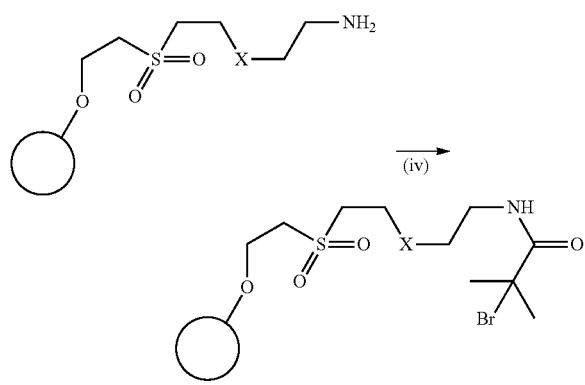

Dry material obtained in step (iii) was placed in a centrifuge tube and 2 mL acetonitrile and 0.4 mL (3.24 mmol) α-bromoisobutyryl bromide were added. The tubes were gently agitated on an orbital shaker for 5 minutes at room temperature, whereupon triethylamine was added dropwise (0.4 ml, 2.86 mmol). The reaction mixture was agitated for 1 hour. After this time, the derivatised nanofibre materials were washed according to washing protocol A.

Step (v): ATRP

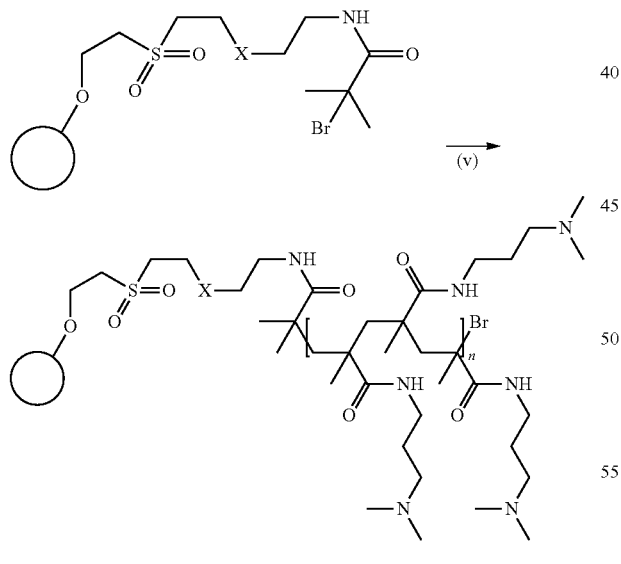

Typically, derivatised nanofibre material obtained in step (iv) was placed in a reaction vessel to which was added 2.5 mL saturated ascorbic acid, 0.33 ml catalyst solution A and N-[3-(dimethylamino)propyl]methacrylamide (1.66 mL, 9.2 mmol). The reaction mixture was gently agitated on an orbital shaker at room temperature for 4 hrs. After this time, the derivatised nanofibre materials were washed according to washing protocol A.

Catalyst Solution A $CuBr_2$ (0.3 g, 1.343 mmol) dissolved in 10 ml $H_2O$ and 0.45 mL (1.650 mmol) 1,1,4,7,10,10-hexamethyltriethylenetetramine.

Example 4—Glycidol Grafted, Aldehyde Functionalised, Protein A Coupled Material

Nanofibre materials were derivatised according the scheme outlined below:

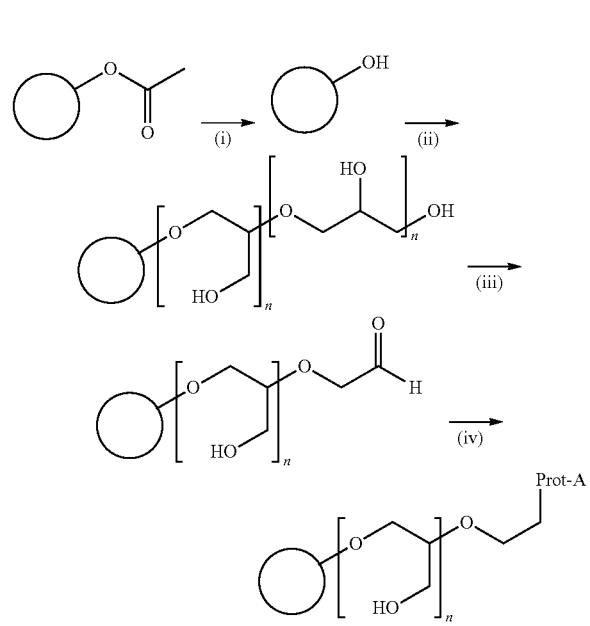

Step (i): Saponification of Cellulose Acetate (CA) to Regenerated Cellulose (RC)

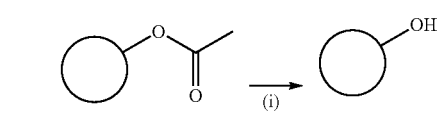

Cellulose acetate sheets (44*32 mm*150 mm) obtained in accordance with the method of Preparative Example 1 were placed into a large beaker containing 5 L of a 0.075M sodium hydroxide solution in 2:1-water:ethanol. The reaction mixture was stirred at room temperature for 48 hours. The materials were then washed according to washing protocol A.

Step (ii): Glycidol Polymerisation

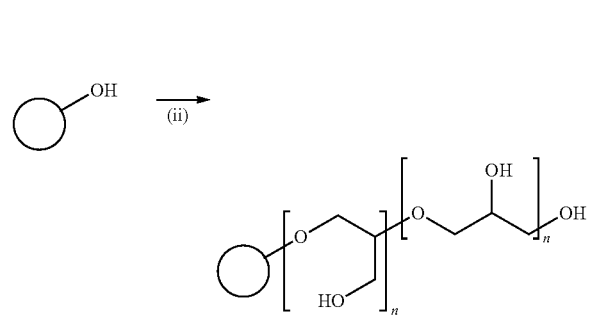

Materials from (i) were suspended in 1 L of 0.5M NaOH. The reaction media was circulated for 15 minutes prior to the careful addition of 180 mL glycidol in a single portion. The reaction media was circulated at room temperature for 16 hours and the material was subsequently washed according to washing protocol B.

Step (iii): Oxidation to Aldehyde

Material from (ii) was suspended in 17.5 L 0.05M NaOAc buffer modified to pH5.5. The reaction media was circulated for 30 mins prior to the addition of NaIO$_4$ (200 g, 0.94 moles, dissolved in 2 L of reaction media). The reaction media was circulated for a further 30 mins. The materials were then washed according to washing protocol C to provide aldehyde functionalised materials.

Step (iv): Protein A Coupling

Materials from step (iii) were added to a 6 well plate. To each well was added 2 mL of a protein-A solution (rSPA, 50 mg/ml Protein A in deionised water). The plate gently agitated on an orbital shaker for 1 hr. After this time, the supernatant liquid was removed and replaced with reducing buffer solution A (2.5 ml per well, prepared as 0.0762 g of NaCNBH$_3$ added to 10 mL carbonate buffer, which is prepared as 0.0603 g Na$_2$CO$_3$ (0.569 mmol) and 0.337 g NaHCO$_3$ (4.012 mmol) added to 100 mL de-ionised water) and agitated for a further 15 minutes. After this time the protein-A coupled materials were washed according to protocol D.

Example 5—Glycidol Grafted, DVS Functionalised, Protein A Coupled Material

Nanofibre materials were derivatised according the scheme outlined below:

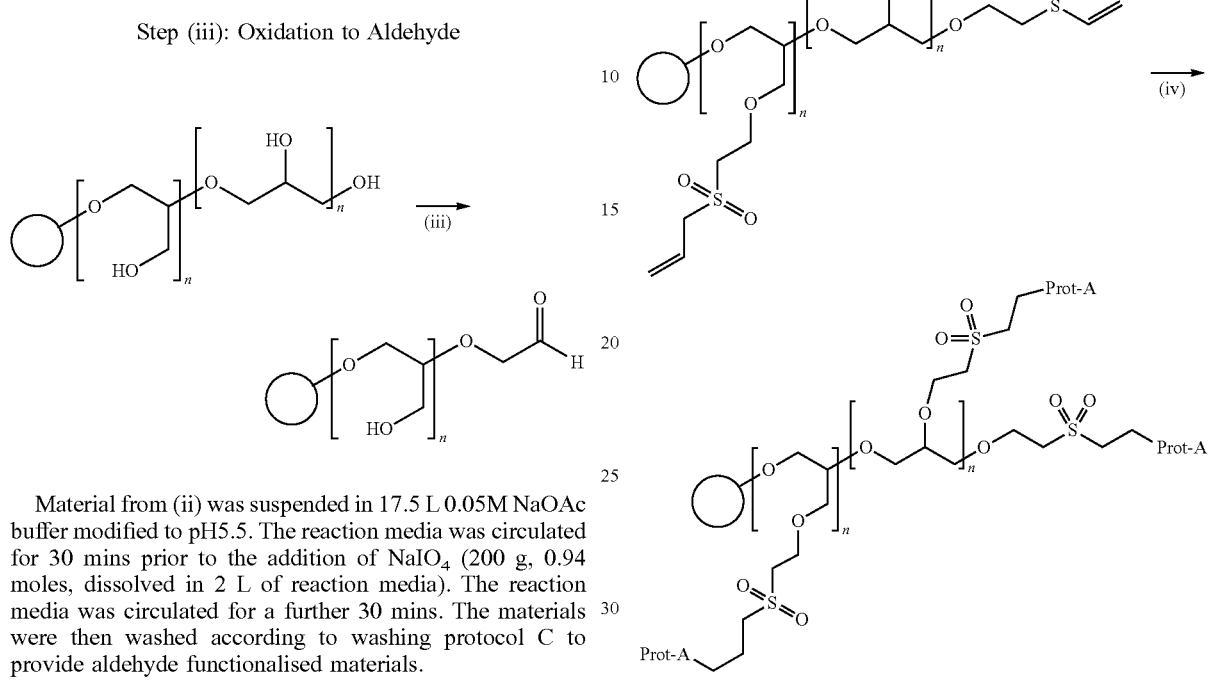

Step (i): Saponification of Cellulose Acetate (CA) to Regenerated Cellulose (RC)

Cellulose acetate sheets (44*32 mm*150 mm) obtained in accordance with the method of Preparative Example 1 were placed into a large beaker containing 5 L of a 0.075M sodium hydroxide solution in 2:1-water:ethanol. The reaction mixture was stirred at room temperature for 48 hours. The materials were then washed according to washing protocol A.

Step (ii): Glycidol Polymerisation

Materials from (i) were suspended in 1 L of 1M NaOH. The reaction media was circulated for 15 minutes prior to the addition of 180 mL Glycidol in a single portion. The reaction media was circulated at room temperature for 16 hours and the material was subsequently washed according to washing protocol B.

Step (iii): Divinylsulfone Derivatisation

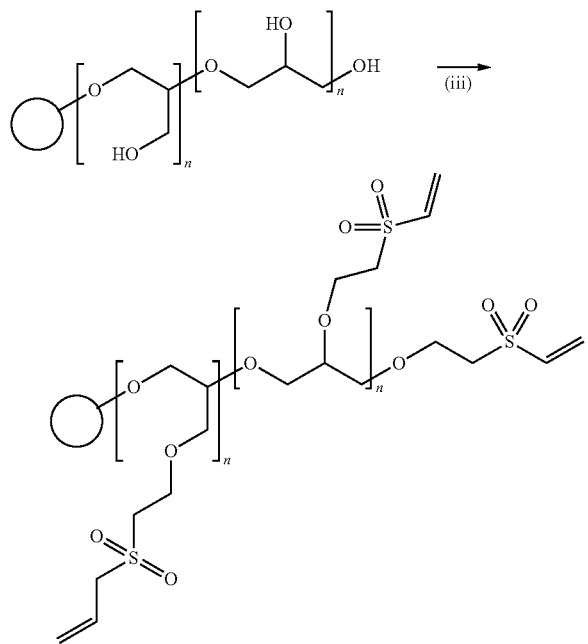

Materials from (ii) were suspended in a solution that consisted of 550 mL H$_2$O with K$_2$CO$_3$ (48.8 g, 0.35 moles) dissolved within it and 50 mL acetonitrile. The reaction media was circulated for 15 minutes prior to the dropwise addition of divinylsulfone (100 ml, 0.86 moles), after which the reaction media was circulated for a further 1.5 hours. The materials were then washed according to washing protocol C.

Step (iv): Protein-A Coupling

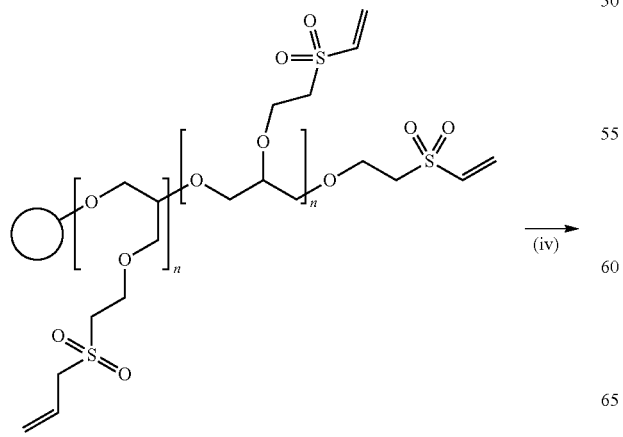

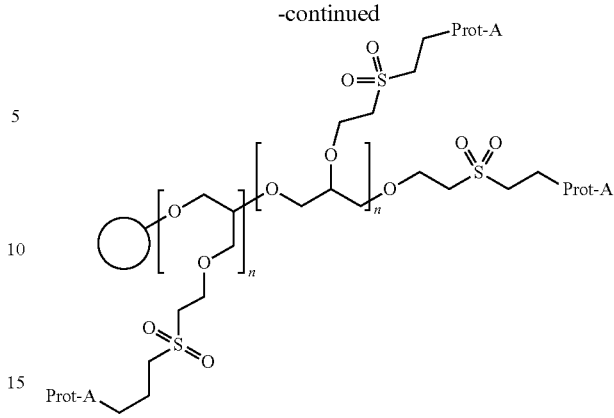

Material from step (iii) was suspended in 70 ml of a protein A solution (50 mg/mL protein A suspension to which is added 668 mg (Na$_2$CO$_3$) and 58 mg NaHCO$_3$ and NaOH to reach pH 11.1). The solution was circulated for 16 hours. The materials were then washed according to washing protocol D.

Reference Example 2—ATRP Crafted, Protein A Coupled Material

Nanofibre materials were derivatised according to the scheme, outlined below:

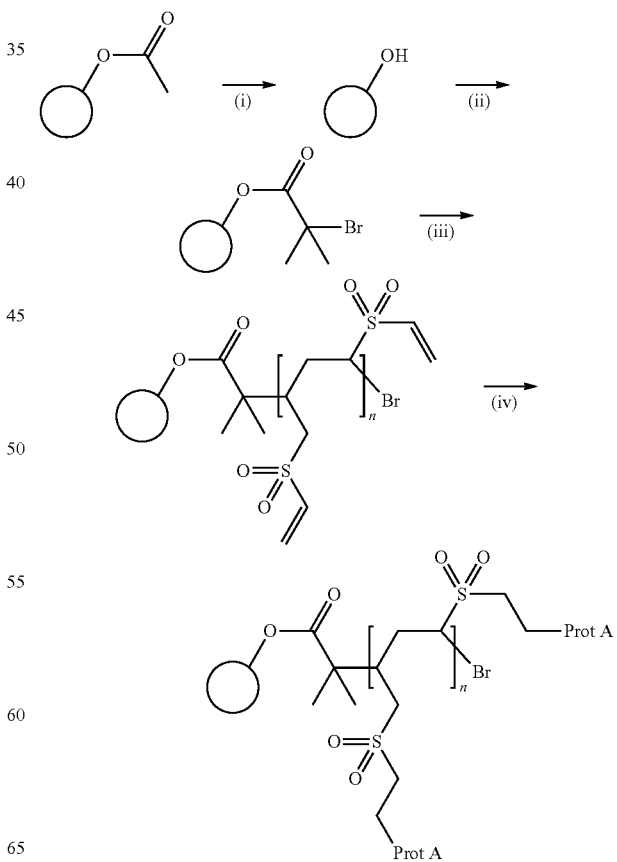

Step (i): Saponification of Cellulose Acetate (CA) to Regenerated Cellulose (RC)

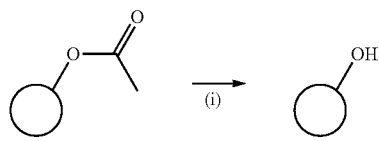

Cellulose acetate sheets (5*65 cm*100 cm) were suspended in 17.5 Ltr of 0.075M NaOH, in 2:1—H$_2$O:EtOH. The reaction media was circulated at room temperature for 48 hours. The materials were then washed according to washing protocol A.

Step (ii): α-Bromoacetylation

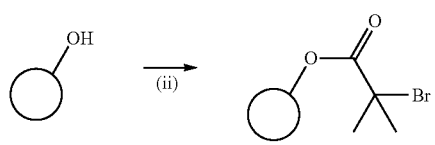

Dried materials from (i) were suspended in 240 ml tetrahydrofuran (THF) with α-bromoisobutyryl bromide (6.24 mL, 50.4 mmol) dissolved in it. The reaction mixture was cooled to 0° C. and then triethylamine (7.2 mL, 51.6 mmol) was added dropwise. The mixture was stirred at 0° C. for 2 hours before being allowed to warm to room temperature. The mixture was stirred at room temperature for a further 16 hours. After this time the derivatised nanofibre materials were washed according to washing protocol A.

Step (iii): ATRP Polymerisation

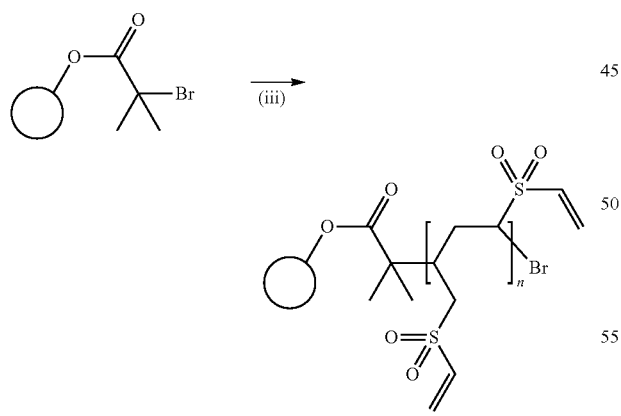

A vessel was charged with 5 mL acetone, 5 mL saturated ascorbic acid, CuBr$_2$ (30 mg, 0.134 mmol) and 1,4,7,10,10-hexamethyltriethylenetetraamine (45 μL, 0.165 mmol). Material from (ii) was suspended in the reaction mixture along with divinylsulfone (2.5 mL, 24.9 mmol). The reaction mixture was gently agitated, using an orbital shaker, at room temperature, for 1 hour. After this time, the nanofibre materials were washed according to washing protocol A.

Step (iv): Protein-A Derivatisation

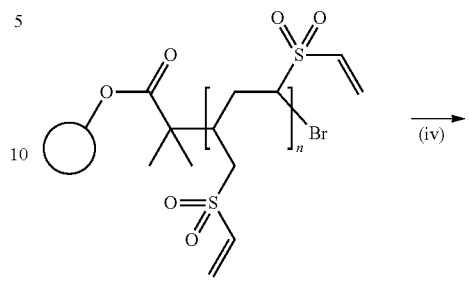

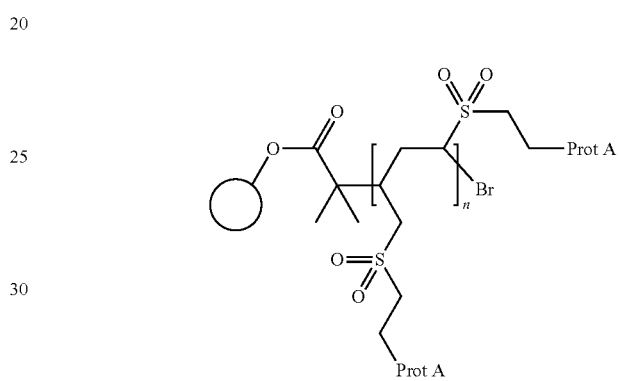

26 mm disks of material from step (iii) were placed in a 6 well plate. To each disk was added 1 mL protein-A solution (50 mg/mL solution as defined above) along with 1 mL of carbonate buffer solution (as defined above). The disks were gently agitated for 16 hours. After this time, the disk were washed using washing protocol D.

Reference Example 3—Trimethylammonium Chloride Functionalization

Nanofibre materials were derivatised according the scheme outlined below:

Step (i): Saponification of Cellulose Acetate (CA) to Regenerated Cellulose (RC)

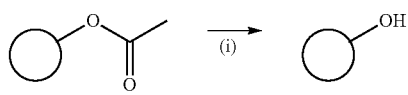

Cellulose acetate sheets (44*32 mm*150 mm) obtained in accordance with the method of Preparative Example 1 were placed into a large beaker containing 5 L of a 0.075M sodium hydroxide solution in 2:1-water:ethanol. The reaction mixture was circulated at room temperature for 48 hours. The materials were then washed according to washing protocol A.

Step (ii): Glycidyltrimethylammonium Chloride Derivatisation

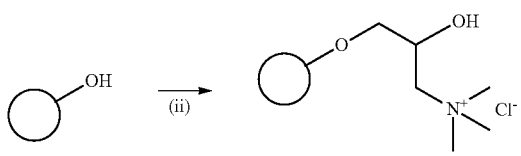

Materials obtained in step (i) were suspended in 1 L 0.5M NaOH. The reaction media was circulated for 15 minutes prior to the addition of glycidyltrimethylammonium chloride (25 mL, 50 mL, 100 mL) in a single portion. The reaction media was circulated for a further 16 hours at room temperature. The materials were then washed according to washing protocol B.

The trimethylammonium chloride content was determined by the following method. 50 mg of material was washed with 100 mL 0.1M HCl solution on a Buchner filter funnel and then with a further 100 mL 0.01M HCl solution. The material was then placed in a drying oven at 75° C. and dried to constant mass before being torn into small pieces and then placed in a 50 mL centrifuge tube. A small magnetic stir bar and 15 mL deionised water were then added along with approximately 1 mL (added via a teat pipette) potassium chromate solution which caused the mixture to become yellow in colour. The mixture was stirred vigorously for 20 minutes before being titrated with 0.1M silver nitrate. The endpoint of the titration is identified by a change in colour from clear yellow to misty brown.

The trimethylammonium chloride content (µmol/g) was calculated as the number of micromoles of silver nitrate added to reach end point/number of grams of nanofibre material used in the titration.

Reference Example 4—Glycidol Grafting

Step (i): Saponification of Cellulose Acetate (CA) to Regenerated Cellulose (RC)

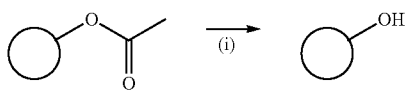

Cellulose acetate sheets (44*32 mm*150 mm) obtained in accordance with the method of Preparative Example 1 were placed into a large beaker containing 5 L of a 0.075M sodium hydroxide solution in 2:1-water:ethanol. The reaction mixture was stirred at room temperature for 48 hours. The materials were then washed according to washing protocol A.

Step (ii): Glycidol Polymerisation

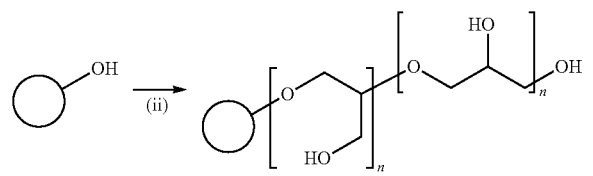

Materials from (i) were suspended in 1 L of 0.5M NaOH. The reaction media was circulated for 15 minutes prior to the careful addition of varying amounts of glycidol (15 mL, 30 mL, 60 mL, 120 mL, 180 mL) in a single portion. The reaction media was circulated at room temperature for 16 hours and the material was subsequently washed according to washing protocol G.

Example 6—Alternative Protocol for Glycidol Grafted, DVS Functionalised, Protein A Coupled Material Nanofibre materials were derivatised according to the scheme outlined below:

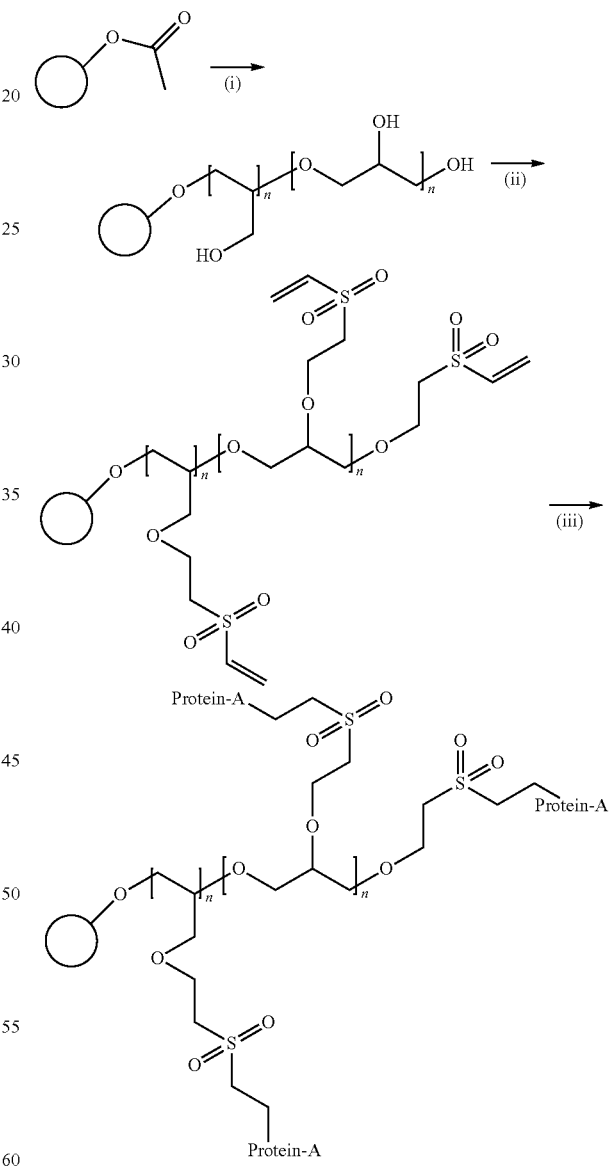

Step (i): Glycidol Polymerisation and Saponification

The glycidol polymerisation and saponification of CA nanofiber materials was effected by taking CA nanofiber material (11×80 mm×50 mm) and suspending it in 1 L de-ionised water. The solvent was circulated for 3 hours before being refreshed with a further 1 L de-ionised water. After repeating this process 4 times, the nanofiber materials were suspended in 350 ml of 1M KOH. The reaction media was circulated for 60 minutes prior to the careful addition of varying amounts of glycidol (100 ml) where 25% of the glycidol was added as a single portion and the remainder added dropwise over 90 minutes. The reaction media was circulated at room temperature for 4 hours and the material was subsequently washed according to washing protocol B.

Step (ii): Divinylsulfone Derivatisation

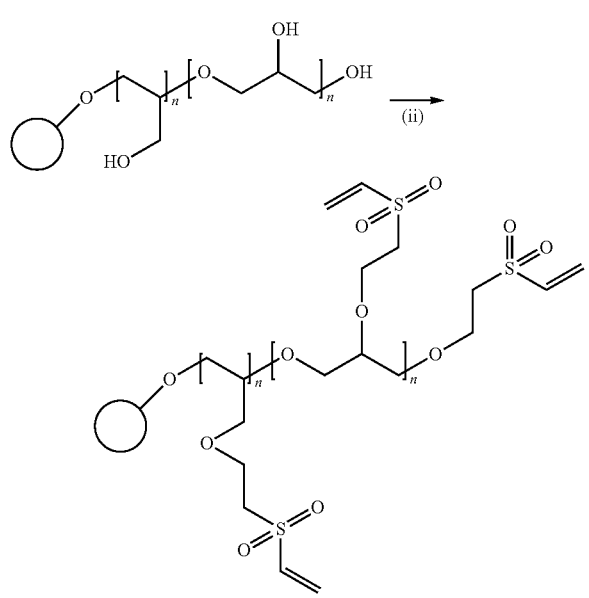

Materials from (i) were suspended in a solution that consisted of 550 mL H$_2$O with K$_2$CO$_3$ (48.8 g, 0.35 moles) dissolved within it and 150 mL acetonitrile. The reaction media was circulated for 15 minutes prior to the dropwise addition of divinylsulfone (100 ml, 0.86 moles), after which the reaction media was circulated for a further 1.5 hours. The materials were then washed according to washing protocol C.

Step (iii): Protein-A Coupling

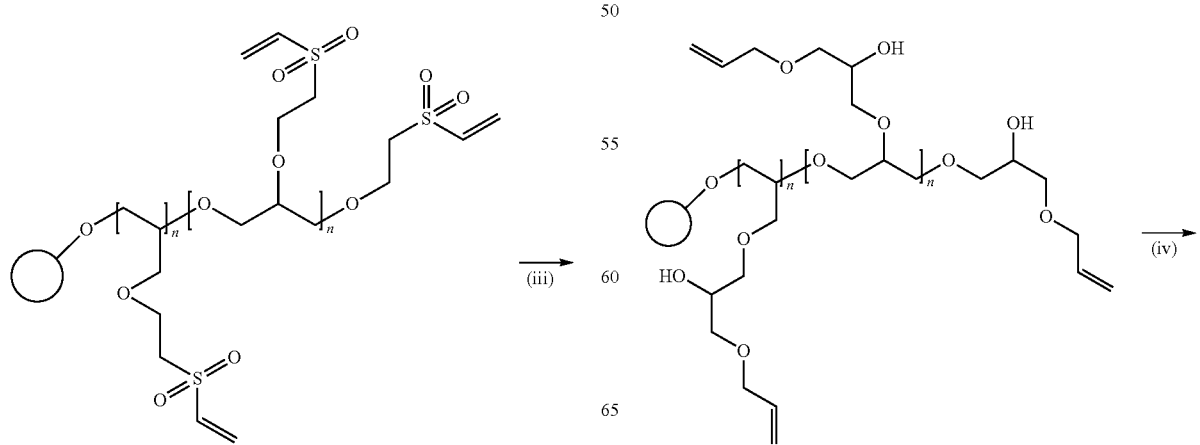

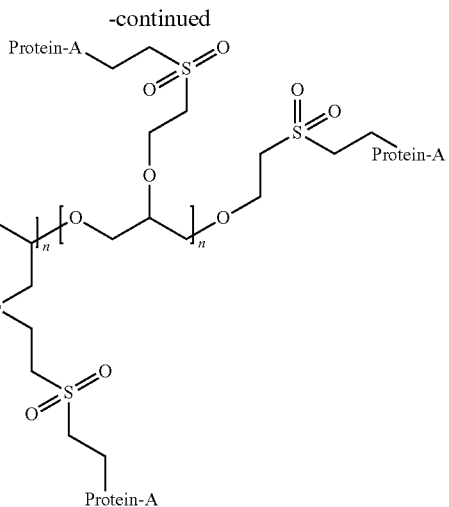

Material from step (ii) was suspended in 70 ml of a protein A solution (50 mg/mL protein A suspension to which is added 668 mg (Na$_2$CO$_3$) and 58 mg NaHCO$_3$ and NaOH to reach pH 11.1). The solution was circulated for 16 hours. The materials were then washed according to washing protocol D.

Example 7—Halohydrin Formation and Derivatisation

Nanofibre materials were derivatised according to the scheme outlined below:

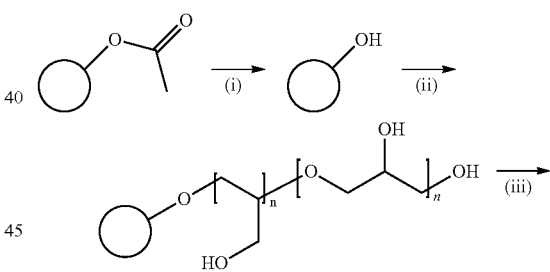

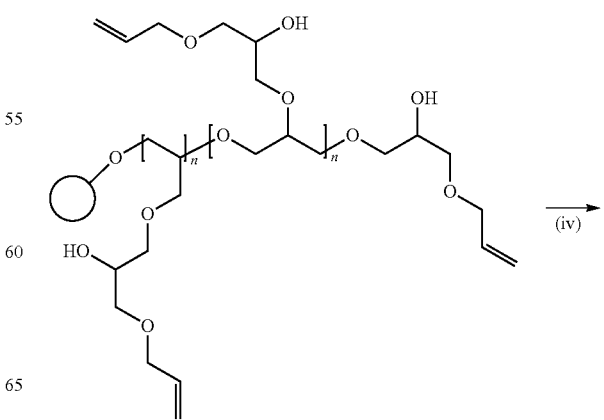

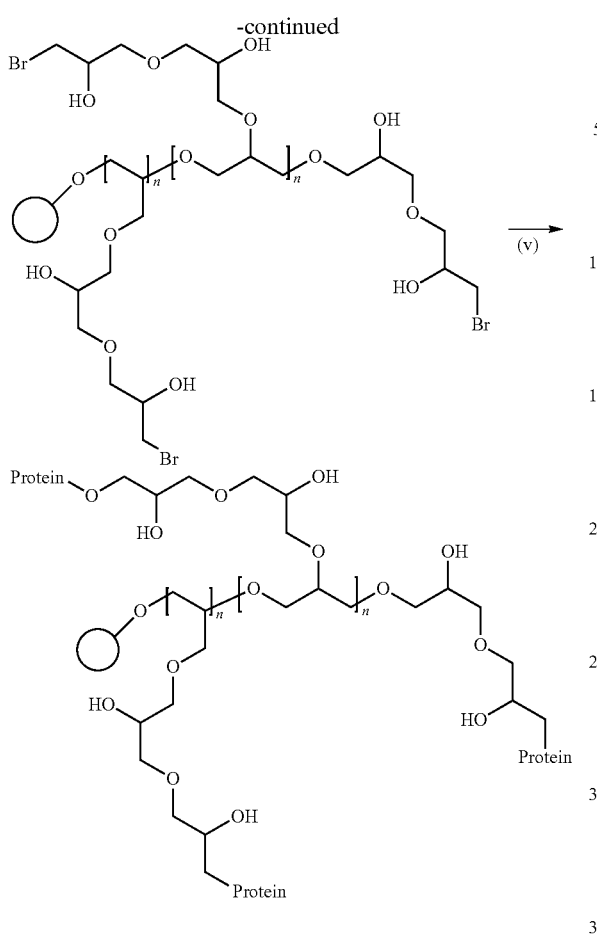

careful addition of varying amounts of Glycidol (60 mL) where 25% of the glycidol was added as a single portion and the remainder added dropwise over 90 minutes. The reaction media was circulated at room temperature for 4 hours and the material was subsequently washed according to washing protocol B.

Step (iii) Allyl Glycidyl Ether Derivatisation

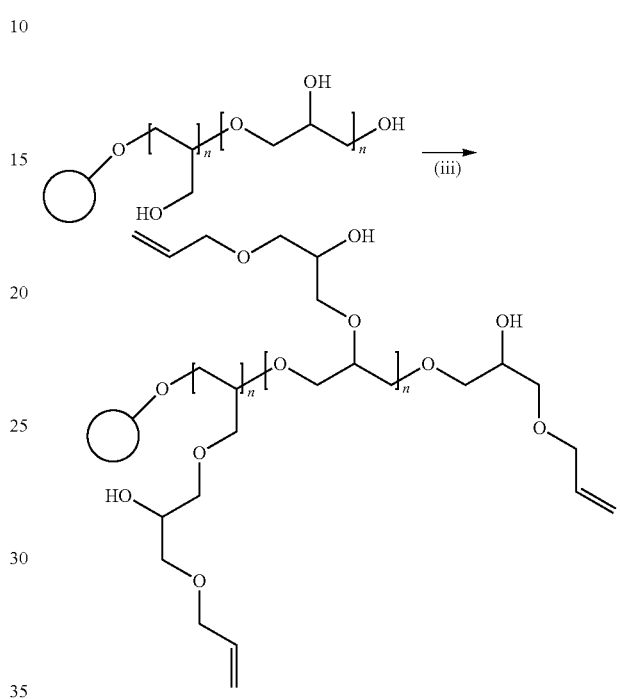

Materials from (ii) were suspended in 1 L 1M KOH. Varying amounts of allylglycidol ether were added (20, 30, 40, 50, 60, 70, 80, 90, 100 ml) by initial addition of 25% of the allylglycidyl ether followed by dropwise addition of the remainder over 90 mins. The reaction was maintained with stirring for 4 hours at room temperature. After this time the materials were subsequently washed according to washing protocol B.

Step (iv): Halohydrin Formation

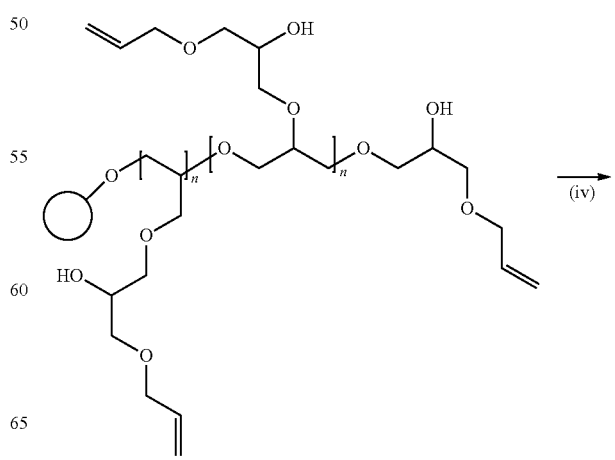

Step (i): Saponification of Cellulose Acetate (CA) to Regenerated Cellulose (RC)

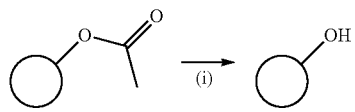

Cellulose acetate sheets (11×80 mm×50 mm) obtained in accordance with the method of Preparative Example 1 were placed into a large beaker containing 5 L of a 0.075M sodium hydroxide solution in 2:1-water:ethanol. The reaction mixture was stirred at room temperature for 48 hours. The materials were then washed according to washing protocol A.

Step (ii): Glycidol Polymerisation

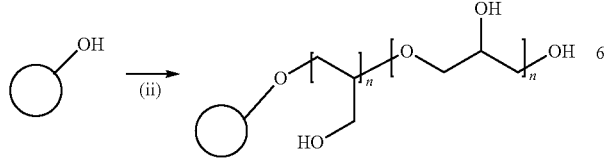

Materials from (i) were suspended in 350 of 1M KOH. The reaction media was circulated for 60 minutes prior to the

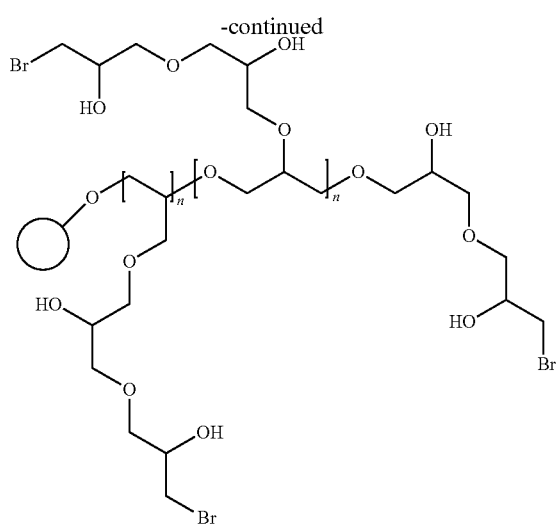

Materials from (iii) were suspended in 1 L 3:1—H$_2$O:MeCN with 25 g N-Bromosuccinimide dissolved in it. The reaction media was circulated through the materials for 4 hours. After this time the reaction media was removed and the remaining materials washed according to washing protocol H.

Step (v): Protein Immobilisation

A single strip of material from step (iv) was placed in a polyethylene pouch. To this pouch was then added 25 ml of protein A solution (50 mg/mL protein A suspension to which is added 668 mg (Na$_2$CO$_3$) and 58 mg NaHCO$_3$ and NaOH to reach pH 11.1). The pouch was sealed and the resulting mixture agitated slowly on an orbital shaker for 16 hours. After this time, the derivatised materials were removed from the pouch and washed according to washing protocol H.

Example 8—Alternative Halohydrin Formation and Derivatisation

Nanofibre materials were derivatised according to the scheme outlined below:

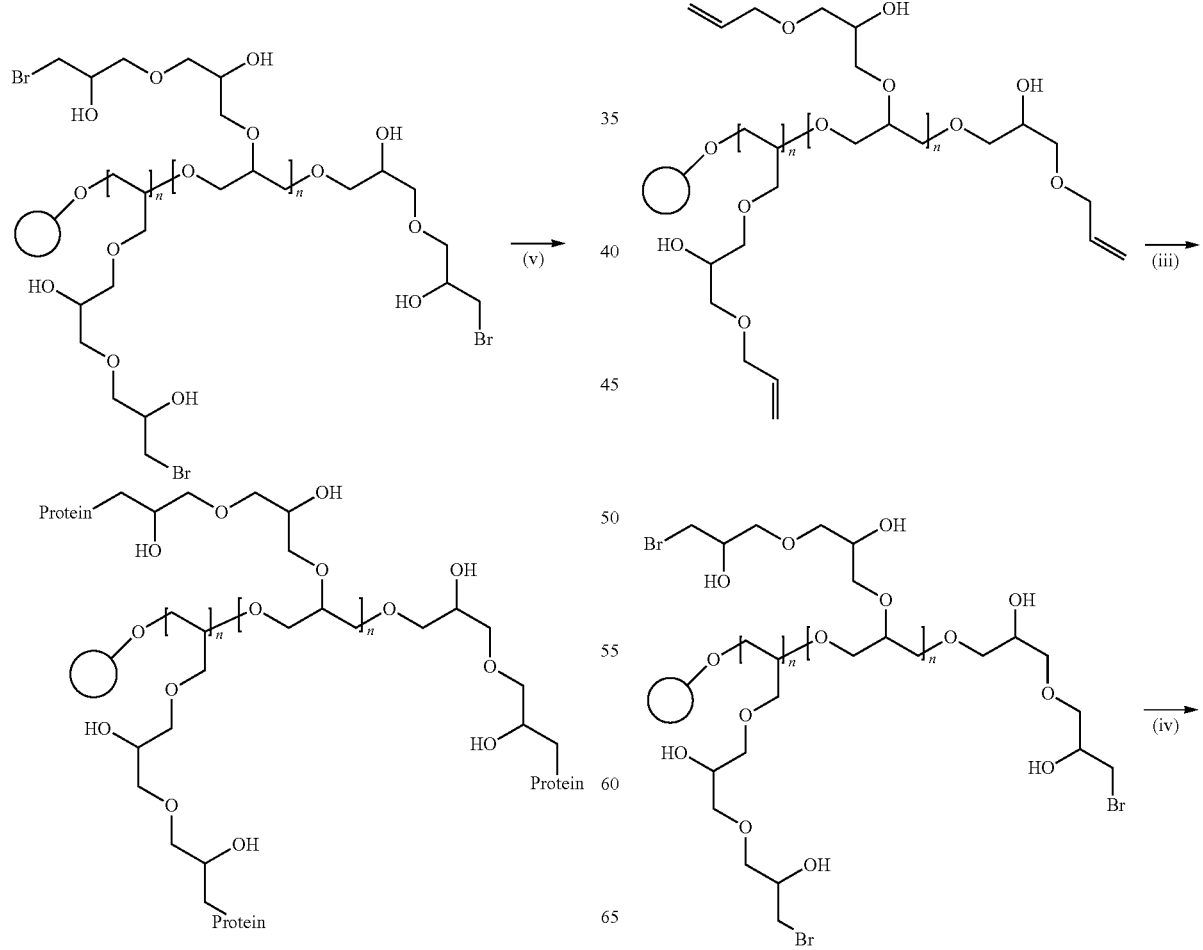

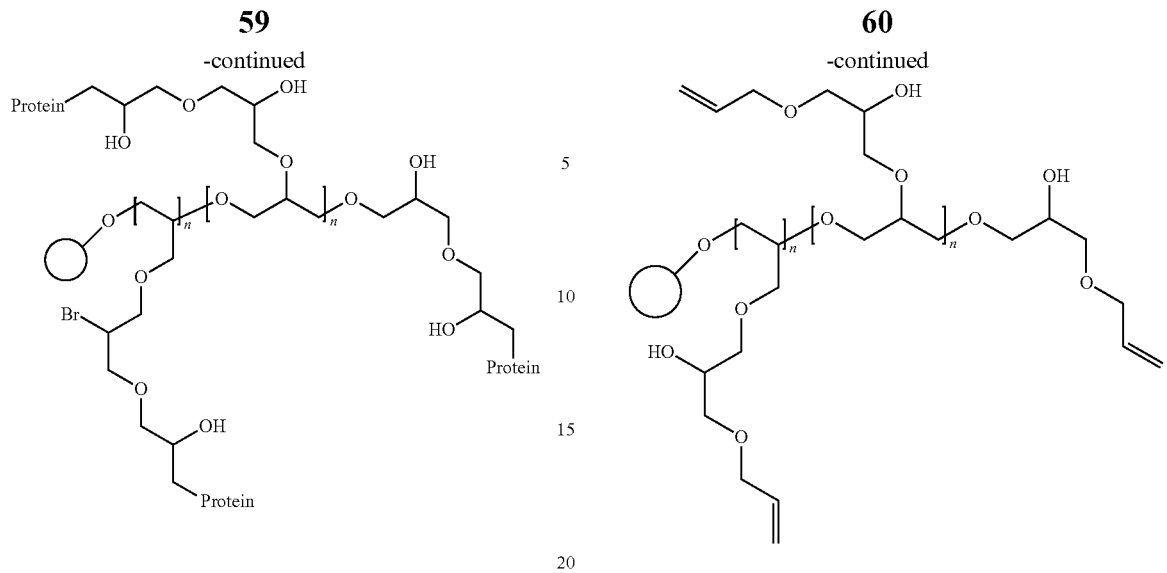

Step (i): Glycidol Polymerisation and Saponification

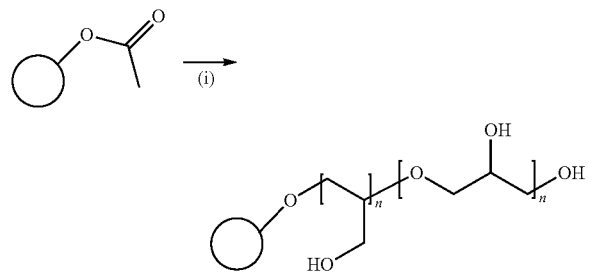

The glycidol polymerisation and saponification of CA nanofiber materials was effected by taking CA nanofiber material (6×120 mm×90 mm) and suspending it in 1 L de-ionised water. The solvent was circulated for 3 hours before being refreshed with a further 1 L de-ionised water. After repeating this process 4 times, the nanofiber materials were suspended in 350 mL of 1M KOH. The reaction media was circulated for 5 minutes prior to the careful addition of 100 mL glycidol where 25% of the glycidol was added as a single portion and the remainder added dropwise over 90 minutes. The reaction media was circulated at room temperature for 4 hours and the material was subsequently washed according to washing protocol B.

Step (ii) Allyl Glycidyl Ether Derivatisation

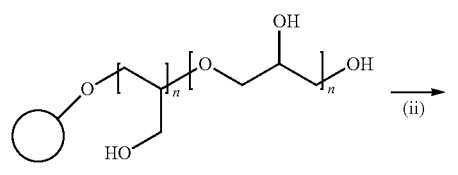

Materials from (i) were suspended in 350 L 1M KOH. Varying amounts of allyl glycidyl ether were added (20, 30, 40, 50, 60, 70, 80, 90, 100 mL) by initial addition of 25% of the allyl glycidyl ether followed by dropwise addition of the remainder over 90 mins. The reaction was maintained with stirring for 6 hours at room temperature. After this time the materials were subsequently washed according to washing protocol B.

Use of lower amounts of allyl glycidyl ether produced materials having particularly beneficial flow characteristics. Use of higher amounts of allyl glycidyl ether produced materials having higher binding capacities.

Step (iii): Halohydrin Formation

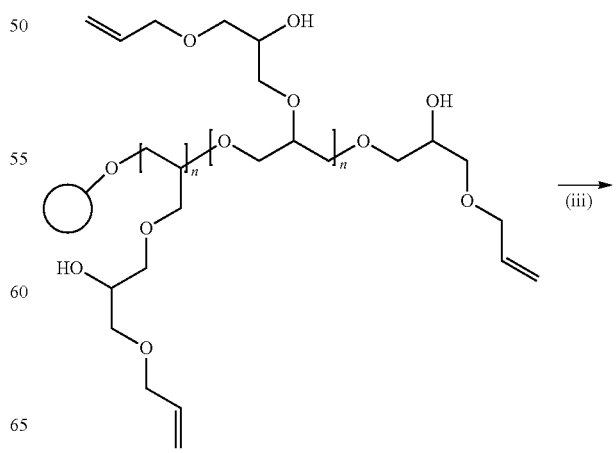

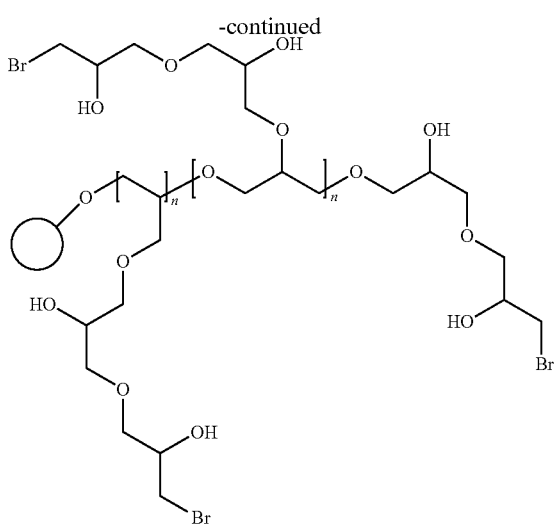

Materials from (ii) were suspended in 1 L 3:1—H$_2$O:MeCN with 25 g N-Bromosuccinimide dissolved in it. The reaction media was circulated through the materials for 4 hours. After this time the reaction media was removed and the remaining materials washed according to washing protocol H.

Step (iv): Protein Immobilisation

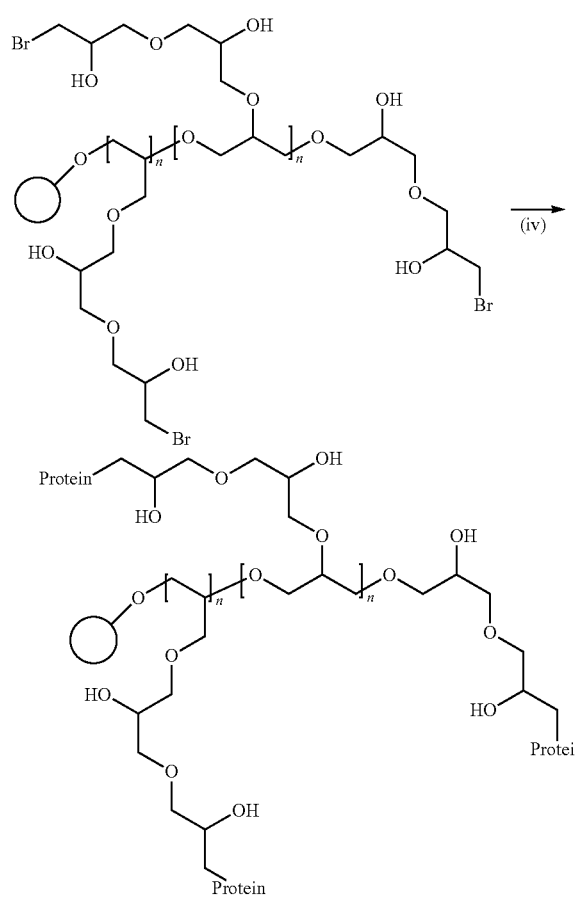

A single strip of material from step (iii) was placed in a polyethylene pouch. To this pouch was then added 25 mL of protein A solution (50 mg/mL protein A suspension to which is added 668 mg (Na$_2$CO$_3$) and 58 mg NaHCO$_3$ and 1M NaOH (to reach pH 11.1)). The pouch was sealed and the resulting mixture agitated slowly on an orbital shaker for 16 hours. After this time, the derivatised materials were removed from the pouch and washed according to washing protocol H.

II Analytical Methods

Example 9—Determination of Dynamic Binding Capacity

Loading material was passed through a selected functionalised nanofibre disc contained within a holder on an AKTA Pure system (GE Healthcare). The material was loaded under a determined membrane volume per minute flowrate (mV/min) until the concentration after the holder outlet exceeded 10% of that loaded as determined by the UV flow cell. Accounting for dead volumes in the system and the holder device the total amount of protein loaded onto the disc at the 10% breakthrough was determined through analysis of the chromatogram in the Unicorn software (GE Healthcare).

For anion exchange material the loading material was 1 mg/mL BSA in 10 mM Tris to pH 8. For cation exchange material the loading material was 1 mg/mL lysozyme in sodium acetate pH 4.7 10 mM.

Example 10—Determination of Resistance to Flow

The pressure drop ($\Delta P$) across the selected functionalised nanofibre material was determined using the AKTA Pure system (GE Healthcare). A buffer of 10 mM Tris (pH 8) was passed through a functionalised nanofibre disc contained within a holder. The flowrate at which the delta column pressure ($\Delta P$) equalled 0.5 MPa was recorded.

III Analyses and Comparisons of Specific Materials

Example 11—Relationship Between Charge Density and Trimethylammonium Functionalisation with the Addition of a Separate Grafting Step in Accordance with the Invention Materials were fabricated and tested in accordance with Reference Example 3 to produce trimethylammonium functionality to enable the material to operate as an anion exchanger. These were compared to grafted materials of the invention, produced and assayed according to Example 1.

Figure 4:
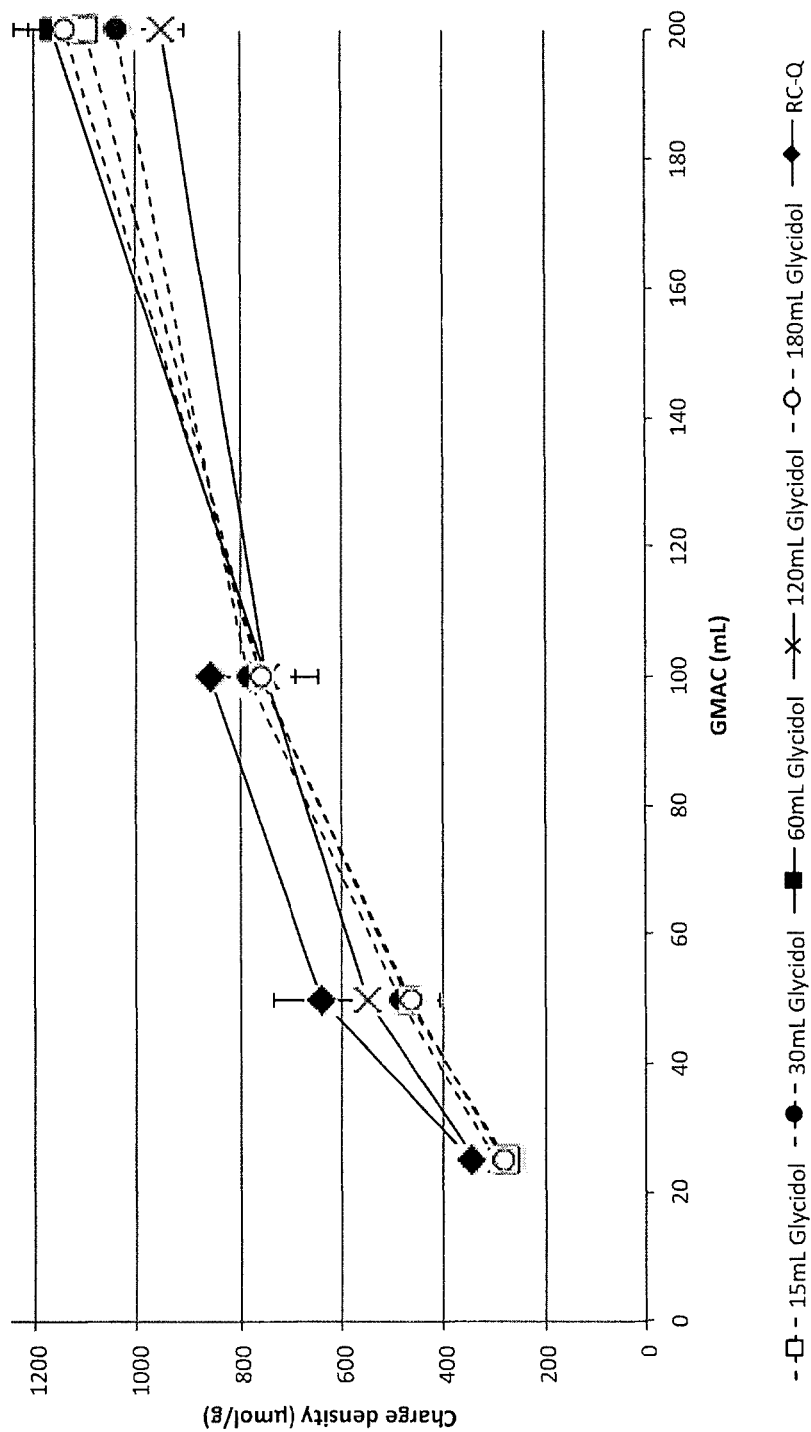
FIG. 4 shows the effect of increasing the degree of polymer grafting and amount of trimethylammonium functionalisation agent on charge density for a number of materials prepared in accordance with the present invention.

The charge densities obtained for the trimethylammonium functionalised materials are shown in FIG. 4. An average value for each of the datapoints in FIG. 4 is plotted in FIG. 5.

Figure 5:
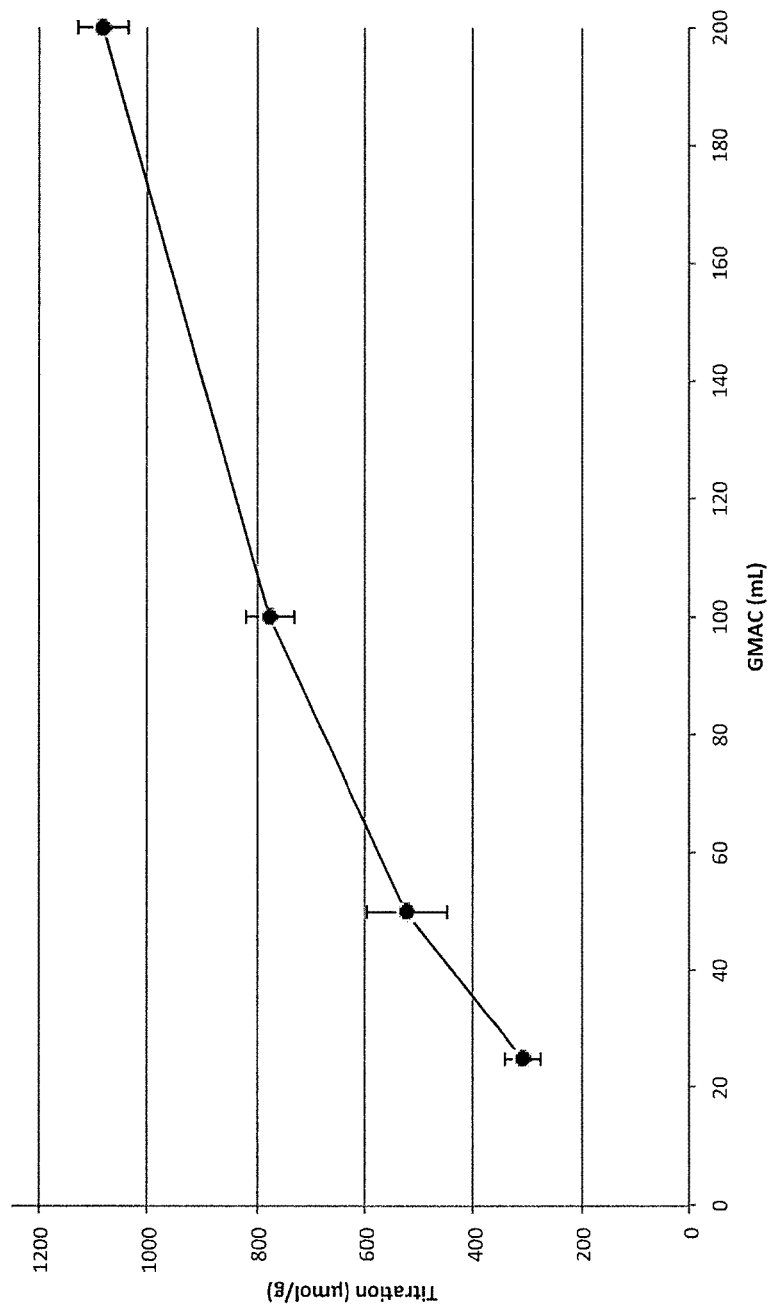
FIG. 5 shows an average for the values displayed in FIG. 4.

It is clear from FIG. 4 and FIG. 5 that when a set amount of the functionalisation reagent GMAC is used, increasing the graft amount does not significantly affect the charge density.

Reference Example 5—Relationship Between Charge Density and Trimethylammonium Functionalisation Materials were fabricated and tested in accordance with Reference Example 3 to produce trimethylammonium functionality to enable the material to operate as an anion exchanger. The results are shown in FIG. 2.

Figure 2:
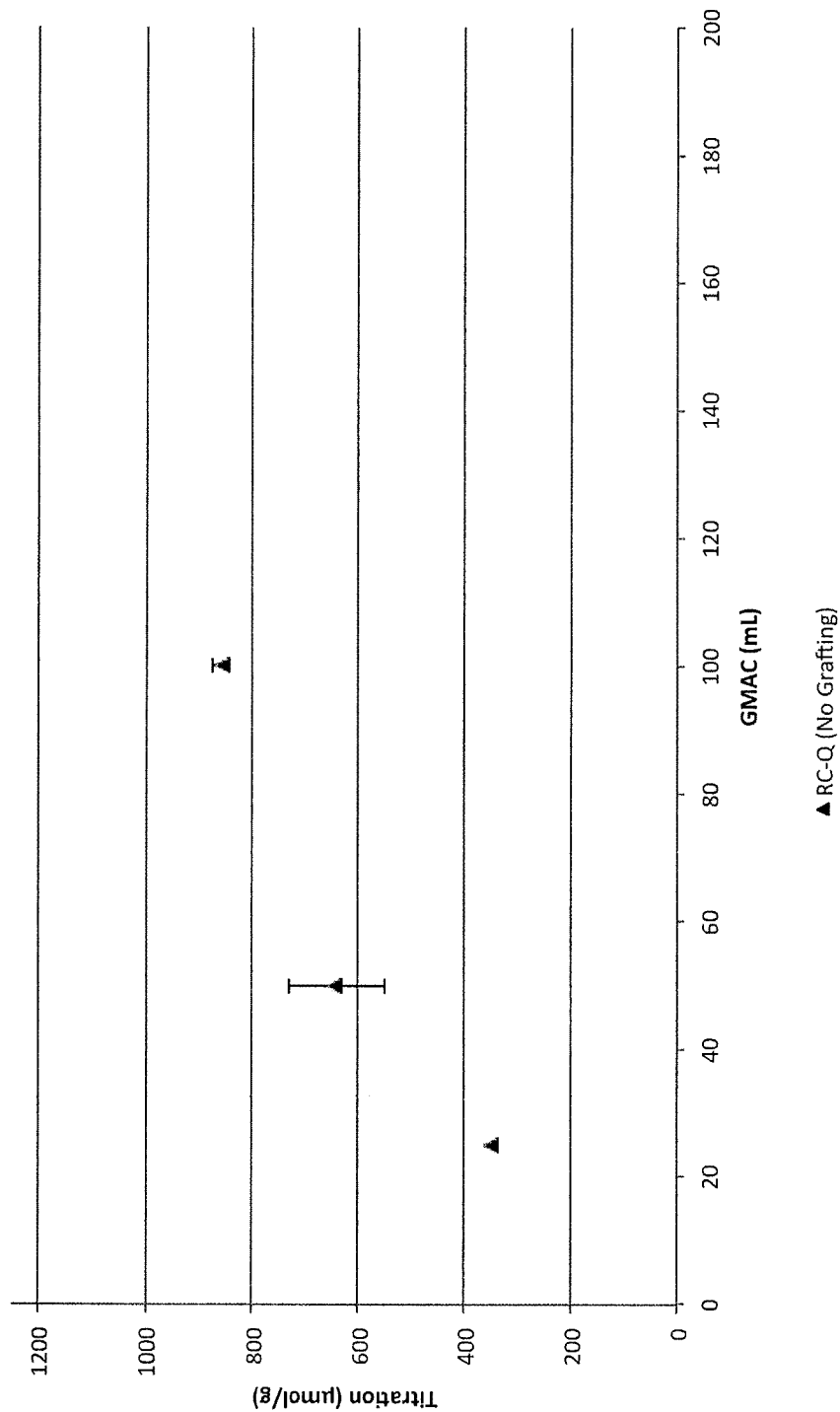
FIG. 2 shows the effect of increasing the amount of functionalisation agent on charge density of trimethylammonium functionalised material in the absence of a grafting step.

It can be seen from FIG. 2 that increasing the amount of functionalisation agent (glycidyltrimethylammonium chloride) increases the charge density where there has been no grafting step.

Example 12—Relationship Between Dynamic Binding Capacity (DBC) and Trimethylammonium Functionalisation with the Addition of a Separate Grafting Step in Accordance with the Invention The dynamic binding capacities (DBCs) for the same materials assayed in Example 11 were determined using the method in Example 9.

Figure 6:
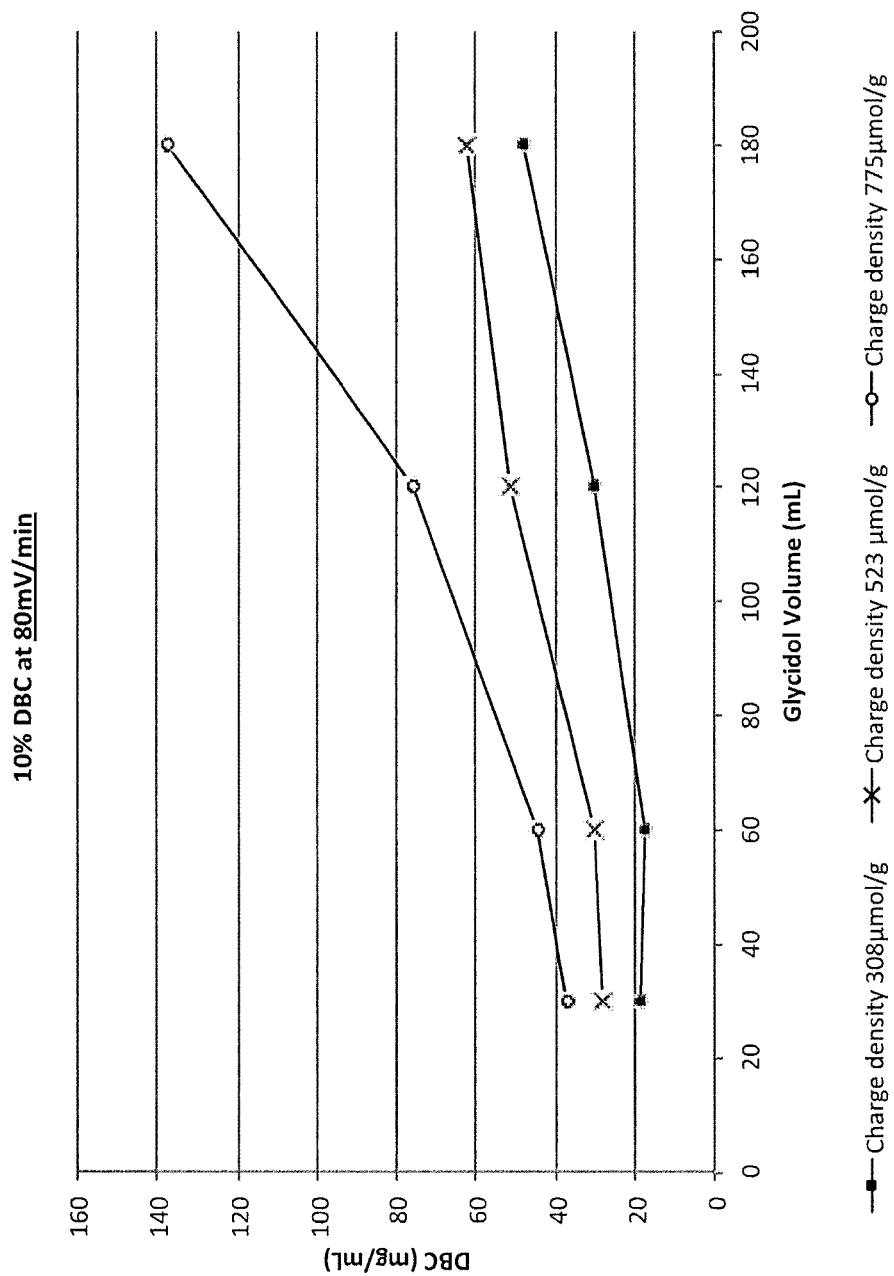
FIG. 6 shows the effect of increasing polymer grafting on dynamic binding capacity (DBC) at set charge densities for a number of trimethylammonium functionalised materials prepared in accordance with the invention.
Figure 7:
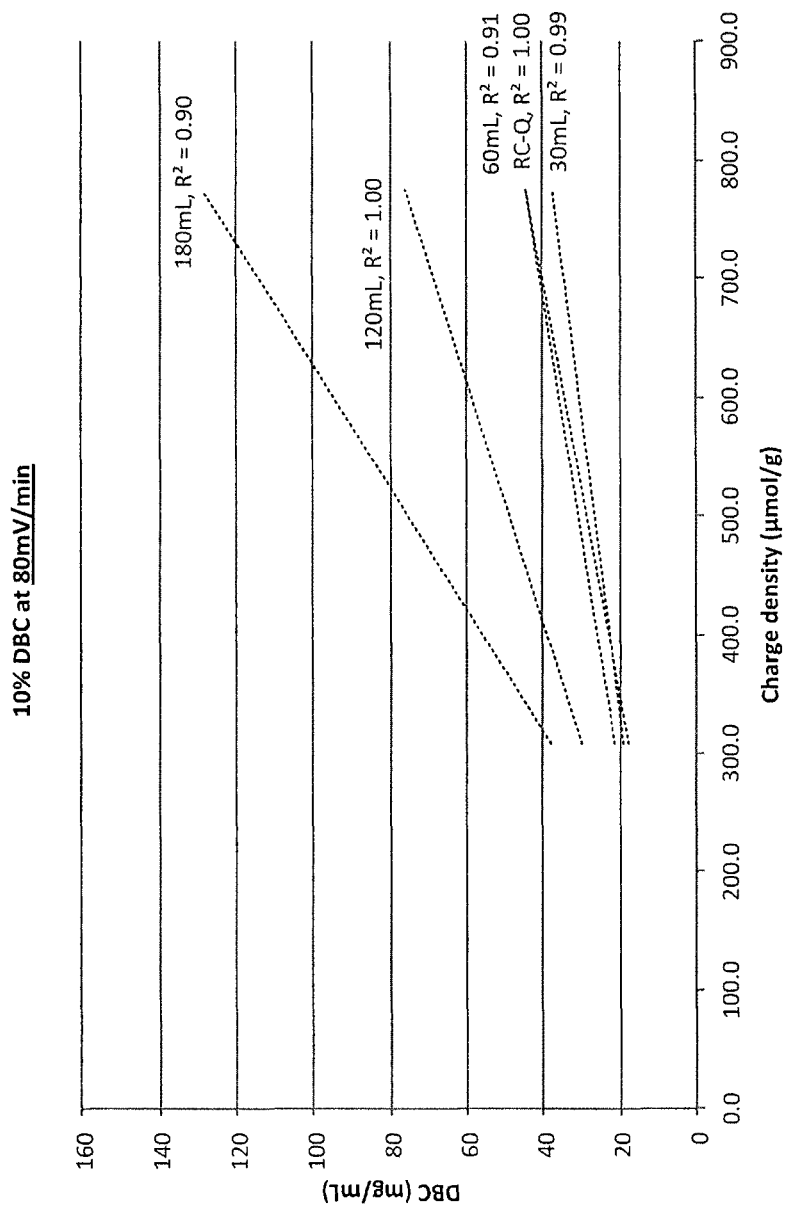
FIG. 7 shows the effect of increasing the charge density on dynamic binding capacity (DBC) at set polymer grafts for a number of materials prepared in accordance with the invention, compared to ungrafted materials.

DBC plots of materials of the invention fabricated according to Example 1 are shown in FIG. 6. The DBCs of these materials are compared to those that have not undergone the two-step grafting process of the invention (i.e. the materials of Reference Example 3) in FIG. 7.

It can be seen that the binding capacity of the grafted materials produced according to the invention are over 4 fold greater than those where no grafting has been used. Conversely to what is seen in Reference Example 6 (below) for the non-grafted materials, it is clear that for a grafted material where charge density remains constant, increasing the graft amount gives rise to increases in the binding capacity of the material.

Reference Example 6—Relationship Between Charge Density and Dynamic Binding Capacity (DBC) for Trimethylammonium Chloride Material Materials were fabricated and tested in accordance with Reference Example 3 to produce trimethylammonium functionality to enable the material to operate as an anion exchanger. Dynamic binding capacities of these materials were determined according to Example 9.

Figure 3:
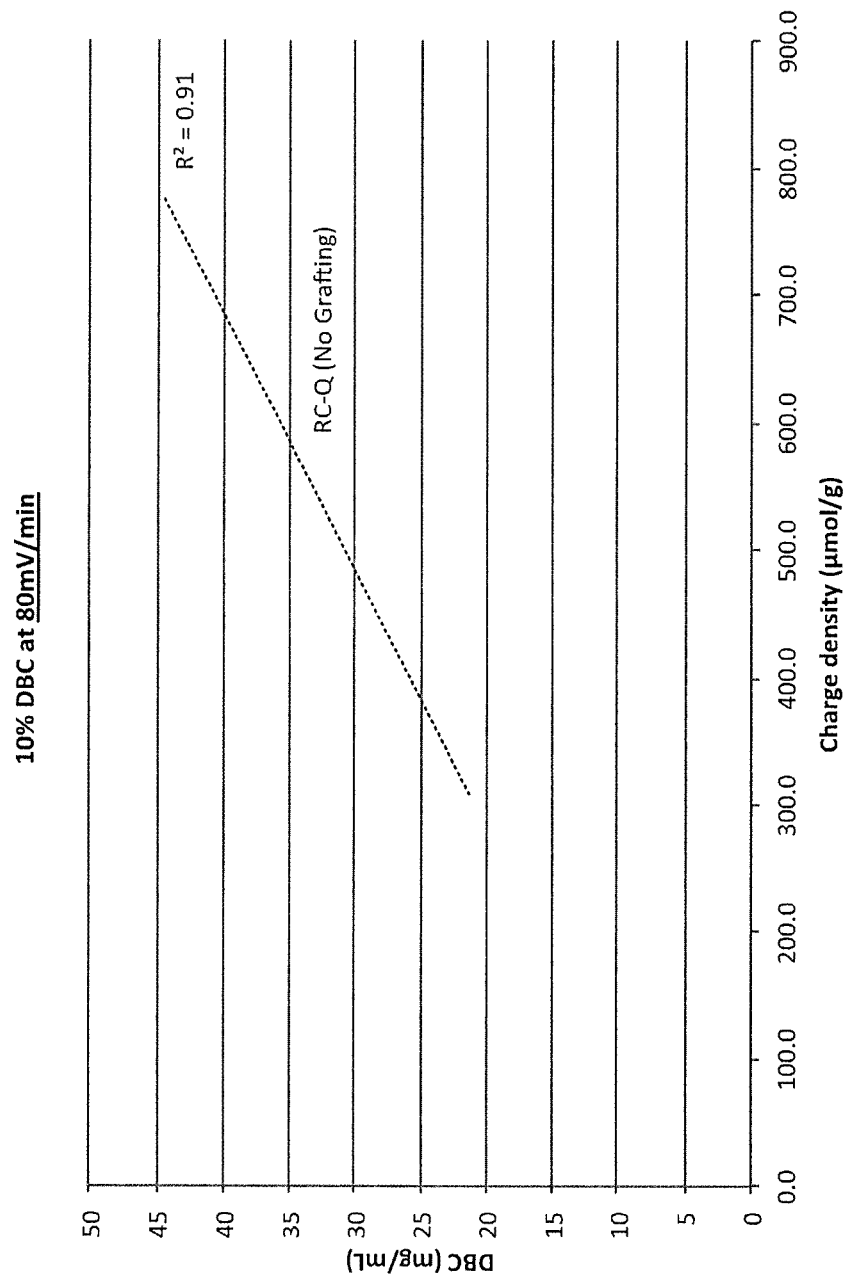
FIG. 3 shows the effect of increasing charge density on dynamic binding capacity (DBC) of trimethylammonium functionalised material in the absence of a grafting step.

The results are shown in FIG. 3.

As expected by someone skilled in the art, it can be seen from FIG. 3 that increasing the amount of functionalisation agent, glycidyltrimethylammonium chloride, increases the binding capacity where there has been no grafting step.

Example 13—Relationship Between Charge Density and Sulfonic Acid (S) Functionalization with the Addition of a Separate Grafting Step in Accordance with the Invention Materials of the invention were given S functionality to enable the material to work as cation exchange material and assayed in accordance with Example 2.

Figure 8:
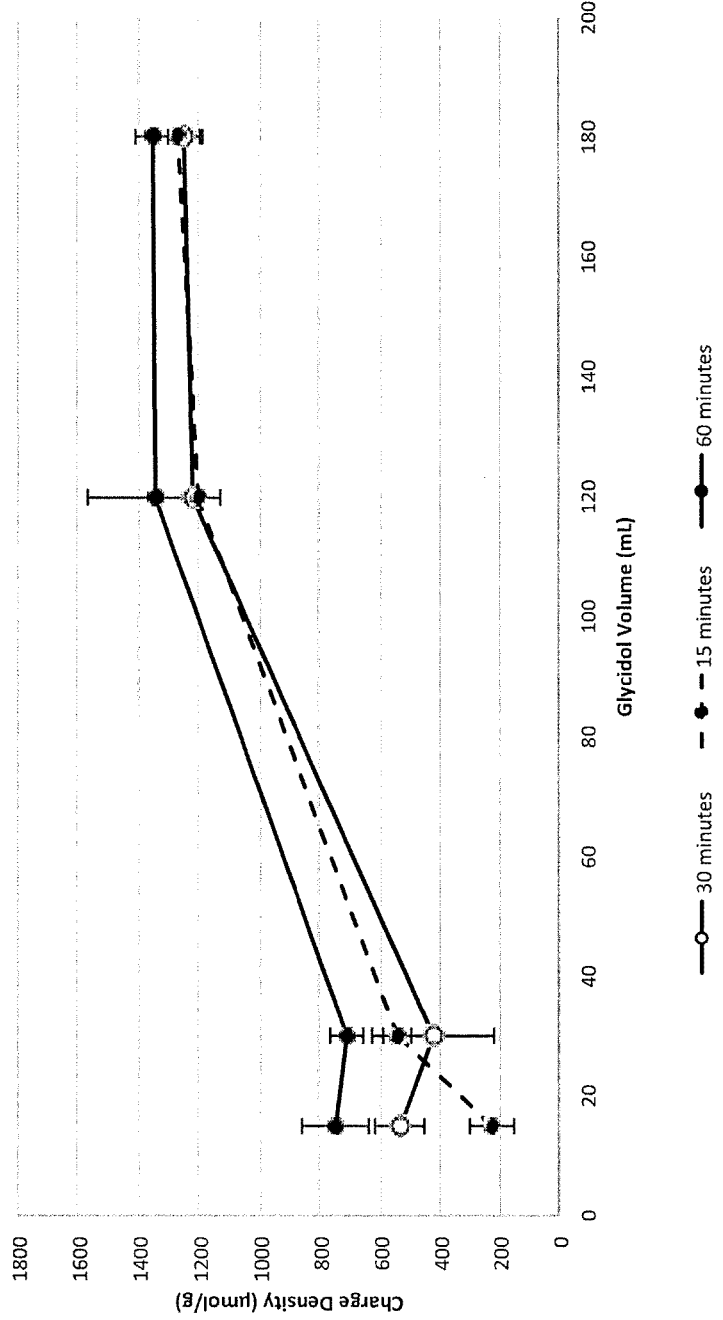
FIG. 8 shows the effect of increasing the degree of polymer grafting and functionalisation reaction time on charge density for glycidol/Sulfonic Acid functionalised material.

The sulfonic acid content of the materials was determined as set out in Example 2. The results are shown in FIG. 8. It can be observed that it is the grafting step rather than the functionalisation step that has the bigger impact on the charge density of the materials.

Example 14—Relationship Between Dynamic Binding Capacity (DBC) and Sulfonic Acid (S) Functionalisation with the Addition of a Separate Grafting Step in Accordance with the Invention The dynamic binding capacities (DBCs) for the materials fabricated according to Example 2 were determined using the method in Example 9. The results are shown in FIG. 9.

Figure 9:
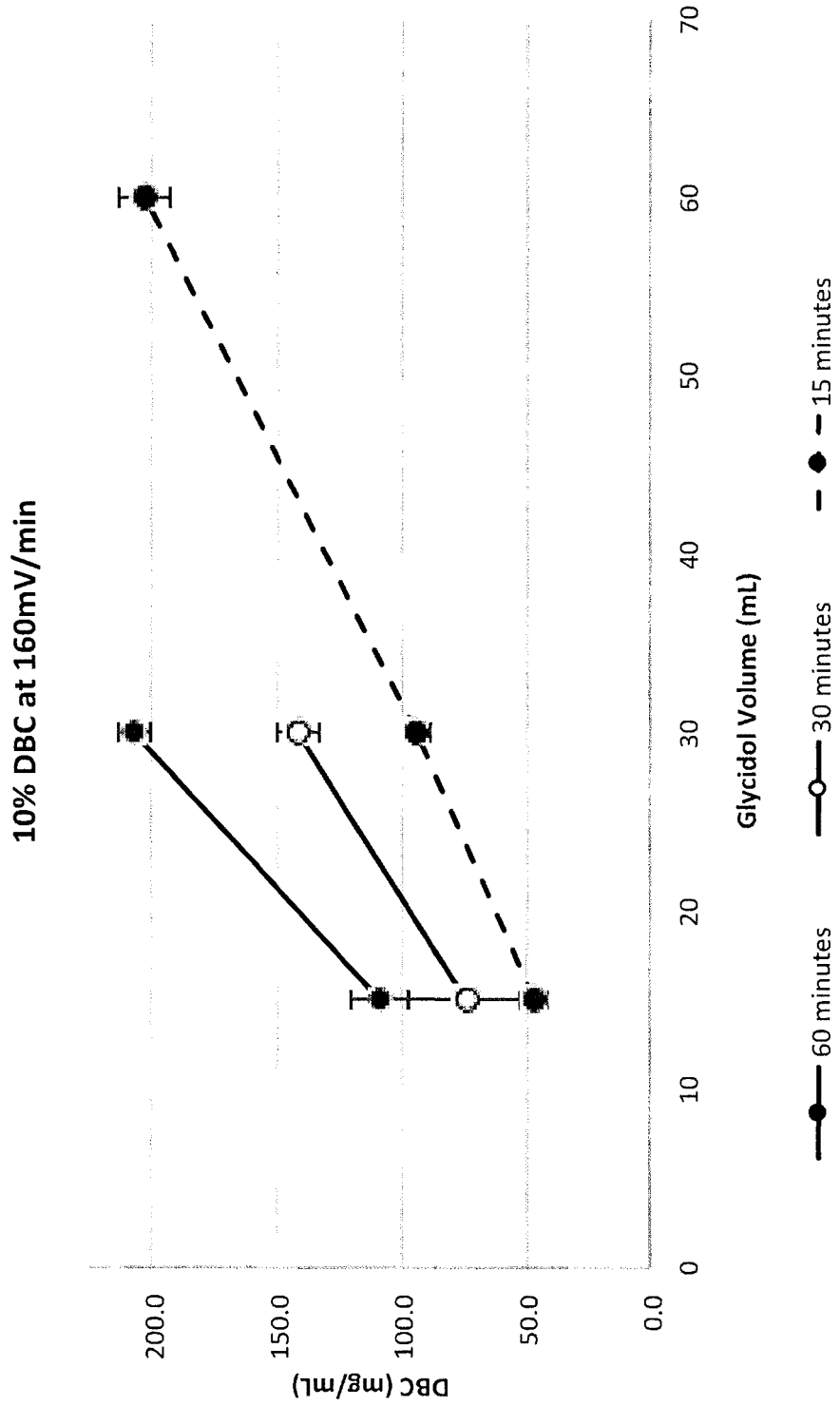
FIG. 9 shows the impact of an independent grafting step on the dynamic binding capacity of glycidol/Sulfonic Acid functionalised material in accordance with the invention.

It can be seen from FIG. 9 that as seen in Example 13 there is also interdependency between the grafting step and functionalisation step. These materials created in accordance with the invention yield binding capacities between 47 and 207 mg/mL at a flowrate of 160 membrane volumes (mV)/min.

Example 15—Relationship Between Dynamic Binding Capacity (DBC) and Carboxymethyl (CM) Functionalisation with the Addition of a Separate Grafting Step in Accordance with the Invention Materials of the invention were given carboxymethyl (CM) functionality to enable the material to work as cation exchange material in accordance with Example 3. The dynamic binding capacities (DBCs) for these materials relating to the invention were determined using the method in Example 9. The results are shown in FIG. 10.

Figure 10:
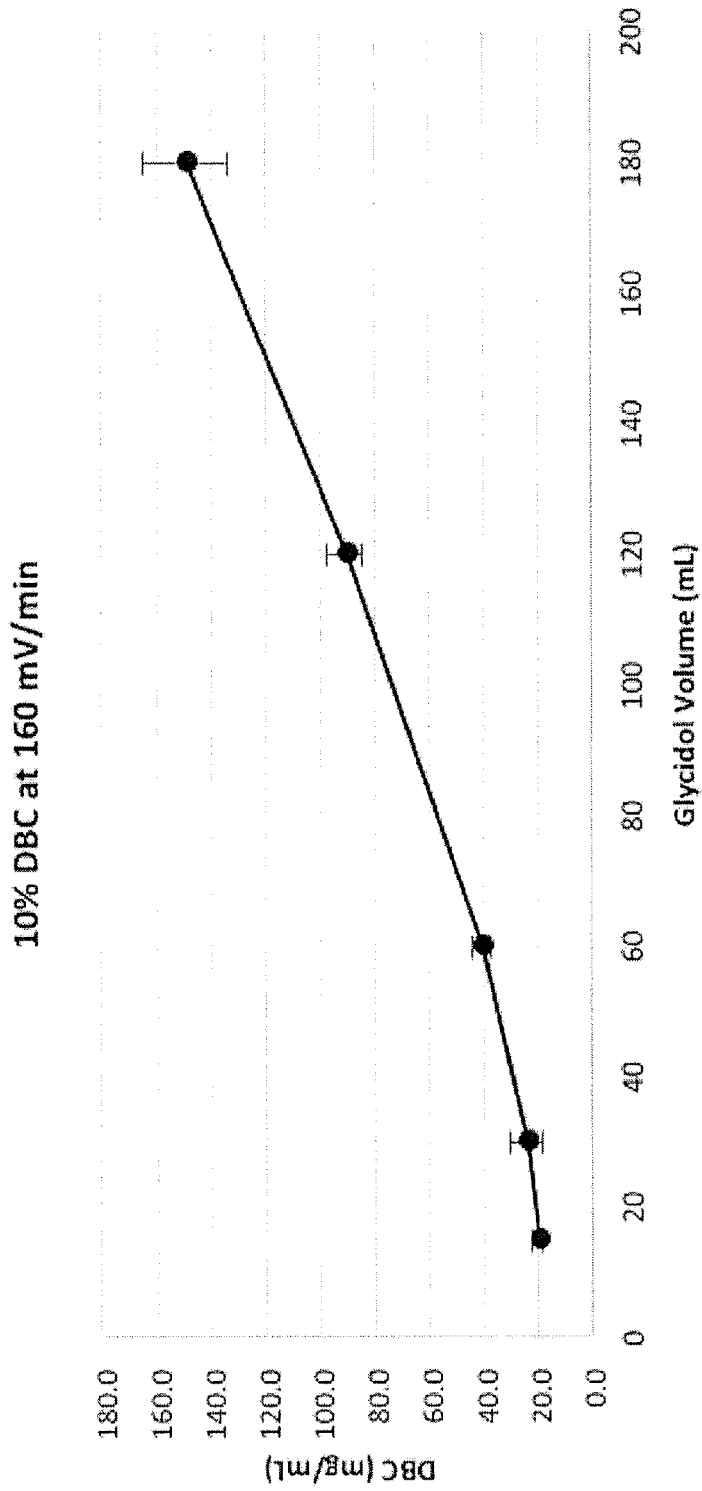
FIG. 10 shows the impact of grafting on the dynamic binding capacity (DBC) of glycidol/CarboxyMethyl functionalised material in accordance with the invention.

It can be seen from FIG. 10 that materials fabricated in accordance with the invention can reach binding capacities between 20 and 149 mg/mL at a flowrate of 160 mV/min.

Reference Example 7—Binding Capacity of Dimethylamino-Derivatised Materials Using ATRP Grafting Materials in accordance with the invention were given dimethylamino functionality to enable the material to work as anion exchange membranes in accordance with Reference Example 1. The dynamic binding capacities (DBCs) for these materials of the invention were determined using the method in Example 9.

Example 16—Relationship Between Degree of Polymer Grafting and Resistance to Flow at Set Charge Densities The resistance to flow of the same materials assayed in Example 11 were determined using the method of Example 10.

Figure 11:
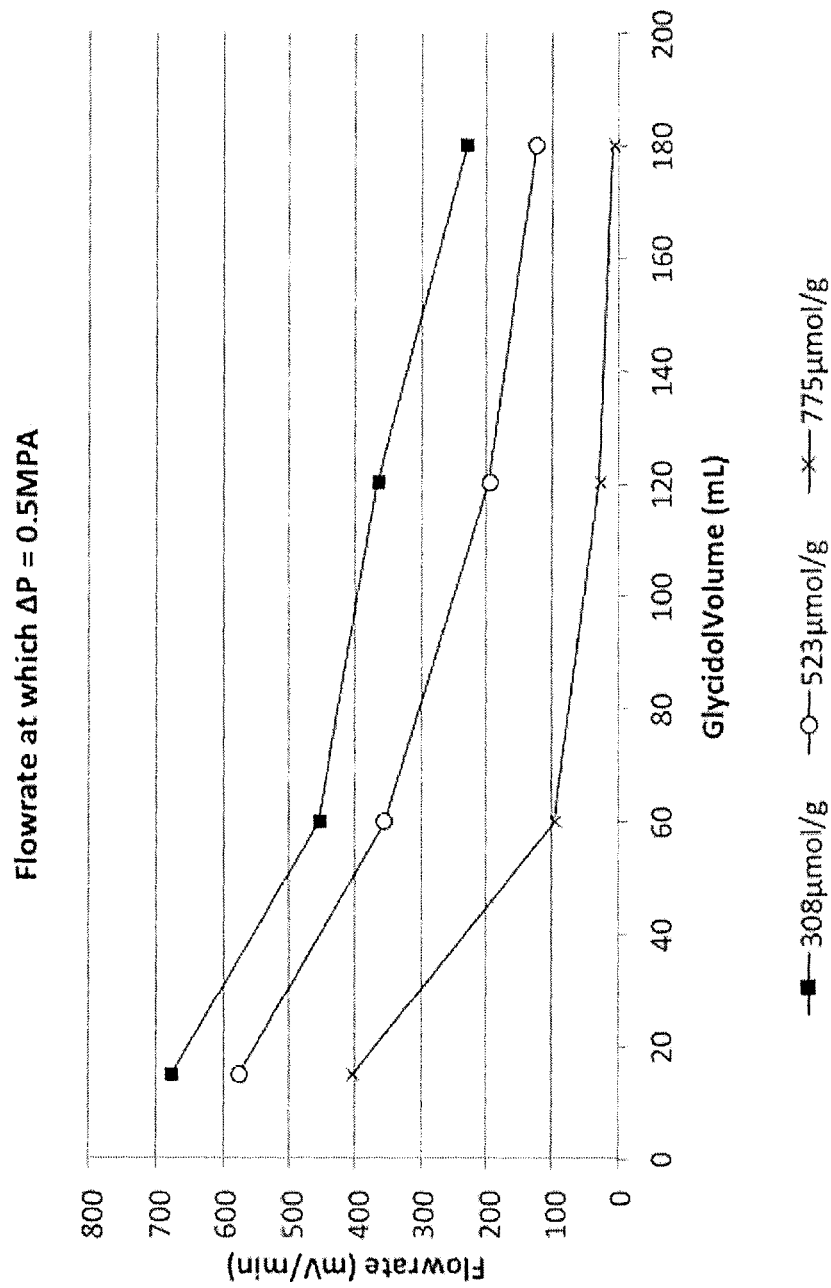
FIG. 11 shows the effect of increasing charge density and the degree of polymer grafting on resistance to flow for a number of materials prepared in accordance with the invention.

The results from this assay are shown in FIG. 11. This shows a clear relationship between degree of polymer grafting and resistance to flow for the charge-functionalised materials. A clear relationship between charge density and resistance to flow can also be seen.

Reference Example 8—Determination of OH Density after Grafting

A sample of material produced in accordance with Reference Example 4 was removed and washed with copious amounts of water (using a Buchner funnel) and then dried to constant mass. The sample was then weighed and shredded into a 50 mL centrifuge tube. To the tube was added exactly 10 mL of a p-toluenesulfonylisocyanate (20 mL p-toluenesulfonylisocyanate in 500 mL acetonitrile). A small stir bar was added to the centrifuge tube which was then sealed and placed in a water bath at 60° C. and stirred for 60 min. After this time the sample was diluted with 20 ml $H_2O$ and stirred for a further 10 mins. 40 mL iso-propanol was then added and the sample stirred for a further 10 minutes before being titrated using 0.481M $Bu_4NOH$ on the autotitrator (use method CA OH titration).

Two inflection points are observed in the titration curve. The first occurring at approximately pH5.5 (VEP1) and the second at approximately pH 9.5 (VEP2). The amount of free OH present in the sample was calculated thus:

$$OHV = ((VEP2 - VEP1 * f * c(TBAH) * MA))/ms$$

Figure 13:
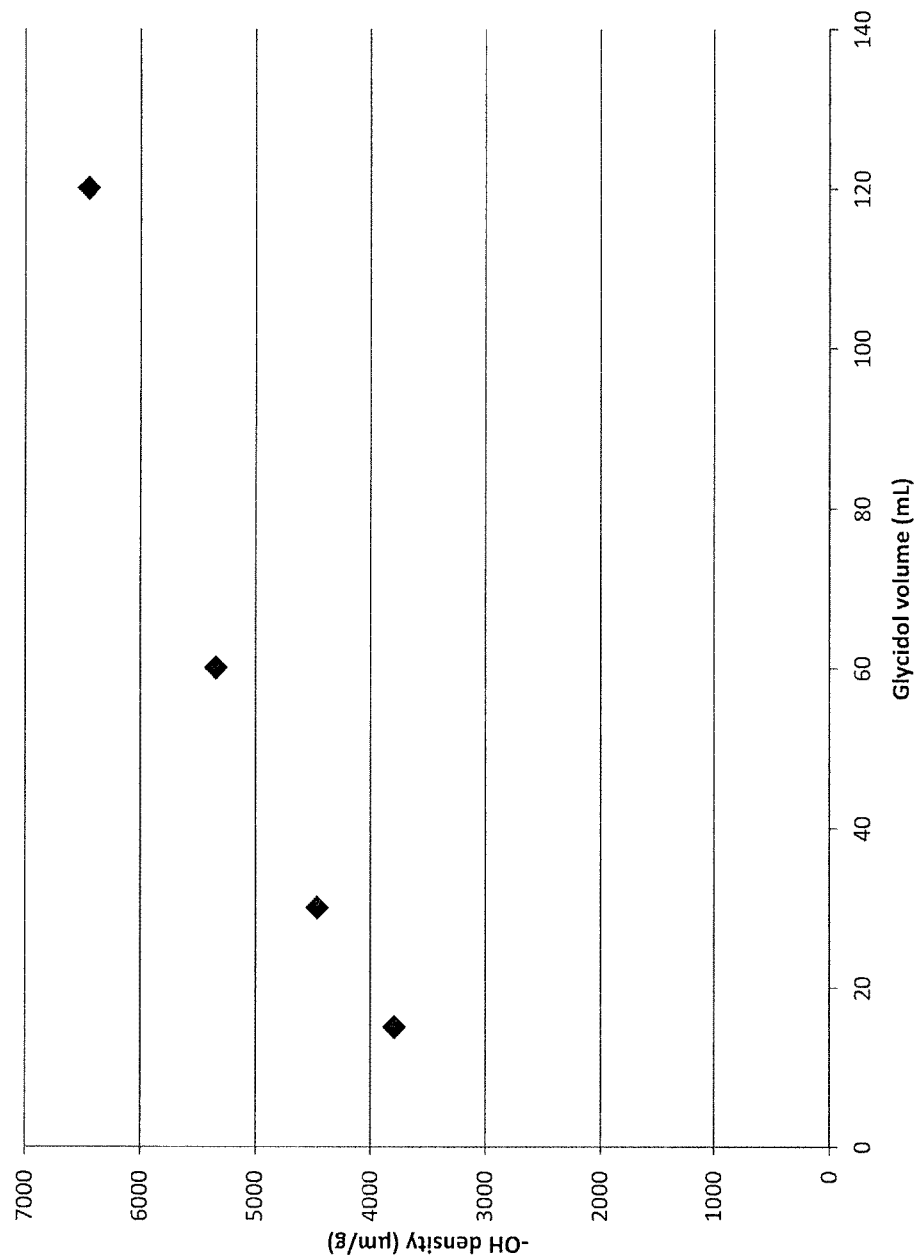
FIG. 13 shows the effect of increasing the amount of glycidol reagent on the density of —OH groups in the grafted product.

OHV: Hydroxy value of sample in KOH/g sample
VEP1: Titrant consumption until first equivalence point in mL
VEP2: Titrant consumption until second equivalence point in mL
C(TBOAH): Concentration of the Tetrabutylammonium chloride in mol/L
F: Correction factor (titre) without unit
Ma: molecular weight ok KOH; here 56.11 g/mol
Ms: Sample size in g Analyses of the materials produced in accordance with Reference Example 5 show that for this particular substrate and grafting method, varying the amount of glycidol reagent gives materials with an —OH group density upwards of 6000 µmol/g. This is shown in FIG. 13.

Reference Example 9—Effect of Increasing Polymer Grafting on Resistance to Flow for Uncharged Materials Materials were treated with differing amounts of glycidol in accordance with Reference Example 4 and the resistance to flow of each material (and for ungrafted RC material) measured using the assay as set out in Example 10. The results are shown in FIG. 12.

Figure 12:
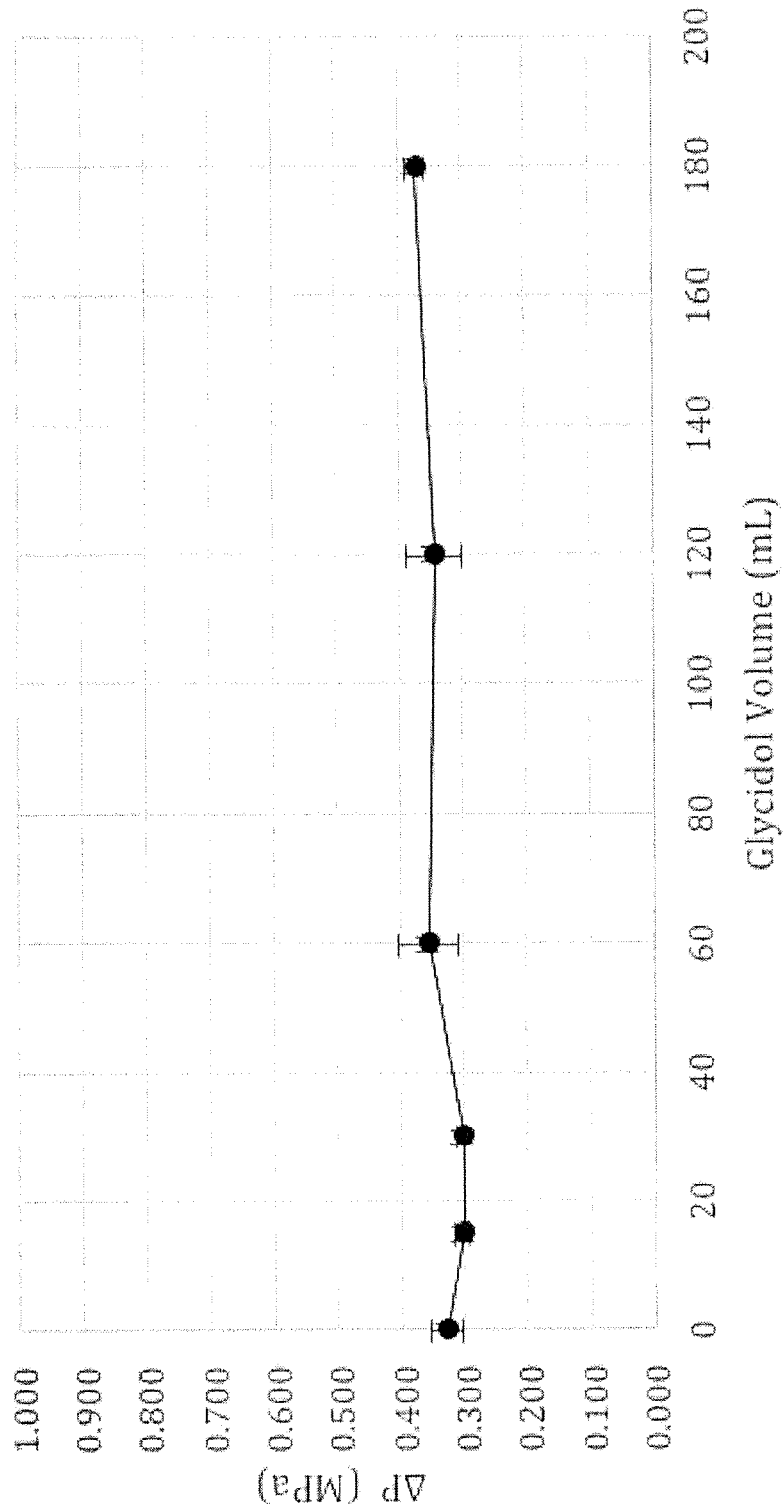
FIG. 12 shows the effect of increasing the degree of polymer grafting on resistance to flow in a number of uncharged materials.

It can be seen from FIG. 12 that there is no discernable increase in the pressure drop with respect to flow for uncharged materials having different degrees of grafting. It can therefore be concluded that there is no discernible pore clogging in the materials with increased degrees of grafting. It is clearly observable that, once a material is functionalised with charged groups a relationship between grafting amount and resistance to flow is seen, as reported in Example 16 (above) and FIG. 11.

Example 17—Productivity of Materials of the Invention

Capacity (DBC) and productivity values for a number of materials of the invention were determined. The results obtained are set out in Table 1.

TABLE 1

Capacities and productivities of materials claimed in the invention

| | Capacity 10% DBC (mg/mL) | Residence time (s) | Flowrates (mV/min) | Productivity (mg/mL/min) |
|---|---|---|---|---|
| No-graft Q | 40 | 0.4 | 160 | 6,400 |
| Glycidol Q | 160 | 0.4 | 160 | 25,600 |
| Glycidol S | 207 | 0.4 | 160 | 33,120 |
| Glycidol CM | 149 | 0.4 | 160 | 23,840 |
| ATRP dimethylamino material (Reference Example) | 11 | 0.3 | 240 | 2,640 |
| Glycidol DVS Protein A | 34 | 0.75 | 80 | 2,720 |
| Alternate Glycidol DVS Protein A | 60 | 0.75 | 80 | 4,800 |
| Glycidol Aldehyde Protein A | 11 | 0.4 | 160 | 1,760 |
| Alternative Halohydrin formation and derivatisation | 40 | 0.75 | 80 | 3,200 |
| ATRP Protein A (Reference Example) | 8 | 0.4 | 240 | 1,920 |

Comparative Example 1

Binding capacities, residence times and productivity values for a variety of commercially available porous bead materials were obtained from the manufacturers. The results obtained are set out in Table 2.

TABLE 2

Examples of porous bead capacities and productivities

| | Functionality | Support type | Capacity | Residence time (min) | Productivity (mg/mL/min) |
|---|---|---|---|---|---|
| GE Healthcare Life Sciences: Capto Q[1] | Anion Exchange | Agrose bead | 100 mg BSA/mL[2] | 1 | 100 |
| GE Healthcare Life Sciences: Capto S[3] | Cation Exchange | Agrose bead | 120 mg lysozyme/mL[4] | 1 | 120 |
| GE Healthcare Life Sciences: MabSelectSuRe[5] | Protein A (affinity) | Agrose bead | 35 mg human IgG/ml[6] | 2.4 | 15 |

TABLE 2-continued

Examples of porous bead capacities and productivities

| | Functionality | Support type | Capacity | Residence time (min) | Productivity (mg/mL/min) |
|---|---|---|---|---|---|
| GE Healthcare Life Sciences: MabSelectSuRe LX[7] | Protein A (affinity) | Agrose bead | 60 mg human IgG/ml[8] | 6 | 10 |

[1]Accessed 30 Mar. 2016: https://www.gelifesciences.com/gehcls_images/GELS/ Related%20Content/Files/1335359522418/litdoc11002576_20120514181545.PDF
[2]Dynamic binding capacity at 10% breakthrough as measured at a residence time of 1 minute, 600 cm/h in a Tricorn 5/100 column with 10 cm bed height in a 50 mMTris-HCl buffer, pH 8.0.
[3]Accessed 30 Mar. 2016: https://www.gelifesciences.com/gehcls_images/GELS/ Related%20Content/Files/1335359522418/litdoc11002576_20120514181545.PDF
[4]Dynamic binding capacity at 10% breakthrough as measured at a residence time of 1 min, 600 cm/h in a Tricorn™ 5/100 column with 10 cm bed height, in a 30 mM sodium phosphate buffer, pH 6.8.
[5]Accessed 30 Mar. 2016: http://www.gelifesciences.com/webapp/wcs/stores/servlet/catalog/en/GELifeSciences-uk/products/AlternativeProductStructure_17372/17543801
[6]Determined at 10% breakthrough by frontal analysis at a mobile phase velocity of 500 cm/h in a column with a bed height of 20 cm.
[7]Accessed 30 Mar. 2016: http://www.gelifesciences.com/webapp/wcs/stores/servlet/catalog/en/GELifeSciences-uk/products/AlternativeProductStructure_17372/17547401
[8]Determined at 10% breakthrough by frontal analysis at a mobile phase velocity of 100 cm/h in a column with a bed height of 10 cm Comparative Example 2

Dynamic binding capacity as a function of residence time was determined for A) Capto Q and bovine serum albumin (BSA), and B) Q Sepharose Fast Flow[9]. The results obtained are presented in FIG. 1. This shows that residence times below 2 minutes are not possible in these large scaleporous bead columns.

[9]Accessed 30 Mar. 2016 https://www.gelifesciences.com/gehcls_images/GELS/Related%20Content/Files/1334349522418/litdoc11002576_20120514181545.PDF Comparative Example 3

Binding capacities, residence times and productivity values for a variety of commercially available membrane and monolith materials were determined from manufacturers' data. The results obtained are set out in Table 3.

TABLE 3

Examples of membrane and monolith capacities and productivities

| | Functionality | Support type | Capacity | Flowrate (adsorbant volumes/min) | Residence time (min) | Productivity (mg/mL/min) |
|---|---|---|---|---|---|---|
| Sartorius StedimBiotech: Sartobind Q[10] | Anion Exchange | Membrane | 29 mg BSA/mL | 5[11] | 0.2 | 145 |
| Sartorius Stedim Biotech: Sartobind S[12] | Cation Exchange | Membrane | 26 mg lysozyme/mL | 5[13] | 0.2 | 130 |
| Sartorius Stedim Biotech: Sartobind Protein A[14] | Protein A (affinity) | Membrane | 7.5 IgG/mL[15] | 5[16] | 0.2 | 37.5 |
| BIA Separations: CIMmultus QA-8[17] | Anion Exchange | Monolith | 20 mg BSA/mL | 2[18] | 0.5 | 40 |
| BIA Separations: CIMmultus SO3[19] | Cation Exchange | Monolith | 20 mg lysozyme/mL | 2[20] | 0.5 | 40 |

TABLE 3-continued

Examples of membrane and monolith capacities and productivities

| | Functionality | Support type | Capacity | Flowrate (adsorbant volumes/min) | Residence time (min) | Productivity (mg/mL/min) |
|---|---|---|---|---|---|---|
| BIA Separations: CIM r-Protein A-8[21] | Protein A (affinity) | Monolith | 10 IgG/mL | 1[22] | 1 | 10 |

[10]Accessed 30Mar. 2016: https://www.sartorius.co.uk/fileadmin/fm-dam/sartorius_media/Bioprocess-Solutions/Purification-Technologies/Membrane_Chromatography/Data_Sheets/Data_Sartobind-75-plus-150ml_SL-2086-e.pdf
[11]Recommended flowrate of 0.75 L/min through 150 mL membrane of thickness 8 mm
[12]Accessed 30 Mar. 2016 https://www.gelifesciences.com/gehcls_images/GELS/Related%20Content/Files/ 1335359522418/litdoc11002576_20120514181545.PDF
[13]Recommended flowrate of 0.75 L/min through 150 mL membrane of thickness 8 mm
[14]Accessed 30 Mar. 2016: https://www.sartorius.co.uk/en/product/product-detail/93prap06hb-12-a/
[15]2 mL bed volume, 10-15 mg/unit
[16]5-10 ml/min, bed volume 2 mL
[17]Accessed 30 Mar. 2016 http://www.biaseparations.com/interactions/category/30-ion-exchange/product/ download/file_id-2008
[18]Bed volume 8 mL, flowrate at which capacity quoted 16 mL/min
[19]Accessed 30 Mar. 2016 http://www.biaseparations.com/interactions/category/30-ion-exchange/product/ download/file_id-2024
[20]Bed volume 8 mL, flowrate at which capacity quoted 16 mL/min
[21]Accessed 30 Mar. 2016 http://www.biaseparations.com/interactions/category/29-affinity/product/ download/file_id-1970
[22]Bed volume 8 mL, flowrate at which capacity quoted 8 mL/min Further General Aspects of the Invention 1. A process for preparing a functionalised polymeric chromatography medium, which process comprises
   (i) providing a substrate formed of one or more polymer nanofibres,
   (ii) grafting one or more neutral polymer chains from the substrate, and
   (iii) contacting the grafted product with a reagent which functionalises the product of step (ii) as a chromatography medium by introducing one or more charged groups onto the grafted product.

2. The process according to aspect 1, wherein the amount of polymer introduced in step (ii) is between 500-60,000 µmol/g of grafted product.

3. The process according to aspect 1 or 2, wherein the charge density of the product of step (iii) is between 100-2,000 µmol/g of chromatography medium.

4. The process according to any one of the preceding aspects, wherein the pressure drop over the functionalised polymeric chromatography medium is less than 2 MPa when a liquid phase is passed through a thickness of 0.05 to 10 mm of the medium at a flow rate of between 1 to 640 membrane volumes per minute.

5. The process according to any one of the preceding aspects, wherein the productivity of the functionalised polymeric chromatography medium is 50 mg/mL/min to 75,000 mg/mL/min.

6. The process according to any one of the preceding aspects, wherein the productivity of the functionalised polymeric chromatography medium is greater than 200 mg/ml/min.

7. The process according to any one of the preceding aspects, wherein the grafting step (ii) has the effect of increasing the dynamic binding capacity (DBC) of the functionalised polymeric chromatography medium.

8. The process according to any one of the preceding aspects, wherein grafting one or more neutral polymer chains from the substrate comprises growing one or more polymer chains from one or more functional groups present on the substrate, optionally in the presence of one or more catalysts.

9. The process according to aspect 8, wherein the substrate is treated between steps (i) and (ii) to introduce the one or more functional groups, or the substrate is treated between steps (i) and (ii) to deprotect or activate any functional groups on the substrate, or the substrate is treated between steps (i) and (ii) to increase the number/density of functional groups on the substrate.

10. The process according to aspect 8 or 9, wherein the functional groups are hydroxyl, amino or carboxylic acid groups.

11. The process according to any one of aspects 8 to 10, wherein growing one or more polymer chains comprises polymerising a plurality of monomers from one or more functional groups present on the substrate, optionally in the presence of one or more catalysts.

12. The process according to any one of aspects 8 to 11 wherein one or more of the polymer chains is branched.

13. The process according to any one of aspects 8 to 12, wherein growing polymer chains comprises polymerising glycidol from one or more functional groups present on the substrate.

14. The process according to any one of the preceding aspects, wherein the one or more polymer chains are one or more poly-glycerol chains.

15. The process according to any one of the preceding aspects, wherein step (ii) comprises reacting a plurality of compounds of formula

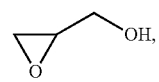

and its enantiomers, with one or more hydroxyl groups present on the nanofibre substrate.

16. The process according to any one of the preceding aspects, wherein in step (iii) the reagent functionalises the grafted product so that the resultant functionalised chromatography medium is suitable for use in anion exchange chromatography method.

17. The process according to aspect 16, wherein
   the chromatography method is a cationic exchange method, and the reagent functionalises the chromatography medium with one or more charged groups comprising one or more carboxylate, sulphonate or phosphonate moieties; or the chromatography method is an anionic exchange method, and the reagent functionalises the chromatography medium with one or more charged groups comprising one or more quaternary amino or diethylamine moieties.

18. The process according to any one of the preceding aspects, wherein the substrate is in the form of a membrane.

19. The process according to any one of the preceding aspects, wherein the polymer is selected from the group consisting of cellulose, cellulose acetate, polysulfones, polyamides, polyacrylic acid, polymethacrylic acid, polyacrylonitrile, polystyrene, polyethylene oxide, and mixtures thereof.

20. The process according to any one of the preceding aspects, wherein the nanofibres have mean diameters from 10 nm to 1000 nm.

21. The process according to any one of the preceding aspects, which process comprises
(i) providing a substrate formed of one or more cellulose nanofibres,
(ii) grafting one or more polyglycerol polymer chains from the substrate by reacting a plurality of compounds of formula

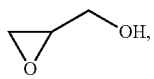

and its enantiomers, with one or more hydroxyl groups present on the substrate, and
(iii) contacting the grafted product with a reagent which functionalises the product of step (ii) as a chromatography medium suitable for use in an ion exchange chromatography method.

22. A functionalised chromatography medium obtainable by the process according to any one of the preceding aspects.

23. A process for preparing a chromatography cartridge, which process comprises carrying out the process of any one of aspects 1 to 21 and incorporating the thus-obtained product into a cartridge.

24. A chromatography cartridge which (a) is obtainable by the process of aspect 23, or (b) which comprises one or more functionalised chromatography media according to aspect 22.

25. Use of a functionalised chromatography medium according to aspect 22 or a chromatography cartridge according to aspect 24 in chromatography.

26. A process for isolating one or more biological molecules from a mobile phase, which process comprises contacting one or more biological molecules in a mobile phase with a functionalised chromatography medium according to aspect 22 or a chromatography cartridge according to aspect 24.

27. The process according to aspect 26 wherein the one or more biological molecules in a mobile phase is contacted with the functionalised chromatography medium for a period of time of one minute or less.

28. A process for preparing a functionalised polymeric chromatography medium, which process comprises
(i) providing a substrate formed of one or more polymer nanofibres,
(ii) grafting one or more neutral polymer chains from the substrate, and
(iii) contacting the grafted product with a reagent which functionalises the product of step (ii) as a chromatography medium.

29. The process according to aspect 28, wherein the amount of polymer introduced in step (ii) is between 500-60,000 µmol/g of grafted product.

30. The process according to aspect 28 or 29, wherein the step of contacting the grafted product with a reagent introduces one or more ligand groups into the grafted product which renders the functionalised product comprising the one or more ligand groups suitable for use as a chromatography medium.

31. The process according to aspect 30, wherein the density of said ligand groups in the product of step (iii) is between 100-2,500 mol/g of chromatography medium.

32. The process according to any one of aspects 28 to 31, wherein the pressure drop over the functionalised polymeric chromatography medium is less than 2 MPa when a liquid phase is passed through a thickness of 0.05 to 10 mm of the medium at a flow rate of between 1 to 640 membrane volumes per minute.

33. The process according to any one of aspects 28 to 32, wherein the productivity of the functionalised polymeric chromatography medium is 50 mg/mL/min to 75,000 mg/mL/min.

34. The process according to any one of aspects 28 to 33, wherein the productivity of the functionalised polymeric chromatography medium is greater than 200 mg/ml/min.

35. The process according to any one of aspects 28 to 34, wherein the grafting step (ii) has the effect of increasing the dynamic binding capacity (DBC) of the functionalised polymeric chromatography medium.

36. The process according to any one of aspects 28 to 35, wherein grafting one or more neutral polymer chains from the substrate comprises growing one or more polymer chains from one or more functional groups present on the substrate, optionally in the presence of one or more catalysts.

37. The process according to aspect 36, wherein the substrate is treated between steps (i) and (ii) to introduce the one or more functional groups, or the substrate is treated between steps (i) and (ii) to deprotect or activate any functional groups on the substrate, or the substrate is treated between steps (i) and (ii) to increase the number/density of functional groups on the substrate.

38. The process according to aspect 36 or 37, wherein the functional groups are hydroxyl, amino or carboxylic acid groups.

39. The process according to any one of aspects 36 to 38, wherein growing one or more polymer chains comprises polymerising a plurality of monomers from one or more functional groups present on the substrate, optionally in the presence of one or more catalysts.

40. The process according to any one of aspects 36 to 39, wherein one or more of the polymer chains is branched.

41. The process according to any one of aspects 36 to 40, wherein growing polymer chains comprises polymerising glycidol from one or more functional groups present on the substrate.

42. The process according to any one of aspects 28 to 41, wherein the one or more polymer chains are one or more poly-glycerol chains.

43. The process according to any one of aspects 28 to 42, wherein step (ii) comprises reacting a plurality of compounds of formula

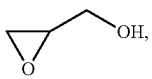

and its enantiomers, with one or more hydroxyl groups present on the nanofibre substrate.

44. The process according to any one of aspects 28 to 43, wherein in step (iii) the reagent functionalises the grafted product so that the resultant functionalised chromatography medium is suitable for use in a chromatography method chosen from the group consisting of ion exchange, affinity capture, hydrophobic interaction and mixed mode methods.

45. The process according to aspect 44, wherein
the chromatography method is a cationic exchange method, and the reagent functionalises the chromatography medium with one or more charged groups comprising one or more carboxylate, sulphonate or phosphonate moieties;
the chromatography method is an anionic exchange method, and the reagent functionalises the chromatography medium with one or more charged groups comprising one or more quaternary amino or diethylamine moieties;
the chromatography method is an affinity capture chromatography method, and the reagent functionalises the chromatography medium with one or more proteins, peptides, antibodies or fragments thereof, dyes, histidine groups, or groups containing a metal cation;
the chromatography method is a hydrophobic interaction chromatography method, and the reagent functionalises the chromatography medium with one or more propyl, butyl, phenyl, or octyl groups; or
the chromatography method is a mixed mode chromatography method, and the reagent functionalises the chromatography medium with one or more MEP, octylamine, N-benzyl methyl ethanolamine or N-benzoyl-homocysteine groups.

46. The process according to any one of aspects 28 to 45, wherein in step (iii) the reagent functionalises the grafted product with one or more Protein A molecules.

47. The process according to any one of aspects 28 to 46, wherein the substrate is in the form of a membrane.

48. The process according to any one of aspects 28 to 47, wherein the polymer is selected from the group consisting of cellulose, cellulose acetate, polysulfones, polyamides, polyacrylic acid, polymethacrylic acid, polyacrylonitrile, polystyrene, polyethylene oxide, and mixtures thereof.

49. The process according to any one of aspects 28 to 48, wherein the nanofibres have mean diameters from 10 nm to 1000 nm.

50. The process according to any one of aspects 28 to 49, which process comprises
(i) providing a substrate formed of one or more cellulose nanofibres,
(ii) grafting one or more polyglycerol polymer chains from the substrate by reacting a plurality of compounds of formula

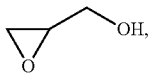

and its enantiomers, with one or more hydroxyl groups present on the substrate, and
(iii) contacting the grafted product with a reagent which functionalises the product of step (ii) as a chromatography medium suitable for use in a chromatography method chosen from the group consisting of ion exchange, affinity capture, hydrophobic interaction and mixed mode methods.

51. A functionalised chromatography medium obtainable by the process according to any one of aspects 28 to 50.

52. A process for preparing a chromatography cartridge, which process comprises carrying out the process of any one of aspects 28 to 50 and incorporating the thus-obtained product into a cartridge.

53. A chromatography cartridge which (a) is obtainable by the process of aspect 52, or (b) which comprises one or more functionalised chromatography media according to aspect 51.

54. Use of a functionalised chromatography medium according to aspect 51 or a chromatography cartridge according to aspect 53 in chromatography.

55. A process for isolating one or more biological molecules from a mobile phase, which process comprises contacting one or more biological molecules in a mobile phase with a functionalised chromatography medium according to aspect 51 or a chromatography cartridge according to aspect 53.

56. The process according to aspect 55 wherein the one or more biological molecules in a mobile phase is contacted with the functionalised chromatography medium for a period of time of one minute or less.

57. The process according to aspect 55 or aspect 56, wherein the one or more biological molecules are one or more monoclonal antibodies, or proteins engineered to exhibit a site with an affinity for Protein A binding, and the functionalised chromatography medium carries at least one Protein A ligand group.

58. The process according to any one of aspects 28 to 50, wherein step (iii) of the process comprises contacting the grafted product with allyl glycidyl ether and a halohydrin-forming reagent.

59. The process according to any one of aspects 28 to 50, wherein in step (iii):
(a) the grafted product is contacted with allyl glycidyl ether;
(b) the product of step (a) is treated with a halohydrin-forming reagent; and
(c) the product of step (b) is contacted with Protein A.

60. The process according to any one of aspects 28 to 50, wherein step (iii) comprises contacting the grafted product with a plurality of reagents which together functionalise the product of step (ii) as a chromatography medium, and wherein the plurality of reagents comprises a halohydrin-forming reagent.

61. The process according to aspect 60, wherein the grafted product is contacted sequentially with the plurality of reagents.

The invention claimed is:
1. A process for preparing a functionalised polymeric chromatography medium, which process comprises
(i) providing a substrate formed of one or more polymer nanofibres having a mean diameter from between about 10 nm to about 1000 nm,
(ii) grafting one or more neutral polymer chains from the substrate, and
(iii) contacting the grafted product with a reagent which functionalises the product of step (ii) as a chromatography medium, wherein step (ii) comprises reacting a plurality of compounds of formula

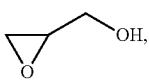

and/or its enantiomers, and/or its derivatives of formula (I) and/or enantiomers and/or diastereomers thereof:

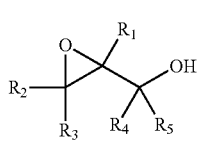

with one or more functional groups present on the substrate, and growing the one or more neutral polymer chains from the one or more functional groups present on the substrate,
wherein $R_1$, $R_2$, $R_3$, $R_4$ and $R_5$ may be the same or different, and are chosen from H, halo, $C_1$-$C_4$ alkyl, or $C_1$-$C_4$ alkoxy provided that at least one of $R_1$, $R_2$, $R_3$, $R_4$ or $R_5$ is not hydrogen.

2. The process according to claim 1, wherein step (ii) comprises reacting a plurality of compounds of formula

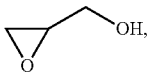

and/or its enantiomers, with one or more functional groups present on the substrate, and growing the one or more neutral polymer chains from the one or more functional groups present on the substrate.

3. The process according to claim 1, wherein the one or more polymer nanofibres comprise a polymer selected from the group consisting of cellulose, cellulose acetate, polysulfones, polyamides, polyacrylic acid, polymethacrylic acid, polyacrylonitrile, polystyrene, polyethylene oxide, and mixtures thereof, preferably wherein the polymer is selected from the group consisting of cellulose, cellulose acetate, and a mixture thereof.

4. The process according to claim 1, wherein the amount of polymer in the one or more neutral polymer chains formed in step (ii) is between 500-60,000 µmol/g of grafted product.

5. The process according to claim 1, wherein the step of contacting the grafted product with a reagent introduces one or more ligand groups into the grafted product which renders the functionalised product comprising the one or more ligand groups suitable for use as a chromatography medium.

6. The process according to claim 5, wherein the density of said ligand groups in the functionalised product of step (iii) is between 100-2,500 µmol/g of chromatography medium.

7. The process according to claim 1, wherein the functionalised polymeric chromatography medium is in the form of a membrane, and wherein the pressure drop over the functionalised polymeric chromatography medium is less than 2 MPa when a liquid phase is passed through a thickness of 0.05 to 10 mm of the medium at a flow rate of between 1 to 640 membrane volumes per minute.

8. The process according to claim 1, wherein the productivity of the functionalised polymeric chromatography medium is 50 mg/mL/min to 75,000 mg/mL/min.

9. The process according to claim 1, wherein the productivity of the functionalised polymeric chromatography medium is greater than 200 mg/ml/min.

10. The process according to claim 1, wherein the grafting step (ii) has the effect of increasing the dynamic binding capacity (DBC) of the functionalised polymeric chromatography medium, when compared with the DBC of functionalized polymeric chromatography medium which does not have a neutral polymer chain grafted to its substrate.

11. The process according to claim 1, wherein the substrate is treated between steps (i) and (ii) to introduce the one or more functional groups, or the substrate is treated between steps (i) and (ii) to deprotect or activate any functional groups on the substrate, or the substrate is treated between steps (i) and (ii) to increase the number/density of functional groups on the substrate.

12. The process according to claim 1, wherein the grafting step (ii) is carried out under conditions which additionally, in the same step, introduce the one or more functional groups, or deprotect or activate any functional groups on the substrate, or increase the number/density of functional groups on the substrate.

13. The process according to claim 12, wherein the grafting step (ii) is effected in the presence of aqueous alkali, preferably NaOH or KOH, in water or water:ethanol, preferably in water.

14. The process according to claim 1, wherein the one or more functional groups present on the substrate comprise hydroxyl groups.

15. The process according to claim 1, wherein in the functionalisation step (iii), the functionalising reagent is selected from the group consisting of glycidyltrimethylammonium chloride (GMAC), 1,4-butanesulfone, sodium chloroacetate, $NaIO_4$ followed by Protein A, divinylsulfone followed by Protein A, allyl glycidyl ether followed firstly by a halohydrin-forming reagent, and subsequently by Protein A, allyl glycidyl ether followed firstly by an epoxide-forming reagent and subsequently by Protein A, and combinations thereof.

16. The process according to claim 10, wherein one or more of the neutral polymer chains is branched.

17. The process according to claim 1, wherein in step (iii) the reagent functionalises the grafted product so that the resultant functionalised chromatography medium is suitable for use in a chromatography method chosen from the group consisting of ion exchange, affinity capture, hydrophobic interaction and mixed mode methods.

18. The process according to claim 17, wherein
the chromatography method is a cationic exchange method, and the reagent functionalises the chromatography medium with one or more charged groups comprising one or more carboxylate, sulphonate or phosphonate moieties;
the chromatography method is an anionic exchange method, and the reagent functionalises the chromatography medium with one or more charged groups comprising one or more quaternary amino or diethylamine moieties;
the chromatography method is an affinity capture chromatography method, and the reagent functionalises the chromatography medium with one or more proteins, peptides, antibodies or fragments thereof, dyes, histidine groups, or groups containing a metal cation;

the chromatography method is a hydrophobic interaction chromatography method, and the reagent functionalises the chromatography medium with one or more propyl, butyl, phenyl, or octyl groups; or the chromatography method is a mixed mode chromatography method, and the reagent functionalises the chromatography medium with one or more MEP, octylamine, N-benzyl methyl ethanolamine or N-benzoylhomocysteine groups.

19. The process according to claim 1, wherein in step (iii) the reagent functionalises the grafted product with one or more Protein A molecules.

20. The process according to claim 1, wherein step (iii) involves multiple steps that together functionalise the product of step (ii) as a chromatography medium.

21. The process according to claim 20, wherein in step (iii):
(a) the grafted product is contacted with a reagent selected from the group selected from divinyl sulfone, allyl glycidyl ether, and combinations thereof;
(b) the product of step (a) is optionally treated with a halohydrin-forming reagent; and
(c) the product of step (b) is contacted with Protein A.

22. The process according to claim 1, wherein the substrate is in the form of a membrane.

23. The process according to claim 1, wherein the nanofibres have mean diameters from 10 nm to 1000 nm.

24. The process according to claim 1, which process comprises
(i) providing a substrate formed of one or more cellulose nanofibres,
(ii) grafting one or more polyglycerol polymer chains from the substrate by reacting a plurality of compounds of formula

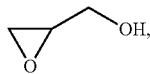

and/or its enantiomers, and/or its derivatives of formula (I) and/or enantiomers and/or diastereomers thereof:

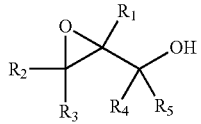

with one or more hydroxyl groups present on the substrate, and growing the one or more neutral polymer chains from the one or more functional groups present on the substrate, and (iii) contacting the grafted product with a reagent which functionalises the product of step (ii) as a chromatography medium suitable for use in a chromatography method chosen from the group consisting of ion exchange, affinity capture, hydrophobic interaction and mixed mode methods, wherein $R_1$, $R_2$, $R_3$, $R_4$ and $R_5$ may be the same or different, and are chosen from H, halo, $C_1$-$C_4$ alkyl, or $C_1$-$C_4$ alkoxy provided that at least one of $R_1$, $R_2$, $R_3$, $R_4$ or $R_5$ is not hydrogen.

25. The process according to claim 24, wherein step (ii) comprises grafting one or more polyglycerol polymer chains from the substrate by reacting a plurality of compounds of formula

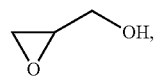

and/or its enantiomers with one or more hydroxyl groups present on the substrate and growing the one or more neutral polymer chains from the one or more functional groups present on the substrate.

26. A functionalised chromatography medium obtainable by the process according to claim 1.

27. A process for preparing a chromatography cartridge, which process comprises carrying out the process of claim 1 and incorporating the thus-obtained product into a cartridge.

28. A chromatography cartridge which is obtainable by the process of claim 27.

29. Use of a functionalised chromatography medium according to claim 26, wherein the use comprises contacting one or more biological molecules with the chromatography medium and eluting the one or more biological molecules from the chromatography medium.

30. A process for isolating one or more biological molecules from a mobile phase, which process comprises contacting one or more biological molecules in a mobile phase with a functionalised chromatography medium according to claim 26.

31. The process according to claim 30 wherein the one or more biological molecules in a mobile phase is contacted with the functionalised chromatography medium for a period of time of one minute or less.

32. The process according to claim 30, wherein the one or more biological molecules are one or more monoclonal antibodies, or proteins engineered to exhibit a site with an affinity for Protein A binding, and the functionalised chromatography medium carries at least one Protein A ligand group.

* * * * *